US012747441B2

(12) United States Patent
Lipinski et al.

(10) Patent No.: US 12,747,441 B2
(45) **Date of Patent: *Sep. 29, 2026**

(54) RIBOSWITCH MODULATED GENE THERAPY FOR RETINAL DISEASES

(71) Applicant: The Medical College of Wisconsin, Inc., Milwaukee, WI (US)

(72) Inventors: Daniel M. Lipinski, Milwaukee, WI (US); Chris A. Reid, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 386 days.

This patent is subject to a terminal disclaimer.

(21) Appl. No.: 18/359,665

(22) Filed: Jul. 26, 2023

(65) Prior Publication Data

US 2024/0158800 A1 May 16, 2024

Related U.S. Application Data

(63) Continuation of application No. 16/492,878, filed as application No. PCT/US2018/021719 on Mar. 9, 2018, now Pat. No. 12,012,602.

(60) Provisional application No. 62/469,705, filed on Mar. 10, 2017.

(51) Int. Cl.

| | |
|---|---|
| ***C12N 15/115*** | (2010.01) |
| ***A61K 48/00*** | (2006.01) |
| ***C12N 15/67*** | (2006.01) |

(52) U.S. Cl.

CPC .......... *C12N 15/115* (2013.01); *A61K 48/005* (2013.01); *A61K 48/0075* (2013.01); *C12N 15/67* (2013.01); *C12N 2310/141* (2013.01); *C12N 2310/16* (2013.01); *C12N 2310/3519* (2013.01); *C12N 2320/50* (2013.01); *C12N 2750/14143* (2013.01); *C12N 2830/00* (2013.01)

(58) Field of Classification Search

CPC C12N 15/115; C12N 15/67; C12N 2310/141; C12N 2310/16; C12N 2310/3519; C12N 2320/50; C12N 2750/14143; C12N 2830/00; A61K 48/005; A61K 48/0075; A61P 27/06

See application file for complete search history.

(56) References Cited

U.S. PATENT DOCUMENTS

| | | | | |
|---|---|---|---|---|
| 7,306,799 | B2 * | 12/2007 | Wiegand | A61K 38/179 514/8.1 |
| 8,158,595 | B2 | 4/2012 | Galloway | |
| 8,299,043 | B2 | 10/2012 | Poeschla et al. | |
| 8,603,996 | B2 | 12/2013 | Galloway | |
| 8,865,667 | B2 | 10/2014 | Smolke | |
| 8,951,982 | B2 * | 2/2015 | Jiménez | A61P 31/00 514/44 A |
| 9,040,495 | B2 | 5/2015 | Smolke | |
| 9,315,862 | B2 | 4/2016 | Smolke | |
| 10,501,811 | B2 | 12/2019 | Yoshida et al. | |
| 10,620,109 | B2 | 4/2020 | Saito et al. | |
| 12,012,602 | B2 * | 6/2024 | Lipinski | C12N 15/67 |
| 12,286,631 | B2 * | 4/2025 | Lipinski | A61K 48/0075 |
| 2002/0166132 | A1 | 11/2002 | Scherman | |
| 2005/0220768 | A1 | 10/2005 | McVey et al. | |
| 2006/0088864 | A1 * | 4/2006 | Smolke | C12Q 1/6897 435/325 |
| 2007/0089186 | A1 | 4/2007 | Huang | |
| 2008/0199961 | A1 | 8/2008 | Rasko | |
| 2009/0210952 | A1 | 8/2009 | Wu et al. | |
| 2010/0152212 | A1 | 6/2010 | Breaker | |
| 2010/0184810 | A1 | 7/2010 | Breaker | |
| 2010/0286082 | A1 | 11/2010 | Breaker | |
| 2012/0321647 | A1 | 12/2012 | Breaker | |
| 2013/0012527 | A1 | 1/2013 | Breaker | |
| 2013/0039971 | A1 | 2/2013 | Dejneka | |
| 2013/0143955 | A1 | 6/2013 | Breaker | |
| 2015/0024024 | A1 | 1/2015 | Tao | |
| 2016/0333373 | A1 | 11/2016 | Farley et al. | |
| 2017/0051290 | A1 * | 2/2017 | Byrne | C12N 15/1136 |
| 2017/0370821 | A1 | 12/2017 | Saito et al. | |
| 2018/0100203 | A1 | 4/2018 | Yoshida et al. | |
| 2020/0056248 | A1 | 2/2020 | Yoshida et al. | |

FOREIGN PATENT DOCUMENTS

| | | | |
|---|---|---|---|
| AU | 2012265582 | A1 | 1/2013 |
| CN | 102727513 | A | 10/2012 |
| CN | 102895673 | A | 1/2013 |
| CN | 103068983 | A | 4/2013 |
| CN | 105431204 | A | 3/2016 |
| CN | 106074591 | A | 11/2016 |
| WO | 2006021817 | A2 | 3/2006 |
| WO | 2011119871 | A1 | 9/2011 |
| WO | 2011157777 | A1 | 12/2011 |

(Continued)

OTHER PUBLICATIONS

Boye, S. E., et al. "A comprehensive review of retinal gene therapy." Molecular therapy 21.3 (2013): 509-519.

Chang, A. L., et al. "Synthetic RNA switches as a tool for temporal and spatial control over gene expression." Current opinion in biotechnology 23.5 (2012): 679-688.

Enslow, R., et al. "Association of anti-VEGF injections with progression of geographic atrophy." Ophthalmology and eye diseases 8 (2016): OED-S38863.

(Continued)

*Primary Examiner* — Brian Whiteman
*Assistant Examiner* — Khaleda B Hasan
(74) *Attorney, Agent, or Firm* — Quarles & Brady LLP

(57) ABSTRACT

The present invention provides constructs comprising modified riboswitches to regulate expression of a transgene within a subject. Methods of treating a disease, specifically an eye disease, are also contemplated.

19 Claims, 35 Drawing Sheets

Specification includes a Sequence Listing.

(56) References Cited

FOREIGN PATENT DOCUMENTS

| | | | |
|---|---|---|---|
| WO | 2012087983 | A1 | 6/2012 |
| WO | 2015006734 | A1 | 1/2015 |
| WO | 2016210293 | A1 | 12/2016 |
| WO | 2017042239 | A1 | 3/2017 |

OTHER PUBLICATIONS

Ferguson, L. R.. Regulation of gene expression for therapy of age related macular degeneration. Diss. University of Florida, 2009.
International Searching Authority, International Search Report and Written Opinion for application PCT/ US2018/021719, mailed on Jul. 3, 2018, 14 pages.
Martin, D. F., et al. “Ranibizumab and bevacizumab for treatment of neovascular age-related macular degeneration: two-year results.” Ophthalmology 119.7 (2012): 1388-1398.
Rottiers, V et al. “MicroRNAs in metabolism and metabolic disorders.” Nature reviews Molecular cell biology 13.4 (2012): 239.
Beilstein, K., et al. Conditional Control of Mammalian Gene Expression by Tetracycline-Dependent Hammerhead Ribozymes. ACS synthetic biology 4, 526-534 (2015).
Chen, Y. Y., et al. Genetic control of mammalian T-cell proliferation with synthetic RNA regulatory systems. Proceedings of the National Academy of Sciences of the United States of America 107, 8531-8536, https://doi.org/10.1073/ pnas.1001721107 (2010).
Win, M. N. et al. “A modular and extensible RNA-based gene-regulatory platform for engineering cellular function.” Proceedings of the National Academy of Sciences 104.36 (2007): 14283-14288.
Beisel, C. et al., Nucleic Acids Research, 2011, vol. 30, No. 7, 2981-2994.
Kim M et al., “Angiogenesis in glaucoma filtration surgery and neovascular glaucoma: A review”, Surv Ophthalmol., 60/6, pp. 524-535, Nov. 1, 2015.
Agrawal, S. et al., MicroRNA Signature and Function in Retinal Neovascularization, World Journal of Biological Chemistry, 2014, 5(1):1-11.
Drewry, M. et al., Differentially Expressed microRNAs in the Aqueous Humor of Patients with Exfoliation Glaucoma or Primary Open-Angle Glaucoma, Human Molecular Genetics, 2018, 27(7):1263-1275.
Guo, R. et al., Relationship Between the Pathogenesis of Glaucoma and miRNA, Ophthalmic Research, 2017, 57 (3):194-199.
Guzman-Aranguez, A. et al., Small-Interfering RNAs (siRNAs) as a Promising Rool for Ocular Therapy, British Journal of Pharmacology, 2013, 170(4):730-747.
Ketzer, P. et al., Artificial Riboswitches for Gene Expression and Replication Control of DNA and RNA Viruses, Proceedings of the National Academy of Sciences, 2014, 111(5):E554-E562.
Ricci, V. et al., Aflibercept a New Target Therapy in Cancer Treatment: A Review, Critical Reviews in Oncology/Hematology, 2015, 96(3):569-576.
European Patent Office, Extended Search Report, Application No. 18764686.4, Dec. 8, 2020, 15 pages.
Doench, John G. et al., “siRNAs can function as miRNAs”, Genes & Development, 17:438-442, downloaded from genesdev.cship.org on Sep. 25, 2022.
Miki, Kenji et al., “Efficient Detection and Purification of Cell Populations Using Synthetic MicroRNA Switches”, Cell Stem Cell 16, 699-711, Jun. 4, 2015.
Barraza, R. et al., Prostaglandin Pathway Gene Therapy for Sustained Reduction of Intraocular Pressure, Molecular Therapy, 2010, 18(3):491-501.
Reid, C. et al., Development of an Inducible Anti-VEGF rAAV Gene Therapy Strategy for the Treatment of Wet AMD, Scientific Reports, 2018, 8:11763, pp. 1-14.
Siemieniuch, M. et al., Prostaglandin Endoperoxide Synthase 2 (PTGS2) and Prostaglandins F2a and E2 Synthases (PGFS and PGES) Expression and Prostaglandin F2a and E2 Secretion Following Oestrogen and/or Progesterone Stimulation of the Feline Endometrium, Reproduction in Domestic Animals, 2013, 48:72-78.
European Patent Office, Extended Search Report, Application No. 24158111.5, Jul. 26, 2024, 13 pages.

* cited by examiner

Blue: aptamer domain: binds directly to ligand

Red: Expression platform (ribozyme): undergoes conformational change in response to alternations in the aptamer structure (causes cleavage)

SLIM switch design

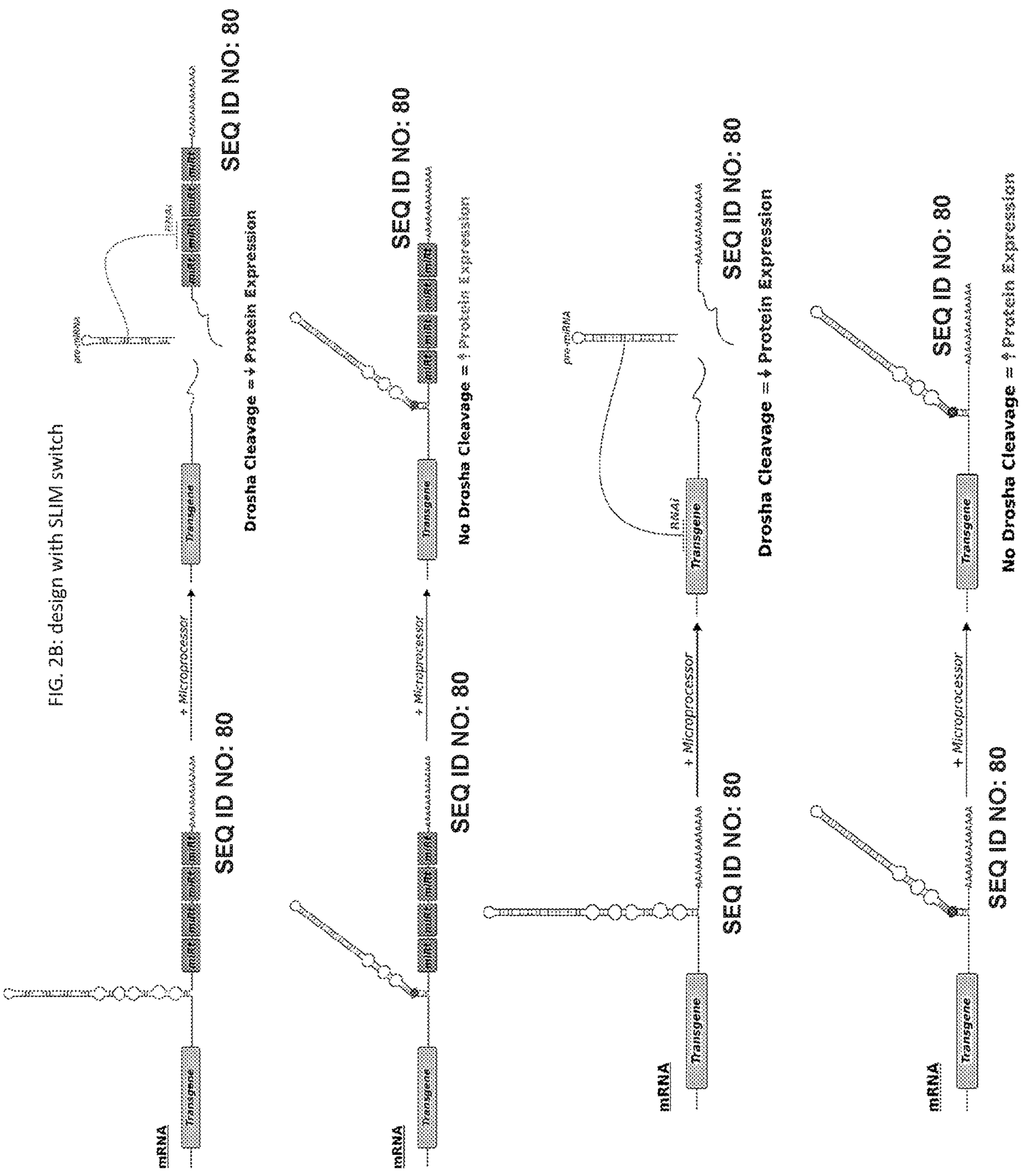
FIG. 2B: design with SLIM switch

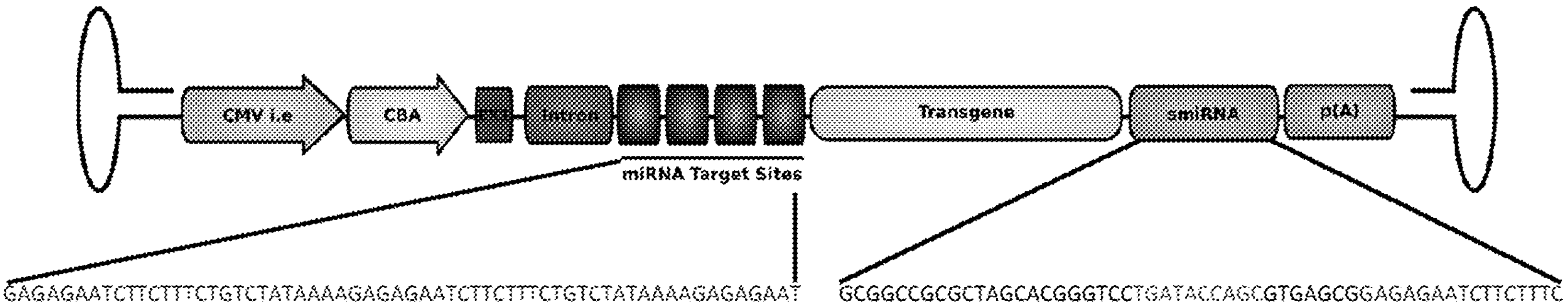

GAGAGAATCTTCTTTCTGTCTATAAAAGAGAGAATCTTCTTTCTGTCTATAAAAGAGAGAAT
CTTCTTTCTGTCTATAAAAGAGAGAATCTTCTTTCTGTCTAT (SEQ ID NO:68)

GCGGCCGCGCTAGCACGGGTCCTGATACCAGCGTGAGCGGAGAGAATCTTCTTTC
TGTCTATTAGTGAAGCCACAGATGTAATAGACAGAAAGAAGATTCTCTCCGCCTAC
GCCCTTGGCAGCA (SEQ ID NO:69)

Red: Novel Sequence
Yellow: Previously published theophylline aptamer sequence
black: Previously published miRNA sequence FIG. 2C (rAAV vector encoding Aflibecept and SLIM switch)

FIG. 3
ON type Aptamer

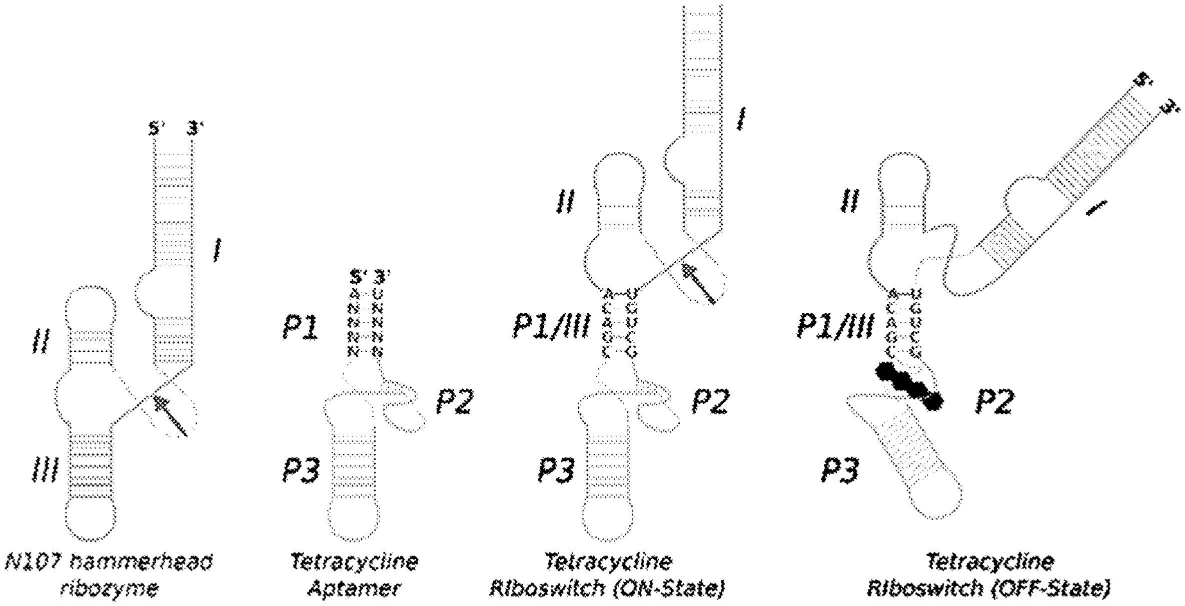

*FIG. 4*

*rAAV smCBA-Aflibercept-Theo-SLIM Construct:*

| *Element* | *Color* |
|---|---|
| | |
| switchable miRNA | Red (SEQ ID. NO:1 ) |
| miRNA Target Sites | Light Blue (SEQ ID. NO:2 ) |
| Inverted Terminal Repeats | Bold (SEQ ID. NO:3 ) |
| bGH Poly(A) | Teal Highlight (SEQ ID. NO:4 ) |
| Chimeric Intron | Orange (SEQ ID. NO:5 ) |
| Chicken Beta Actin Promoter | Purple(SEQ ID. NO:6 ) |
| CMV enhancer | Green(SEQ ID. NO:7 ) |
| cDNA Aflibercept | Yellow Highlight (SEQ ID. NO:8 ) |

FIG. 5

GGTTGGCCACTCCCTCTCTGCGCGCTCGCTCGCTCACTGAGGCCGGGCGACCAAAGGTCGCCCGACGCCCGGGCTTTGCCCG
GGCGGCCTCAGTGAGCGAGCGAGCGCGCAGAGAGGGAGTGGCCAACTCCATCACTAGGGGTTCCTAGATCTGAATTCGGTA
CCCCTAGTTATTAATAGTAATCAATTACGGGGTCATTAGTTCATAGCCCATATATGGAGTTCCGCGTTACATAACTTACGGTAAA
TGGCCCGCCTGGCTGACCGCCCAACGACCCCCGCCCATTGACGTCAATAATGACGTATGTTCCCATAGTAACGCCAATAGGGA
CTTTCCATTGACGTCAATGGGTGGACTATTTACGGTAAACTGCCCACTTGGCAGTACATCAAGTGTATCATATGCCAAGTACGC
CCCCTATTGACGTCAATGACGGTAAATGGCCCGCCTGGCATTATGCCCAGTACATGACCTTATGGGACTTTCCTACTTGGCAGT
ACATCTACGTATTAGTCATCGCTATTACCATGGTCGAGGTGAGCCCCACGTTCTGCTTCACTCTCCCCATCTCCCCCCCCTCCCCA
CCCCCAATTTTGTATTTATTTATTTTTTAATTATTTTGTGCAGCGATGGGGGCGGGGGGGGGGGGGGGGCGCGCGCCAGGCG
GGGCGGGGCGGGGCGAGGGGCGGGGCGGGGCGAGGCGGAGAGGTGCGGCGGCAGCCAATCAGAGCGGCGCGCTCCGAA
AGTTTCCTTTTATGGCGAGGCGGCGGCGGCGGCGGCCCTATAAAAAGCGAAGCGCGCGGCGGGCGGGAGTCGCTGCGACGC
TGCCTTCGCCCCGTGCCCCGCTCCGCCGCCGCCTCGCGCCGCCCGCCCCGGCTCTGACTGACCGCGTTACTCCCACAGGTGAGC
GGGCGGGACGGCCCTTCTCCTCCGGGCTGTAATTAGCGCTTGGTTTAATGACGGCTTGTTTCTTTTCTGTGGCTGCGTGAAAGC
CTTGAGGGGCTCCGGGAGCTAGAGCCTCTGCTAACCATGTTCATGCCTTCTTCTTTTTCCTACAGCTCCTGGGCAACGTGCTGG
TTATTGTGCTGTCTCATCATTTTGGCAAAGAATTCCTCGAAGATCTAGGCAACGCGTATTGGGATCTCGAGGCGGCCGCGCCGC
CACCCTAGCGAGAGAATCTTCTTTCTGTCTATAAAAGAGAGAATCTTCTTTCTGTCTATAAAAGAGAGAATCTTCTTTCTGTCTA
TAAAAGAGAGAATCTTCTTTCTGTCTATGTCGACCCTGCAATGGTATCATATTGGGACACAGGAGTCCTCCTGTGCGCCCTTTT
GAGCTGTCTTTTGCTGACGGGTTCTTCTTCAGGTTCTGATACCGGGAGACCATTCGTTGAAATGTATAGTGAGATACCCGAAAT
TATACATATGACTGAAGGGCGCGAGCTCGTCATACCCTGTCGGGTAACAAGTCCAAACATAACAGTGACCCTGAAGAAGTTCC
CTTTGGATACTCTCATTCCCGACGGGAAGCGAATAATTTGGGACTCAAGGAAGGGATTTATCATATCTAATGCAACATATAAG
GAAATAGGGCTCCTCACATGCGAAGCCACAGTCAACGGGCACCTCTACAAAACTAATTACCTGACCCATCGACAGACAAATAC
CATCATTGATGTGGTTCTGAGTCCATCTCATGGAATAGAGTTGAGTGTAGGGGAGAAGCTTGTTCTCAATTGCACAGCTAGAA
CCGAGTTGAACGTGGGTATCGATTTTAACTGGGAATACCCATCTAGTAAGCACCAACACAAAAAACTTGTCAATCGAGATTTG
AAAACTCAATCTGGTAGCGAGATGAAAAAGTTCCTGTCAACTCTTACAATCGATGGCGTGACCCGGAGTGATCAAGGATTGTA
TACCTGCGCCGCCAGCTCTGGCCTGATGACTAAAAAGAACAGCACCTTTGTACGAGTGCATGAAAAGGATAAGACTCATACAT
GCCCTCCTTGTCCCGCTCCAGAGCTGCTGGGAGGTCCCAGTGTTTTCCTCTTCCCACCAAAGCCCAAAGATACTCTGATGATTAG
CCGGACCCCTGAGGTGACTTGCGTCGTGGTGGATGTTTCACATGAAGATCCAGAAGTGAAGTTCAATTGGTACGTTGATGGTG
TGGAGGTACACAATGCCAAGACTAAACCTCGGGAGGAACAGTATAACAGCACTTACAGAGTTGTCAGCGTACTCACAGTGCTT
CATCAGGACTGGTTGAATGGTAAGGAGTATAAGTGCAAAGTGAGTAATAAGGCTCTGCCAGCACCCATAGAGAAGACAATCT
CAAAGGCCAAAGGCCAGCCCCGAGAACCACAAGTATACACACTGCCACCTAGTAGAGACGAGTTGACAAAAAATCAGGTCAG
CCTCACCTGTCTCGTGAAAGGCTTCTACCCTAGCGACATTGCCGTAGAATGGGAAAGCAACGGGCAACCAGAAAACAATTATA
AGACAACACCTCCCGTTCTCGATAGTGACGGAAGTTTCTTCCTGTATAGCAAACTTACCGTGGATAAATCAAGATGGCAGCAA
GGTAATGTGTTTAGCTGTTCAGTAATGCACGAAGCTCTGCATAACCACTACACCCAAAAATCTTTGTCTCTGTCTCCAGGGTGA
GCGTATCAGCAGGTCCCATAAGCTTTCGACAATTAACGAGTGTGTACTCGTTCTATCATCTCACAGTTAAAGTCGGGAGAATAG
GAGCCGCACGGGTCCTGATACCAGCGTGAGCGGAGAGAATCTTCTTTCTGTCTATTAGTGAAGCCACAGATGTAATAGACAGA
AAGAAGATTCTCTCCGCCTACGCCCTTGGCAGCACCGTACGGTTCGATCAGCTTATTGGTACATGATAAGTCTCAGGCATCGTA
CGATGTCGACCTGCAGGAGTCGGTCGACTAGAGCTCGCTGATCAGCCTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGGCAGGACAGCAAGGGGGAGGATTGGGAAGACAATAGCAGGC
ATGCTGGGGAGAGATCTAGGAACCCCTAGTGATGGAGTTGGCCACTCCCTCTCTGCGCGCTCGCTCGCTCACTGAGGCCGCC
CGGGCAAAGCCCGGGCGTCGGGCGACCTTTGGTCGCCCGGCCTCAGTGAGCGAGCGAGCGCGCAGAGAGGGAGTGGCCA
ACC (SEQ ID NO:9)

C57BL6/J mouse injected intravitreally with 1.0x10$^{10}$ vector genomes(vg) of rAAV2.smCBA-hGFP-3x-L2Bulge9. (A) Pre-treatment retinal imaging 4 weeks post injection. (B) Fluorescent imaging two hours post-gavage @ 10mg/kg of theophylline (activating ligand).

L2Bulge18tc riboswitch

FIG. 14A smCBA-Eylea (non-inducible)

FIG. 14B smCBA-Eylea-1x-TC45 (Standard Diet)

FIG. 14C smCBA-Eylea-1x-TC45 (Tetracyline Diet)

FIG. 14D PBS

FIG. 16A

*Recombinant VEGF inhibitor cDNA (reverse engineered from Elyea protein sequence) with synthetic nerve growth factor secretion signal (SEQ ID NO:18)*

**XATGTCCATGTTGTTCTACACTCTGATCACAGCTTTTCTGATCGGCATACAGGCGGAACC
ACACTCAGTCTGATACCGGGAGACCATTCGTTGAAATGTATAGTGAGATACCCGAAATTA
TACATATGACTGAAGGGCGCGAGCTCGTCATACCCTGTCGGGTAACAAGTCCAAACATA
ACAGTGACCCTGAAGAAGTTCCCTTTGGATACTCTCATTCCCGACGGGAAGCGAATAATT
TGGGACTCAAGGAAGGGATTTATCATATCTAATGCAACATATAAGGAAATAGGGCTCCTC
ACATGCGAAGCCACAGTCAACGGGCACCTCTACAAAACTAATTACCTGACCCATCGACA
GACAAATACCATCATTGATGTGGTTCTGAGTCCATCTCATGGAATAGAGTTGAGTGTAGG
GGAGAAGCTTGTTCTCAATTGCACAGCTAGAACCGAGTTGAACGTGGGTATCGATTTTAA
CTGGGAATACCCATCTAGTAAGCACCAACACAAAAAACTTGTCAATCGAGATTTGAAAAC
TCAATCTGGTAGCGAGATGAAAAAGTTCCTGTCAACTCTTACAATCGATGGCGTGACCCG
GAGTGATCAAGGATTGTATACCTGCGCCGCCAGCTCTGGCCTGATGACTAAAAAGAACA
GCACCTTTGTACGAGTGCATGAAAAGGATAAGACTCATACATGCCCTCCTTGTCCCGCTC
CAGAGCTGCTGGGAGGTCCCAGTGTTTTCCTCTTCCCACCAAAGCCCAAAGATACTCTGA
TGATTAGCCGGACCCCTGAGGTGACTTGCGTCGTGGTGGATGTTTCACATGAAGATCCA
GAAGTGAAGTTCAATTGGTACGTTGATGGTGTGGAGGTACACAATGCCAAGACTAAACC
TCGGGAGGAACAGTATAACAGCACTTACAGAGTTGTCAGCGTACTCACAGTGCTTCATC
AGGACTGGTTGAATGGTAAGGAGTATAAGTGCAAAGTGAGTAATAAGGCTCTGCCAGCA
CCCATAGAGAAGACAATCTCAAAGGCCAAAGGCCAGCCCCGAGAACCACAAGTATACA
CACTGCCACCTAGTAGAGACGAGTTGACAAAAAATCAGGTCAGCCTCACCTGTCTCGTG
AAAGGCTTCTACCCTAGCGACATTGCCGTAGAATGGGAAAGCAACGGGCAACCAGAAA
ACAATTATAAGACAACACCTCCCGTTCTCGATAGTGACGGAAGTTTCTTCCTGTATAGCA
AACTTACCGTGGATAAATCAAGATGGCAGCAAGGTAATGTGTTTAGCTGTTCAGTAATGC
ACGAAGCTCTGCATAACCACTACACCCAAAAATCTTTGTCTCTGTCTCCAGGGTGA**AAAC
AAACAAAX

X = positions for SLIM regulatory elements (SLIM Sequences in FIG. 18)

Complete AAV expression cassette for SLIM EYLEA (SEQ ID NO:19)

GGTTGGCCACTCCCTCTCTGCGCGCTCGCTCGCTCACTGAGGCCGGGCGACCAAAGGTC
GCCCGACGCCCGGGCTTTGCCCGGGCGGCCTCAGTGAGCGAGCGAGCGCGCAGAGAGG
GAGTGGCCAACTCCATCACTAGGGGTTCCTAGATCTGAATTCGGTACCCCTAGTTATTAAT
AGTAATCAATTACGGGGTCATTAGTTCATAGCCCATATATGGAGTTCCGCGTTACATAACTT
ACGGTAAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGGACTATT
TACGGTAAACTGCCCACTTGGCAGTACATCAAGTGTATCATATGCCAAGTACGCCCCCTAT
TGACGTCAATGACGGTAAATGGCCCGCCTGGCATTATGCCCAGTACATGACCTTATGGGA
CTTTCCTACTTGGCAGTACATCTACGTATTAGTCATCGCTATTACCATGGTCGAGGTGAGC
CCCACGTTCTGCTTCACTCTCCCCATCTCCCCCCCCTCCCCACCCCCAATTTTGTATTTATT
TATTTTTTAATTATTTTGTGCAGCGATGGGGGCGGGGGGGGGGGGGGGGCGCGCGCCAG
GCGGGGCGGGGCGGGGCGAGGGGCGGGGCGGGGCGAGGCGGAGAGGTGCGGCGGCA
GCCAATCAGAGCGGCGCGCTCCGAAAGTTTCCTTTTATGGCGAGGCGGCGGCGGCGGCG
GCCCTATAAAAAGCGAAGCGCGCGGCGGGCGGGAGTCGCTGCGACGCTGCCTTCGCCCC

FIG. 16B

GTGCCCCGCTCCGCCGCCGCCTCGCGCCGCCCGCCCCGGCTCTGACTGACCGCGTTACT
CCCACAGGTGAGCGGGCGGGACGGCCCTTCTCCTCCGGGCTGTAATTAGCGCTTGGTTTA
ATGACGGCTTGTTTCTTTTCTGTGGCTGCGTGAAAGCCTTGAGGGGCTCCGGGAGCTAGA
GCCTCTGCTAACCATGTTCATGCCTTCTTCTTTTTCCTACAGCTCCTGGGCAACGTGCTGG
TTATTGTGCTGTCTCATCATTTTGGCAAAGAATTCCTCGAAGATCTAGGCAACGCGTCTCGA
GGCGGCCGCCGCCACCXATGGTATCATATTGGGACACAGGAGTCCTCCTGTGCGCCCTT
TTGAGCTGTCTTTTGCTGACGGGTTCTTCTTCAGGTTCTGATACCGGGAGACCATTCGTTG
AAATGTATAGTGAGATACCCGAAATTATACATATGACTGAAGGGCGCGAGCTCGTCATA
CCCTGTCGGGTAACAAGTCCAAACATAACAGTGACCCTGAAGAAGTTCCCTTTGGATACT
CTCATTCCCGACGGGAAGCGAATAATTTGGGACTCAAGGAAGGGATTTATCATATCTAAT
GCAACATATAAGGAAATAGGGCTCCTCACATGCGAAGCCACAGTCAACGGGCACCTCTA
CAAAACTAATTACCTGACCCATCGACAGACAAATACCATCATTGATGTGGTTCTGAGTCC
ATCTCATGGAATAGAGTTGAGTGTAGGGGAGAAGCTTGTTCTCAATTGCACAGCTAGAAC
CGAGTTGAACGTGGGTATCGATTTTAACTGGGAATACCCATCTAGTAAGCACCAACACAA
AAAACTTGTCAATCGAGATTTGAAAACTCAATCTGGTAGCGAGATGAAAAAGTTCCTGTC
AACTCTTACAATCGATGGCGTGACCCGGAGTGATCAAGGATTGTATACCTGCGCCGCCA
GCTCTGGCCTGATGACTAAAAAGAACAGCACCTTTGTACGAGTGCATGAAAAGGATAAG
ACTCATACATGCCCTCCTTGTCCCGCTCCAGAGCTGCTGGGAGGTCCCAGTGTTTTCCTC
TTCCCACCAAAGCCCAAAGATACTCTGATGATTAGCCGGACCCCTGAGGTGACTTGCGT
CGTGGTGGATGTTTCACATGAAGATCCAGAAGTGAAGTTCAATTGGTACGTTGATGGTGT
GGAGGTACACAATGCCAAGACTAAACCTCGGGAGGAACAGTATAACAGCACTTACAGA
GTTGTCAGCGTACTCACAGTGCTTCATCAGGACTGGTTGAATGGTAAGGAGTATAAGTGC
AAAGTGAGTAATAAGGCTCTGCCAGCACCCATAGAGAAGACAATCTCAAAGGCCAAAGG
CCAGCCCCGAGAACCACAAGTATACACACTGCCACCTAGTAGAGACGAGTTGACAAAAA
ATCAGGTCAGCCTCACCTGTCTCGTGAAAGGCTTCTACCCTAGCGACATTGCCGTAGAAT
GGGAAAGCAACGGGCAACCAGAAAACAATTATAAGACAACACCTCCCGTTCTCGATAGT
GACGGAAGTTTCTTCCTGTATAGCAAACTTACCGTGGATAAATCAAGATGGCAGCAAGGT
AATGTGTTTAGCTGTTCAGTAATGCACGAAGCTCTGCATAACCACTACACCCAAAAATCT
TTGTCTCTGTCTCCAGGGTGAGCGGCCGCATCGGCTAGCXAAGCTTCCTGCAGGAGTCGG
TCGACTAGAGCTCGCTGATCAGCCTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGCTGGGGAGAGATC
TAGGAACCCCTAGTGATGGAGTTGGCCACTCCCTCTCTGCGCGCTCGCTCGCTCACTGAG
GCCGCCCGGGCAAAGCCCGGGCGTCGGGCGACCTTTGGTCGCCCGGCCTCAGTGAGCG
AGCGAGCGCGCAGAGAGGGAGTGGCCAACC (bold sequence: SEQ ID NO:20)

X = positions for SLIM regulatory elements (see FIGS. 18-19)

FIG. 18A

SLIM SEQUENCES

6S-Folinic Acid-responsive miRNA Switches (Eylea CDS target)

6s-Folinic Acid Aptamer siRNA #1

Complementary Strand

SLIM switch for Target 1 (SEQ ID NO:21)

GAACGCCTCCTAACGTCTGGTCACGACCCTGCGTGAGCGACCCCATTGTTCAGGTTTGTA
TTCTTTTGGCCACTGACTGAGAATACAAATGAACAATGGGGGCGCCTACGCAGCCCCTCG
AAATCACGAGGGAGACGAGATAAGGGGGCGTTT

SLIM switch for Target 2 (SEQ ID NO:22)

GAACGCCTCCTAACGTCTGGTCACGACCCTGCGTGAGCGACCCTGAGTTCCTTCCCTAAA
TACTTTTGGCCACTGACTGAGTATTTAGGAGGAACTCAGGGGGGCGCCTACGCAGCCCC
TCGAAATCACGAGGGAGACGAGATAAGGGGGCGTTT

SLIM switch for Target 3 (SEQ ID NO:23)

GAACGCCTCCTAACGTCTGGTCACGACCCTGCGTGAGCGACCAAGAGTTAACGTGTCGA
TCTCTTTTGGCCACTGACTGAGAGATCGACGTTAACTCTTGGGGGCGCCTACGCAGCCCC
TCGAAATCACGAGGGAGACGAGATAAGGGGGCGTTT

SLIM switch for Target 4 (SEQ ID NO:24)

GAACGCCTCCTAACGTCTGGTCACGACCCTGCGTGAGCGACCCTTCCCTAAATAGTATAG
ATCTTTTGGCCACTGACTGAGATCTATACTTTAGGGAAGGGGGGCGCCTACGCAGCCCCT
CGAAATCACGAGGGAGACGAGATAAGGGGGCGTTT

SLIM switch for Target 5 (SEQ ID NO:25)

GAACGCCTCCTAACGTCTGGTCACGACCCTGCGTGAGCGACCGTGTCGATCTTGGCTCA
ACTCTTTTGGCCACTGACTGAGCGTGTCGATTGGCTCAACTGGGGCGCCTACGCAGCCCC
TCGAAATCACGAGGGAGACGAGATAAGGGGGCGTTT

Theophylline-responsive miRNA Switches (Eylea CDS target)

Theophylline Aptamer siRNA #1

Complementary Strand

SLIM switch for Target 1 (SEQ ID NO:26)

GAACGCCTCCTTGATACCAGCTGCGTGAGCGACCCCATTGTTCAGGTTTGTATTCTTTTGG
CCACTGACTGAGAATACAAATGAACAATGGGGGCGCCTACGCGCCCTTGGCAGCAAGGG
GGCGTTT

SLIM switch for Target 2 ((SEQ ID NO:27)

GAACGCCTCCTTGATACCAGCTGCGTGAGCGACCCTGAGTTCCTTCCCTAAATACTTTTG
GCCACTGACTGAGTATTTAGGAGGAACTCAGGGGGGCGCCTACGCGCCCTTGGCAGCAA
GGGGGCGTTT

FIG. 18B

SLIM switch for Target 3 ((SEQ ID NO:28)
GAACGCCTCCTTGATACCAGCTGCGTGAGCGACCAAGAGTTAACGTGTCGATCTCTTTTG
GCCACTGACTGAGAGATCGACGTTAACTCTTGGGGGCGCCTACGCGCCCTTGGCAGCAA
GGGGGCGTTT

SLIM switch for Target 4 (SEQ ID NO:29)
GAACGCCTCCTTGATACCAGCTGCGTGAGCGACCCTTCCCTAAATAGTATAGATCTTTTG
GCCACTGACTGAGATCTATACTTTAGGGAAGGGGGGCGCCTACGCGCCCTTGGCAGCAA
GGGGGCGTTT

SLIM switch for Target 5 (SEQ ID NO:30)
GAACGCCTCCTTGATACCAGCTGCGTGAGCGACCGTGTCGATCTTGGCTCAACTCTTTTG
GCCACTGACTGAGCGTGTCGATTGGCTCAACTGGGGCGCCTACGCGCCCTTGGCAGCAA
GGGGGCGTTT

Tetracycline-responsive miRNA Switches (Eylea CDS target)
Tetracycline Aptamer
siRNA #1
Complementary Strand

SLIM switch for Target 1 (SEQ ID NO:31)
GAACGCCTCCTAGAGGTGAAGAATACGACCACCTTGCGTGAGCGACCCCATTGTTCAGG
TTTGTATTCTTTTGGCCACTGACTGAGAATACAAATGAACAATGGGGGCGCCTACGCAGG
CTCGAAAGAGCCTAAAACATAAGGGGGCGTTT

SLIM switch for Target 2 ((SEQ ID NO:32)
GAACGCCTCCTAGAGGTGAAGAATACGACCACCTTGCGTGAGCGACCCTGAGTTCCTTC
CCTAAATACTTTTGGCCACTGACTGAGTATTTAGGAGGAACTCAGGGGGGCGCCTACGCA
GGCTCGAAAGAGCCTAAAACATAAGGGGGCGTTT

SLIM switch for Target 3 (SEQ ID NO:33)
GAACGCCTCCTAGAGGTGAAGAATACGACCACCTTGCGTGAGCGACCAAGAGTTAACGT
GTCGATCTCTTTTGGCCACTGACTGAGAGATCGACGTTAACTCTTGGGGGCGCCTACGCA
GGCTCGAAAGAGCCTAAAACATAAGGGGGCGTTT

SLIM switch for Target 4 (SEQ ID NO:34)
GAACGCCTCCTAGAGGTGAAGAATACGACCACCTTGCGTGAGCGACCCTTCCCTAAATA
GTATAGATCTTTTGGCCACTGACTGAGATCTATACTTTAGGGAAGGGGGGCGCCTACGCA
GGCTCGAAAGAGCCTAAAACATAAGGGGGCGTTT

SLIM switch for Target 5 (SEQ ID NO:35)
GAACGCCTCCTAGAGGTGAAGAATACGACCACCTTGCGTGAGCGACCGTGTCGATCTTG
GCTCAACTCTTTTGGCCACTGACTGAGCGTGTCGATTGGCTCAACTGGGGCGCCTACGCA
GGCTCGAAAGAGCCTAAAACATAAGGGGGCGTTT Eylea Target 1: TATTTAGGGAAGGAACTCAGG (SEQ ID NO:70)
Eylea Target 2: AATACAAACCTGAACAATGGG (SEQ ID NO:71)
Eylea Target 3: AGTTGAGCCAAGATCGACACG (SEQ ID NO:72)
Eylea Target 4: ATCTATACTATTTAGGGAAGG (SEQ ID NO:73)
Eylea Target 5: AGATCGACACGTTAACTCTTG (SEQ ID NO:74)

FIG. 18C

*Soluble fms-like tyrosine kinase 1 (sFLT1) VEGF inhibitor cDNA* (SEQ ID NO:36)

XATGGTCAGCTACTGGGACACCGGGGTCCTGCTGTGCGCGCTGCTCAGCTGTCTGCTTC
TCACAGGATCTAGTTCAGGTTCAAAATTAAAAGATCCTGAACTGAGTTTAAAAGGCACCC
AGCACATCATGCAAGCAGGCCAGACACTGCATCTCCAATGCAGGGGGGAAGCAGCCCA
TAAATGGTCTTTGCCTGAAATGGTGAGTAAGGAAAGCGAAAGGCTGAGCATAACTAAAT
CTGCCTGTGGAAGAAATGGCAAACAATTCTGCAGTACTTTAACCTTGAACACAGCTCAAG
CAAACCACACTGGCTTCTACAGCTGCAAATATCTAGCTGTACCTACTTCAAAGAAGAAGG
AAACAGAATCTGCAATCTATATATTTATTAGTGATACAGGTAGACCTTTCGTAGAGATGTA
CAGTGAAATCCCCGAAATTATACACATGACTGAAGGAAGGGAGCTCGTCATTCCCTGCC
GGGTTACGTCACCTAACATCACTGTTACTTTAAAAAAGTTTCCACTTGACACTTTGATCCC
TGATGGAAAACGCATAATCTGGGACAGTAGAAAGGGCTTCATCATATCAAATGCAACGT
ACAAAGAAATAGGGCTTCTGACCTGTGAAGCAACAGTCAATGGGCATTTGTATAAGACA
AACTATCTCACACATCGACAAACCAATACAATCATAGATGTCCAAATAAGCACACCACGC
CCAGTCAAATTACTTAGAGGCCATACTCTTGTCCTCAATTGTACTGCTACCACTCCCTTGA
ACACGAGAGTTCAAATGACCTGGAGTTACCCTGATGAAAAAAATAAGAGAGCTTCCGTA
AGGCGACGAATTGACCAAAGCAATTCCCATGCCAACATATTCTACAGTGTTCTTACTATT
GACAAAATGCAGAACAAAGACAAAGGACTTTATACTTGTCGTGTAAGGAGTGGACCATC
ATTCAAATCTGTTAACACCTCAGTGCATATATATGATAAAGCATTCATCACTGTGAAACAT
CGAAAACAGCAGGTGCTTGAAACCGTAGCTGGCAAGCGGTCTTACCGGCTCTCTATGAA
AGTGAAGGCATTTCCCTCGCCGGAAGTTGTATGGTTAAAAGATGGGTTACCTGCGACTG
AGAAATCTGCTCGCTATTTGACTCGTGGCTACTCGTTAATTATCAAGGACGTAACTGAAG
AGGATGCAGGGAATTATACAATCTTGCTGAGCATAAAACAGTCAAATGTGTTTAAAAACC
TCACTGCCACTCTAATTGTCAATGTGAAACCCCAGATTTACGAAAAGGCCGTGTCATCGT
TTCCAGACCCGGCTCTCTACCCACTGGGCAGCAGACAAATCCTGACTTGTACCGCATAT
GGTATCCCTCAACCTACAATCAAGTGGTTCTGGCACCCCTGTAACCATAATCATTCCGAA
GCAAGGTGTGACTTTTGTTCCAATAATGAAGAGTCCTTTATCCTGGATGCTGACAGCAAC
ATGGGAAACAGAATTGAGAGCATCACTCAGCGCATGGCAATAATAGAAGGAAAGAATAA
GATGGCTAGCACCTTGGTTGTGGCTGACTCTAGAATTTCTGGAATCTACATTTGCATAGC
TTCCAATAAAGTTGGGACTGTGGGAAGAAACATAAGCTTTTATATCACAGATGTGCCAAA
TGGGTTTCATGTTAACTTGGAAAAAATGCCGACGGAAGGAGAGGACCTGAAACTGTCTT
GCACAGTTAACAAGTTCTTATACAGAGACGTTACTTGGATTTTACTGCGGACAGTTAATA
ACAGAACAATGCACTACAGTATTAGCAAGCAAAAAATGGCCATCACTAAGGAGCACTCC
ATCACTCTTAATCTTACCATCATGAATGTTTCCCTGCAAGATTCAGGCACCTATGCCTGCA
GAGCCAGGAATGTATACACAGGGGAAGAAATCCTCCAGAAGAAAGAAATTACAATCAGA
GGTGAGCACTGCAACAAAAAGGCTGTTTTCTCTCGGATCTCCAAATTTAAAAGCACAAGG
AATGATTGTACCACACAAAGTAATGTAAAACATTAAAAACAAACAAAX

X = positions for SLIM regulatory elements (see below)

FIG. 19A

SLIM SEQUENCES

6S-Folinic Acid-responsive miRNA Switches (sFLT1 CDS target)

6S-Folinic Acid Aptamer siRNA #1

Complementary Strand

SLIM riboswitch for sFLT1 Target 1 (SEQ ID NO:37)

GAACGCCTCCTAACGTCTGGTCACGACCCTGCGTGAGCGACCAGACGAAGAGTGTCCTAGATCTTTTGGCCACTGACTGAGATCTAGGACTCTTCGTCTGGGGGCGCCTACGCAGCCCCTCGAAATCACGAGGGAGACGAGATAAGGGGGCGTTT

SLIM riboswitch for sFLT1 Target 2 (SEQ ID NO:38)

GAACGCCTCCTAACGTCTGGTCACGACCCTGCGTGAGCGACCGCTTTCCGACTCGTATTGATCTTTTGGCCACTGACTGAGATCAATACGTCGGAAAGCGGGGGCGCCTACGCAGCCCCTCGAAATCACGAGGGAGACGAGATAAGGGGGCGTTT

SLIM riboswitch for sFLT1 Target 3 (SEQ ID NO:39)

GAACGCCTCCTAACGTCTGGTCACGACCCTGCGTGAGCGACCACCTTCTTTACCGTTTGTTACTTTTGGCCACTGACTGAGTAACAAACTAAAGAAGGTGGGGGCGCCTACGCAGCCCCTCGAAATCACGAGGGAGACGAGATAAGGGGGCGTTT

SLIM riboswitch for sFLT1 Target 4 (SEQ ID NO:40)

GAACGCCTCCTAACGTCTGGTCACGACCCTGCGTGAGCGACCCGTTTGTTAAGACGTCATGACTTTTGGCCACTGACTGAGTCATGACGTTAACAAACGGGGGGCGCCTACGCAGCCCCTCGAAATCACGAGGGAGACGAGATAAGGGGGCGTTT

SLIM riboswitch for sFLT1 Target 5 (SEQ ID NO:41)

GAACGCCTCCTAACGTCTGGTCACGACCCTGCGTGAGCGACGCAAATATCTAGCTGTACCTACTTTTGGCCACTGACTGAGTAGGTACATAGATATTTGCGGGGCGCCTACGCAGCCCCTCGAAATCACGAGGGAGACGAGATAAGGGGGCGTTT

Theophylline-responsive miRNA Switches (sFLT1 CDS target)

Theophylline Aptamer siRNA #1

Complementary Strand

SLIM riboswitch for sFLT1 Target 1 (SEQ ID NO:42)

GAACGCCTCCTTGATACCAGCTGCGTGAGCGACCAGACGAAGAGTGTCCTAGATCTTTTGGCCACTGACTGAGATCTAGGACTCTTCGTCTGGGGGCGCCTACGCGCCCTTGGCAGCAAGGGGGCGTTT

SLIM riboswitch for sFLT1 Target 2 (SEQ ID NO:43)

GAACGCCTCCTTGATACCAGCTGCGTGAGCGACCGCTTTCCGACTCGTATTGATCTTTTGGCCACTGACTGAGATCAATACGTCGGAAAGCGGGGGCGCCTACGCGCCCTTGGCAGCAAGGGGGCGTTT

FIG. 19B

SLIM riboswitch for sFLT1 Target 3 (SEQ ID NO:44)
GAACGCCTCCTTGATACCAGCTGCGTGAGCGACCACCTTCTTTACCGTTTGTTACTTTTGG
CCACTGACTGAGTAACAAACTAAAGAAGGTGGGGGCGCCTACGCGCCCTTGGCAGCAAG
GGGGCGTTT

SLIM riboswitch for sFLT1 Target 4 (SEQ ID NO:45)
GAACGCCTCCTTGATACCAGCTGCGTGAGCGACCCGTTTGTTAAGACGTCATGACTTTTG
GCCACTGACTGAGTCATGACGTTAACAAACGGGGGGCGCCTACGCGCCCTTGGCAGCAA
GGGGGCGTTT

SLIM riboswitch for sFLT1 Target 5 (SEQ ID NO:46)
GAACGCCTCCTTGATACCAGCTGCGTGAGCGACGCAAATATCTAGCTGTACCTACTTTTG
GCCACTGACTGAGTAGGTACATAGATATTTGCGGGGCGCCTACGCGCCCTTGGCAGCAA
GGGGGCGTTT

Tetracycline-responsive miRNA Switches (sFLT1 CDS target)

Tetracycline Aptamer
siRNA #1
Complementary Strand

SLIM riboswitch for sFLT1 Target 1 (SEQ ID NO:47)
GAACGCCTCCTAGAGGTGAAGAATACGACCACCTTGCGTGAGCGACCAGACGAAGAGTG
TCCTAGATCTTTTGGCCACTGACTGAGATCTAGGACTCTTCGTCTGGGGGCGCCTACGCA
GGCTCGAAAGAGCCTAAAACATAAGGGGGCGTTT

SLIM riboswitch for sFLT1 Target 2 (SEQ ID NO:48)
GAACGCCTCCTAGAGGTGAAGAATACGACCACCTTGCGTGAGCGACCGCTTTCCGACTC
GTATTGATCTTTTGGCCACTGACTGAGATCAATACGTCGGAAAGCGGGGGCGCCTACGC
AGGCTCGAAAGAGCCTAAAACATAAGGGGGCGTTT

SLIM riboswitch for sFLT1 Target 3 (SEQ ID NO:49)
GAACGCCTCCTAGAGGTGAAGAATACGACCACCTTGCGTGAGCGACCACCTTCTTTACC
GTTTGTTACTTTTGGCCACTGACTGAGTAACAAACTAAAGAAGGTGGGGGCGCCTACGCA
GGCTCGAAAGAGCCTAAAACATAAGGGGGCGTTT

SLIM riboswitch for sFLT1 Target 4 (SEQ ID NO:50)
GAACGCCTCCTAGAGGTGAAGAATACGACCACCTTGCGTGAGCGACCCGTTTGTTAAGA
CGTCATGACTTTTGGCCACTGACTGAGTCATGACGTTAACAAACGGGGGGCGCCTACGC
AGGCTCGAAAGAGCCTAAAACATAAGGGGGCGTTT

SLIM riboswitch for sFLT1 Target 5 (SEQ ID NO:51)
GAACGCCTCCTAGAGGTGAAGAATACGACCACCTTGCGTGAGCGACGCAAATATCTAGC
TGTACCTACTTTTGGCCACTGACTGAGTAGGTACATAGATATTTGCGGGGCGCCTACGCA
GGCTCGAAAGAGCCTAAAACATA sFLT1 Target 1: TAGGTACAGCTAGATATTTGC (SEQ ID NO:75)
sFLT1 Target 2: TCATGACGTCTTAACAAACGG (SEQ ID NO:76)
sFLT1 Target 3: TAACAAACGGTAAAGAAGGTG (SEQ ID NO:77)
sFLT1 Target 4: ATCAATACGAGTCGGAAAGCG (SEQ ID NO:78)
sFLT1 Target 5: ATCTAGGACACTCTTCGTCTG (SEQ ID NO: 79)

FIG. 23A

SEQUENCES

Codon Optimized PTGS2 (SEQ ID NO:52)

ATGCTTGCCCGGGCCCTGCTTCTGTGTGCGGTATTGGCACTGAGTCACACAGCCAACCCG
TGCTGCTCACACCCATGTCAGAATCGGGGAGTTTGCATGTCAGTAGGGTTTGACCAATATA
AGTGCGACTGTACCCGGACAGGCTTTTATGGAGAAAATTGTTCTACACCCGAATTTTTGAC
GAGGATTAAGCTCTTTCTGAAGCCTACACCAAATACAGTCCATTATATCCTCACGCACTTCA
AGGGTTTTTGGAATGTCGTAAACAACATTCCGTTTCTGAGAAATGCGATAATGTCTTACGTC
CTTACATCCCGGAGCCACCTTATTGACTCACCCCCAACATACAACGCCGACTACGGATACA
AAAGTTGGGAAGCTTTCTCCAACCTGTCTTACTACACGCGAGCATTGCCTCCTGTACCCGA
CGATTGCCCGACGCCGTTGGGGGTGAAAGGAAAAAGCAGCTCCCGGACTCAAACGAAAT
AGTAGAGAAATTGTTGCTTCGCCGAAAATTTATACCAGACCCGCAGGGTAGCAATATGATG
TTTGCGTTCTTCGCTCAGCACTTCACTCACCAATTCTTTAAGACAGACCACAAGAGAGGTC
CCGCATTCACGAATGGCCTTGGACACGGCGTCGACTTGAACCACATATATGGGGAGACAT
TGGCCAGACAAAGGAAACTTCGATTGTTTAAGGATGGGAAAATGAAATACCAAATTATTGAT
GGCGAGATGTATCCTCCAACAGTGAAGGATACGCAAGCGGAGATGATTTATCCACCGCAG
GTACCAGAGCATTTGCGGTTCGCGGTGGGGCAGGAAGTATTTGGACTTGTTCCCGGTCTG
ATGATGTACGCCACAATATGGCTCCGGGAGCATAATCGCGTGTGTGACGTACTTAAGCAAG
AGCACCCGGAATGGGGCGACGAGCAACTTTTTCAAACGAGTCGACTGATTCTCATTGGGG
AAACGATTAAAATAGTGATCGAAGATTATGTGCAACATCTTTCTGGTTACCACTTTAAGTTG
AAGTTCGATCCTGAGCTGCTTTTCAATAAACAATTCCAGTATCAAAACAGAATCGCCGCGG
AGTTCAACACGCTGTATCATTGGCATCCCCTGTTGCCCGATACTTTTCAAATCCATGACCAG
AAATACAATTACCAGCAATTTATATATAATAACTCTATCCTCCTGGAGCATGGCATTACACAA
TTCGTTGAAAGTTTCACAAGGCAGATCGCAGGAAGAGTTGCGGGTGGCCGGAATGTGCCG
CCTGCCGTGCAAAAGGTATCACAGGCTAGCATCGACCAATCAAGGCAAATGAAGTACCAG
TCTTTTAATGAGTACAGGAAAAGGTTCATGCTGAAGCCTTACGAGAGCTTTGAAGAACTGA
CGGGCGAAAAGGAAATGTCCGCGGAACTGGAAGCGTTGTACGGAGATATTGATGCGGTAG
AGCTCTACCCCGCGCTTCTGGTCGAAAAGCCCCGGCCAGATGCCATTTTCGGGGAAACCA
TGGTTGAAGTGGGCGCCCCATTCAGTTTGAAAGGTCTGATGGGTAATGTAATTTGCAGTCC
GGCGTACTGGAAGCCTTCCACTTTTGGTGGGGAAGTGGGGTTTCAAATTATCAATACGGCC
TCAATTCAGTCTCTGATTTGTAACAATGTTAAGGGATGTCCCTTTACATCTTTTAGTGTACCG
GACCCCGAGCTTATTAAGACCGTGACCATAAATGCTTCAAGCTCTAGAAGTGGTCTTGATG
ATATCAACCCCACAGTTTTGCTTAAGGAAAGGAGCACGGAGCTCTAA

FIG. 23B

Codon Optimized PTGFR (SEQ ID NO:53)

ATGAGCATGAACAACTCAAAACAGTTGGTCTCCCCAGCAGCGGCCCTTTTGTCCAACACAA
CGTGTCAGACTGAGAATAGACTCAGTGTATTTTTTAGCGTGATTTTTATGACCGTCGGTATC
CTGTCTAACTCTCTTGCCATAGCAATATTGATGAAAGCCTATCAGCGATTCCGGCAAAAGTC
TAAGGCGTCATTTTTGTTGTTGGCAAGCGGGCTTGTCATCACGGACTTTTTCGGGCACCTC
ATTAACGGAGCCATAGCCGTGTTCGTTTATGCTTCAGACAAAGAGTGGATACGATTCGATC
AGAGCAATGTGCTTTGCAGTATCTTTGGCATATGTATGGTGTTTAGTGGATTGTGTCCACTC
TTGCTTGGGAGCGTGATGGCTATTGAAAGATGCATCGGGGTGACTAAACCTATCTTTCACA
GTACCAAAATTACATCTAAGCACGTCAAGATGATGTTGTCCGGGGTGTGTCTTTTTGCTGTC
TTTATTGCGTTGTTGCCAATACTGGGCCACAGGGACTACAAAATTCAGGCCTCACGCACTT
GGTGCTTCTATAACACTGAGGATATTAAAGACTGGGAGGATAGGTTTTATCTTCTTCTTTTC
TCATTCCTCGGTCTGCTCGCACTGGGGGTATCCCTTTTGTGTAACGCTATCACAGGTATCA
CCTTGTTGCGCGTTAAATTTAAGAGCCAACAGCATCGCCAGGGGAGGTCACATCACCTCG
AAATGGTAATACAGTTGCTCGCGATCATGTGTGTTAGTTGTATCTGCTGGTCACCCTTCTTG
GGATATAGAATAATTCTGAATGGAAAAGAAAAGTACAAAGTCTATGAAGAACAGAGCGATTT
TCTGCATCGATTGCAATGGCCCACTTTGGAATAA

PTGS2-P2A-PTGFR (SEQ ID NO:54)

PTGS2: Bold (SEQ ID NO:55)

*P2A: Italicized* (SEQ ID NO:56)

PTGFR: Underlined (SEQ ID NO:57)

**XATGCTTGCCCGGGCCCTGCTTCTGTGTGCGGTATTGGCACTGAGTCACACAGCCAACC
CGTGCTGCTCACACCCATGTCAGAATCGGGGAGTTTGCATGTCAGTAGGGTTTGACCAAT
ATAAGTGCGACTGTACCCGGACAGGCTTTTATGGAGAAAATTGTTCTACACCCGAATTTT
TGACGAGGATTAAGCTCTTTCTGAAGCCTACACCAAATACAGTCCATTATATCCTCACGC
ACTTCAAGGGTTTTTGGAATGTCGTAAACAACATTCCGTTTCTGAGAAATGCGATAATGT
CTTACGTCCTTACATCCCGGAGCCACCTTATTGACTCACCCCCAACATACAACGCCGACT
ACGGATACAAAAGTTGGGAAGCTTTCTCCAACCTGTCTTACTACACGCGAGCATTGCCTC
CTGTACCCGACGATTGCCCGACGCCGTTGGGGGTGAAAGGAAAAAAGCAGCTCCCGGA
CTCAAACGAAATAGTAGAGAAATTGTTGCTTCGCCGAAAATTTATACCAGACCCGCAGG
GTAGCAATATGATGTTTGCGTTCTTCGCTCAGCACTTCACTCACCAATTCTTTAAGACAGA
CCACAAGAGAGGTCCCGCATTCACGAATGGCCTTGGACACGGCGTCGACTTGAACCACA
TATATGGGGAGACATTGGCCAGACAAAGGAAACTTCGATTGTTTAAGGATGGGAAAATG
AAATACCAAATTATTGATGGCGAGATGTATCCTCCAACAGTGAAGGATACGCAAGCGGA
GATGATTTATCCACCGCAGGTACCAGAGCATTTGCGGTTCGCGGTGGGGCAGGAAGTAT
TTGGACTTGTTCCCGGTCTGATGATGTACGCCACAATATGGCTCCGGGAGCATAATCGCG
TGTGTGACGTACTTAAGCAAGAGCACCCGGAATGGGGCGACGAGCAACTTTTTCAAACG
AGTCGACTGATTCTCATTGGGGAAACGATTAAAATAGTGATCGAAGATTATGTGCAACAT
CTTTCTGGTTACCACTTTAAGTTGAAGTTCGATCCTGAGCTGCTTTTCAATAAACAATTCC
AGTATCAAAACAGAATCGCCGCGGAGTTCAACACGCTGTATCATTGGCATCCCCTGTTGC
CCGATACTTTTCAAATCCATGACCAGAAATACAATTACCAGCAATTTATATATAATAACTC**

FIG. 23C

TATCCTCCTGGAGCATGGCATTACACAATTCGTTGAAAGTTTCACAAGGCAGATCGCAGG
AAGAGTTGCGGGTGGCCGGAATGTGCCGCCTGCCGTGCAAAAGGTATCACAGGCTAGC
ATCGACCAATCAAGGCAAATGAAGTACCAGTCTTTTAATGAGTACAGGAAAAGGTTCATG
CTGAAGCCTTACGAGAGCTTTGAAGAACTGACGGGCGAAAAGGAAATGTCCGCGGAACT
GGAAGCGTTGTACGGAGATATTGATGCGGTAGAGCTCTACCCCGCGCTTCTGGTCGAAA
AGCCCCGGCCAGATGCCATTTTCGGGGAAACCATGGTTGAAGTGGGCGCCCCATTCAGT
TTGAAAGGTCTGATGGGTAATGTAATTTGCAGTCCGGCGTACTGGAAGCCTTCCACTTTT
GGTGGGGAAGTGGGGTTTCAAATTATCAATACGGCCTCAATTCAGTCTCTGATTTGTAAC
AATGTTAAGGGATGTCCCTTTACATCTTTTAGTGTACCGGACCCCGAGCTTATTAAGACC
GTGACCATAAATGCTTCAAGCTCTAGAAGTGGTCTTGATGATATCAACCCCACAGTTTTG
CTTAAGGAAAGGAGCACGGAGCTCGGAAGCGGA*GCTACTAACTTCAGCCTGCTGAAGCA*
*GGCTGGAGACGTCGAGGAGAACCCTGGACCT*AGCATGAACAACTCAAAACAGTTGGTCTC
CCCAGCAGCGGCCCTTTTGTCCAACACAACGTGTCAGACTGAGAATAGACTCAGTGTATTT
TTTAGCGTGATTTTTATGACCGTCGGTATCCTGTCTAACTCTCTTGCCATAGCAATATTGAT
GAAAGCCTATCAGCGATTCCGGCAAAAGTCTAAGGCGTCATTTTTGTTGTTGGCAAGCGGG
CTTGTCATCACGGACTTTTTCGGGCACCTCATTAACGGAGCCATAGCCGTGTTCGTTTATG
CTTCAGACAAAGAGTGGATACGATTCGATCAGAGCAATGTGCTTTGCAGTATCTTTGGCAT
ATGTATGGTGTTTAGTGGATTGTGTCCACTCTTGCTTGGGAGCGTGATGGCTATTGAAAGA
TGCATCGGGGTGACTAAACCTATCTTTCACAGTACCAAAATTACATCTAAGCACGTCAAGAT
GATGTTGTCCGGGGTGTGTCTTTTTGCTGTCTTTATTGCGTTGTTGCCAATACTGGGCCAC
AGGGACTACAAAATTCAGGCCTCACGCACTTGGTGCTTCTATAACACTGAGGATATTAAAG
ACTGGGAGGATAGGTTTTATCTTCTTCTTTTCTCATTCCTCGGTCTGCTCGCACTGGGGGT
ATCCCTTTTGTGTAACGCTATCACAGGTATCACCTTGTTGCGCGTTAAATTTAAGAGCCAAC
AGCATCGCCAGGGGAGGTCACATCACCTCGAAATGGTAATACAGTTGCTCGCGATCATGT
GTGTTAGTTGTATCTGCTGGTCACCCTTCTTGGGATATAGAATAATTCTGAATGGAAAAGAA
AAGTACAAAGTCTATGAAGAACAGAGCGATTTTCTGCATCGATTGCAATGGCCCACTTTGG
AATAAX

X- locations for the SLIM riboswitches or target sequences

Complete AAV expression cassette for PGF2alpha biosynthesis(SEQ ID NO:58)

*TC40: Underlined and Italicized* (SEQ ID NO:59)

PTGS2: Bold (SEQ ID NO:60)

*P2A: Italicized* (SEQ ID NO:61)

PTGFR: Underlined (SEQ ID NO:62)

*TC45: Bold and Italicized* (SEQ ID NO:63)

GGTTGGCCACTCCCTCTCTGCGCGCTCGCTCGCTCACTGAGGCCGGGCGACCAAAGGTC
GCCCGACGCCCGGGCTTTGCCCGGGCGGCCTCAGTGAGCGAGCGAGCGCGCAGAGAGG
GAGTGGCCAACTCCATCACTAGGGGTTCCTAGATCTGAATTCGGTACCCCTAGTTATTAAT
AGTAATCAATTACGGGGTCATTAGTTCATAGCCCATATATGGAGTTCCGCGTTACATAACTT
ACGGTAAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGGACTATT
TACGGTAAACTGCCCACTTGGCAGTACATCAAGTGTATCATATGCCAAGTACGCCCCCTAT

FIG. 23D

TGACGTCAATGACGGTAAATGGCCCGCCTGGCATTATGCCCAGTACATGACCTTATGGGACTTTCCT
ACTTGGCAGTACATCTACGTATTAGTCATCGCTATTACCATGGTCGAGGTGAGCCCCACGTTCTGCT
TCACTCTCCCCATCTCCCCCCCCTCCCCACCCCCAATTTTGTATTTATTTATTTTTTAATTATTTTGTGC
AGCGATGGGGGCGGGGGGGGGGGGGGGGCGCGCGCCAGGCGGGGCGGGGCGGGGCGAGGGG
CGGGGCGGGGCGAGGCGGAGAGGTGCGGCGGCAGCCAATCAGAGCGGCGCGCTCCGAAAGTTTC
CTTTTATGGCGAGGCGGCGGCGGCGGCGGCCCTATAAAAAGCGAAGCGCGCGGCGGGCGGGAGT
CGCTGCGACGCTGCCTTCGCCCCGTGCCCCGCTCCGCCGCCGCCTCGCGCCGCCCGCCCCGGCT
CTGACTGACCGCGTTACTCCCACAGGTGAGCGGGCGGGACGGCCCTTCTCCTCCGGGCTGTAATTA
GCGCTTGGTTTAATGACGGCTTGTTTCTTTTCTGTGGCTGCGTGAAAGCCTTGAGGGGCTCCGGGA
GCTAGAGCCTCTGCTAACCATGTTCATGCCTTCTTCTTTTTCCTACAGCTCCTGGGCAACGTGCTGGT
TATTGTGCTGTCTCATCATTTTGGCAAAGAATTCCTCGAAGATCTAGGCAACTCGAGAAACAAACAAA
*CTGAGGTGCAGGTACATCCAGCTGACGAGTCCCAAATAGGACGAAAGGGAGAGGTGAAGAATACGA*
*CCACCTAGGCTCGAAAGAGCCTAAAACATACCTTCCTGGATTCCACTGCTATCCAC*AAAAAGAAAAAT
AAAAAGCCACCATGCTTGCCCGGGCCCTGCTTCTGTGTGCGGTATTGGCACTGAGTCACACAGCCA
ACCCGTGCTGCTCACACCCATGTCAGAATCGGGGAGTTTGCATGTCAGTAGGGTTTGACCAATATA
AGTGCGACTGTACCCGGACAGGCTTTTATGGAGAAAATTGTTCTACACCCGAATTTTTGACGAGGA
TTAAGCTCTTTCTGAAGCCTACACCAAATACAGTCCATTATATCCTCACGCACTTCAAGGGTTTTTG
GAATGTCGTAAACAACATTCCGTTTCTGAGAAATGCGATAATGTCTTACGTCCTTACATCCCGGAG
CCACCTTATTGACTCACCCCCAACATACAACGCCGACTACGGATACAAAAGTTGGGAAGCTTTCTC
CAACCTGTCTTACTACACGCGAGCATTGCCTCCTGTACCCGACGATTGCCCGACGCCGTTGGGGG
TGAAAGGAAAAAAGCAGCTCCCGGACTCAAACGAAATAGTAGAGAAATTGTTGCTTCGCCGAAAA
TTTATACCAGACCCGCAGGGTAGCAATATGATGTTTGCGTTCTTCGCTCAGCACTTCACTCACCAA
TTCTTTAAGACAGACCACAAGAGAGGTCCCGCATTCACGAATGGCCTTGGACACGGCGTCGACTT
GAACCACATATATGGGGAGACATTGGCCAGACAAAGGAAACTTCGATTGTTTAAGGATGGGAAAA
TGAAATACCAAATTATTGATGGCGAGATGTATCCTCCAACAGTGAAGGATACGCAAGCGGAGATG
ATTTATCCACCGCAGGTACCAGAGCATTTGCGGTTCGCGGTGGGGCAGGAAGTATTTGGACTTGTT
CCCGGTCTGATGATGTACGCCACAATATGGCTCCGGGAGCATAATCGCGTGTGTGACGTACTTAA
GCAAGAGCACCCGGAATGGGGCGACGAGCAACTTTTTCAAACGAGTCGACTGATTCTCATTGGGG
AAACGATTAAAATAGTGATCGAAGATTATGTGCAACATCTTTCTGGTTACCACTTTAAGTTGAAGTT
CGATCCTGAGCTGCTTTTCAATAAACAATTCCAGTATCAAAACAGAATCGCCGCGGAGTTCAACAC
GCTGTATCATTGGCATCCCCTGTTGCCCGATACTTTTCAAATCCATGACCAGAAATACAATTACCA
GCAATTTATATATAATAACTCTATCCTCCTGGAGCATGGCATTACACAATTCGTTGAAAGTTTCACA
AGGCAGATCGCAGGAAGAGTTGCGGGTGGCCGGAATGTGCCGCCTGCCGTGCAAAAGGTATCAC
AGGCTAGCATCGACCAATCAAGGCAAATGAAGTACCAGTCTTTTAATGAGTACAGGAAAAGGTTC
ATGCTGAAGCCTTACGAGAGCTTTGAAGAACTGACGGGCGAAAAGGAAATGTCCGCGGAACTGG
AAGCGTTGTACGGAGATATTGATGCGGTAGAGCTCTACCCCGCGCTTCTGGTCGAAAAGCCCCGG
CCAGATGCCATTTTCGGGGAAACCATGGTTGAAGTGGGCGCCCCATTCAGTTTGAAAGGTCTGAT
GGGTAATGTAATTTGCAGTCCGGCGTACTGGAAGCCTTCCACTTTTGGTGGGGAAGTGGGGTTTCA
AATTATCAATACGGCCTCAATTCAGTCTCTGATTTGTAACAATGTTAAGGGATGTCCCTTTACATCT
TTTAGTGTACCGGACCCCGAGCTTATTAAGACCGTGACCATAAATGCTTCAAGCTCTAGAAGTGGT
CTTGATGATATCAACCCCACAGTTTTGCTTAAGGAAAGGAGCACGGAGCTC*GGAAGCGGAGCTAC*
*TAACTTCAGCCTGCTGAAGCAGGCTGGAGACGTCGAGGAGAACCCTGGACCT*AGCATGAACAACTC
AAAACAGTTGGTCTCCCCAGCAGCGGCCCTTTTGTCCAACACAACGTGTCAGACTGAGAATAGACTC
AGTGTATTTTTTAGCGTGATTTTTATGACCGTCGGTATCCTGTCTAACTCTCTTGCCATAGCAATATTG
ATGAAAGCCTATCAGCGATTCCGGCAAAAGTCTAAGGCGTCATTTTTGTTGTTGGCAAGCGGGCTTG
TCATCACGGACTTTTTCGGGCACCTCATTAACGGAGCCATAGCCGTGTTCGTTTATGCTTCAGACAAA
GAGTGGATACGATTCGATCAGAGCAATGTGCTTTGCAGTATCTTTGGCATATGTATGGTGTTTAGTGG
ATTGTGTCCACTCTTGCTTGGGAGCGTGATGGCTATTGAAAGATGCATCGGGGTGACTAAACCTATC
TTTCACAGTACCAAAATTACATCTAAGCACGTCAAGATGATGTTGTCCGGGGTGTGTCTTTTTGCTGT
CTTTATTGCGTTGTTGCCAATACTGGGCCACAGGGACTACAAAATTCAGGCCTCACGCACTTG

FIG. 23E

GTGCTTCTATAACACTGAGGATATTAAAGACTGGGAGGATAGGTTTTATCTTCTTCTTTTCTCATTCCT
CGGTCTGCTCGCACTGGGGGTATCCCTTTTGTGTAACGCTATCACAGGTATCACCTTGTTGCGCGTT
AAATTTAAGAGCCAACAGCATCGCCAGGGGAGGTCACATCACCTCGAAATGGTAATACAGTTGCTCG
CGATCATGTGTGTTAGTTGTATCTGCTGGTCACCCTTCTTGGGATATAGAATAATTCTGAATGGAAAA
GAAAAGTACAAAGTCTATGAAGAACAGAGCGATTTTCTGCATCGATTGCAATGGCCCACTTTGGAATA
AAAAACAAACAAA*CTGAGATGCAGGTACATCCCACTGATGAGTCCCAAATAGGACGAAAGGGAGAG*
*GTGAAGAATACGACCACCTAGGCTCGAAAGAGCCTAAAACATACCTTCTGGGATTCCACTGCTAT*
*CCAC*AAAAAGAAAAATAAAAAGCGGCCGCTGCAGGAGTCGGTCGACTAGAGCTCGCTGATCAGCCT
CGACTGTGCCTTCTAGTTGCCAGCCATCTGTTGTTTGCCCCTCCCCCGTGCCTTCCTTGACCCTGGA
AGGTGCCACTCCCACTGTCCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGGGAAGACAATAGCAGG
CATGCTGGGGAGAGATCTAGGAACCCCTAGTGATGGAGTTGGCCACTCCCTCTCTGCGCGCTCGCT
CGCTCACTGAGGCCGCCCGGGCAAAGCCCGGGCGTCGGGCGACCTTTGGTCGCCCGGCCTCAGT
GAGCGAGCGAGCGCGCAGAGAGGGAGTGGCCAACC

ADDITIONAL RIBOSWITCH SEQUENCES TO TC40 AND TC45

L2bulge9 (Theophylline OFF switch) (SEQ ID NO:64)

CTCGAGGCGATCGCAAACAAACAAAGCTGTCACCGGATGTGCTTTCCGGTCTGATGAGTCCGTTGTC
CAATACCAGCATCGTCTTGATGCCCTTGGCAGTGGATGGGGACGGAGGACGAAACAGCAAAAAGAA
AAATAAAAATTTTTTTTTTAATTAATCTTGGGCCC

Theo6HDV (Theophylline OFF switch) (SEQ ID NO:65)

ATGGCCGGCATGGTCCCAGCCTCCTCGCTGGCGCCGGCTGGGCAACCACATACCAGCCGAAAGGC
CCTTGGCAGGTGGGCGAATGGGACGCACAAATCTCTCTAGCTTCCCAGAGAGAAGCGAGAGAAAAG
TGGCTCTC

GuaM8HDV (Guanine OFF switch) (SEQ ID NO:66)

ATGGCCGGCATGGTCCCAGCCTCCTCGCTGGCGCCGGCTGGGCAATGCTATAATCGCGTGGATATG
GCACGCAAGTTTCTACCGGGCACCGTAAATGTCCGACTAGTAGCGAATGGGACGCACAAATCTCTCT
AG

K19 (Tetracycline ON switch) ((SEQ ID NO:67)

CAAACAAACAAAGGCGCGTCCTGGATTCGTGGTAAAACATACCAGATTTCGATCTGGAGAGGTGAAG
AATACGACCACCTGTAGTATCCAGCTGATGAGTCCCAAATAGGACGAAACGCGCTAAACAAACAAAC

SEQUENCE LISTING

```
Sequence total quantity: 80
SEQ ID NO: 1            moltype = DNA  length = 215
FEATURE                 Location/Qualifiers
misc_feature            1..215
                        note = synthetic
source                  1..215
                        mol_type = other DNA
                        organism = synthetic construct
SEQUENCE: 1
cgtatcagca ggtcccataa gctttcgaca attaacgagt gtgtactcgt tctatcatct  60
cacagttaaa gtcgggagaa taggagccgc acgggtcctg ataccagcgt gagcggagag  120
aatcttcttt ctgtctatta gtgaagccac agatgtaata gacagaaaga agattctctc  180
cgcctacgcc cttggcagca ccgtacggtt cgatc                             215

SEQ ID NO: 2            moltype = DNA  length = 121
FEATURE                 Location/Qualifiers
misc_feature            1..121
                        note = synthetic
source                  1..121
```

```
                        mol_type = other DNA
                        organism = synthetic construct
SEQUENCE: 2
ctagcgagag aatcttcttt ctgtctataa aagagagaat cttctttctg tctataaaag  60
agagaatctt ctttctgtct ataaaagaga gaatcttctt tctgtctatg tcgaccctgc  120
a                                                                  121

SEQ ID NO: 3            moltype = DNA  length = 286
FEATURE                 Location/Qualifiers
misc_feature            1..286
                        note = synthetic
source                  1..286
                        mol_type = other DNA
                        organism = synthetic construct
SEQUENCE: 3
ggttggccac tccctctctg cgcgctcgct cgctcactga ggccgggcga ccaaaggtcg  60
cccgacgccc gggctttgcc cgggcggcct cagtgagcga gcgagcgcgc agagagggag  120
tggccaactc catcactagg ggtaccccta gtgatggagt tggccactcc ctctctgcgc  180
gctcgctcgc tcactgaggc cgcccgggca aagcccgggc gtcgggcgac ctttggtcgc  240
ccggcctcag tgagcgagcg agcgcgcaga gagggagtgg ccaacc                 286

SEQ ID NO: 4            moltype = DNA  length = 236
FEATURE                 Location/Qualifiers
misc_feature            1..236
                        note = synthetic
source                  1..236
                        mol_type = other DNA
                        organism = synthetic construct
SEQUENCE: 4
tcgactagag ctcgctgatc agcctcgact gtgccttcta gttgccagcc atctgttgtt  60
tgcccctccc ccgtgccttc cttgaccctg gaaggtgcca ctcccactgt cctttcctaa  120
taaaatgagg aaattgcatc gcattgtctg agtaggtgtc attctattct ggggggtggg  180
gtggggcagg acagcaaggg ggaggattgg gaagacaata gcaggcatgc tgggga      236

SEQ ID NO: 5            moltype = DNA  length = 202
FEATURE                 Location/Qualifiers
misc_feature            1..202
                        note = synthetic
source                  1..202
                        mol_type = other DNA
                        organism = synthetic construct
SEQUENCE: 5
ggtgagcggg cgggacggcc cttctcctcc gggctgtaat tagcgcttgg tttaatgacg  60
gcttgtttct tttctgtggc tgcgtgaaag ccttgagggg ctccgggagc tagagcctct  120
gctaaccatg ttcatgcctt cttctttttc ctacagctcc tgggcaacgt gctggttatt  180
gtgctgtctc atcattttgg ca                                           202

SEQ ID NO: 6            moltype = DNA  length = 255
FEATURE                 Location/Qualifiers
misc_feature            1..255
                        note = synthetic
source                  1..255
                        mol_type = other DNA
                        organism = synthetic construct
SEQUENCE: 6
catggtcgag gtgagcccca cgttctgctt cactctcccc atctcccccc cctccccacc  60
cccaattttg tatttattta tttttaatt atttgtgca gcgatggggg cgggggggggg  120
ggggggcgc gcgccaggcg gggcggggcg gggcgagggg cggggcgggg cgaggcggag  180
aggtgcggcg gcagccaatc agagcggcgc gctccgaaag tttcctttta tggcgaggcg  240
gcggcggcgg cggcc                                                   255

SEQ ID NO: 7            moltype = DNA  length = 255
FEATURE                 Location/Qualifiers
misc_feature            1..255
                        note = synthetic
source                  1..255
                        mol_type = other DNA
                        organism = synthetic construct
SEQUENCE: 7
aattcggtac ccctagttat taatagtaat caattacggg gtcattagtt catagcccat  60
atatggagtt ccgcgttaca taacttacgg taaatggccc gcctggctga ccgcccaacg  120
acccccgccc attgacgtca ataatgacgt atgttcccat agtaacgcca atagggactt  180
tccattgacg tcaatgggtg gactatttac ggtaaactgc ccacttggca gtacatcaag  240
tgtatcatat gccaa                                                   255

SEQ ID NO: 8            moltype = DNA  length = 1374
FEATURE                 Location/Qualifiers
misc_feature            1..1374
                        note = synthetic
```

```
source                  1..1374
                        mol_type = other DNA
                        organism = synthetic construct
SEQUENCE: 8
atggtatcat attgggacac aggagtcctc ctgtgcgccc ttttgagctg tcttttgctg  60
acgggttctt cttcaggttc tgataccggg agaccattcg ttgaaatgta tagtgagata  120
cccgaaatta tacatatgac tgaagggcgc gagctcgtca taccctgtcg ggtaacaagt  180
ccaaacataa cagtgaccct gaagaagttc cctttggata ctctcattcc cgacgggaag  240
cgaataattt gggactcaag gaagggattt atcatatcta atgcaacata taaggaaata  300
gggctcctca catgcgaagc cacagtcaac gggcacctct acaaaactaa ttacctgacc  360
catcgacaga caaataccat cattgatgtg gttctgagtc catctcatgg aatagagttg  420
agtgtagggg agaagcttgt tctcaattgc acagctagaa ccgagttgaa cgtgggtatc  480
gattttaact gggaataccc atctagtaag caccaacaca aaaaacttgt caatcgagat  540
ttgaaaactc aatctggtag cgagatgaaa aagttcctgt caactcttac aatcgatggc  600
gtgacccgga gtgatcaagg attgtatacc tgcgccgcca gctctggcct gatgactaaa  660
aagaacagca cctttgtacg agtgcatgaa aaggataaga ctcatacatg ccctccttgt  720
cccgctccag agctgctggg aggtcccagt gttttcctct tcccaccaaa gcccaaagat  780
actctgatga ttagccggac ccctgaggtg acttgcgtcg tggtggatgt ttcacatgaa  840
gatccagaag tgaagttcaa ttggtacgtt gatggtgtgg aggtacacaa tgccaagact  900
aaacctcggg aggaacagta taacagcact tacagagttg tcagcgtact cacagtgctt  960
catcaggact ggttgaatgg taaggagtat aagtgcaaag tgagtaataa ggctctgcca  1020
gcacccatag agaagacaat ctcaaaggcc aaaggccagc cccgagaacc acaagtatac  1080
acactgccac ctagtagaga cgagttgaca aaaaatcagg tcagcctcac ctgtctcgtg  1140
aaaggcttct accctagcga cattgccgta gaatgggaaa gcaacgggca accagaaaac  1200
aattataaga caacacctcc cgttctcgat agtgacggaa gtttcttcct gtatagcaaa  1260
cttaccgtgg ataaatcaag atggcagcaa ggtaatgtgt ttagctgttc agtaatgcac  1320
gaagctctgc ataaccacta cacccaaaaa tctttgtctc tgtctccagg gtga        1374

SEQ ID NO: 9            moltype = DNA  length = 3325
FEATURE                 Location/Qualifiers
misc_feature            1..3325
                        note = synthetic
source                  1..3325
                        mol_type = other DNA
                        organism = synthetic construct
SEQUENCE: 9
ggttggccac tccctctctg cgcgctcgct cgctcactga ggccgggcga ccaaaggtcg  60
cccgacgccc gggctttgcc cgggcggcct cagtgagcga gcgagcgcgc agagagggag  120
tggccaactc catcactagg ggttcctaga tctgaattcg gtacccctag ttattaatag  180
taatcaatta cggggtcatt agttcatagc ccatatatgg agttccgcgt tacataactt  240
acggtaaatg gcccgcctgg ctgaccgccc aacgaccccc gcccattgac gtcaataatg  300
acgtatgttc ccatagtaac gccaataggg actttccatt gacgtcaatg ggtggactat  360
ttacggtaaa ctgcccactt ggcagtacat caagtgtatc atatgccaag tacgccccct  420
attgacgtca atgacggtaa atggcccgcc tggcattatg cccagtacat gaccttatgg  480
gactttccta cttggcagta catctacgta ttagtcatcg ctattaccat ggtcgaggtg  540
agccccacgt tctgcttcac tctccccatc tcccccccct ccccaccccc aattttgtat  600
ttatttattt tttaattatt ttgtgcagcg atgggggcgg gggggggggg ggggcgcgcg  660
ccaggcgggg cggggcgggg cgaggggcgg ggcggggcga ggcggagagg tgcggcggca  720
gccaatcaga gcggcgcgct ccgaaagttt ccttttatgg cgaggcggcg gcggcggcgg  780
ccctataaaa agcgaagcgc gcggcgggcg ggagtcgctg cgacgctgcc ttcgccccgt  840
gccccgctcc gccgccgcct cgcgccgccc gccccggctc tgactgaccg cgttactccc  900
acaggtgagc gggcgggacg gcccttctcc tccgggctgt aattagcgct tggtttaatg  960
acggcttgtt tctttctgt ggctgcgtga aagccttgag gggctccggg agctagagcc  1020
tctgctaacc atgttcatgc cttcttcttt ttcctacagc tcctgggcaa cgtgctggtt  1080
attgtgctgt ctcatcattt tggcaaagaa ttcctcgaag atctaggcaa cgcgtattgg  1140
gatctcgagg cggccgcgcc gccaccctag cgagagaatc ttctttctgt ctataaaaga  1200
gagaatcttc tttctgtcta taaaagagag aatcttcttt ctgtctataa aagagagaat  1260
cttctttctg tctatgtcga ccctgcaatg gtatcatatt gggacacagg agtcctcctg  1320
tgcgcccttt tgagctgtct tttgctgacg ggttcttctt caggttctga taccgggaga  1380
ccattcgttg aaatgtatag tgagataccc gaaattatac atatgactga agggcgcgag  1440
ctcgtcatac cctgtcgggt aacaagtcca aacataacag tgaccctgaa gaagttccct  1500
ttggatactc tcattcccga cgggaagcga ataatttggg actcaaggaa gggatttatc  1560
atatctaatg caacatataa ggaaataggg ctcctcacat gcgaagccac agtcaacggg  1620
cacctctaca aaactaatta cctgacccat cgacagacaa ataccatcat tgatgtggtt  1680
ctgagtccat ctcatggaat agagttgagt gtaggggaga agcttgttct caattgcaca  1740
gctagaaccg agttgaacgt gggtatcgat tttaactggg aatacccatc tagtaagcac  1800
caacacaaaa aacttgtcaa tcgagatttg aaaactcaat ctggtagcga gatgaaaaag  1860
ttcctgtcaa ctcttacaat cgatggcgtg acccggagtg atcaaggatt gtatacctgc  1920
gccgccagct ctggcctgat gactaaaaag aacagcacct ttgtacgagt gcatgaaaag  1980
gataagactc atacatgccc tccttgtccc gctccagagc tgctgggagg tcccagtgtt  2040
ttcctcttcc caccaaagcc caaagatact ctgatgatta gccggacccc tgaggtgact  2100
tgcgtcgtgg tggatgtttc acatgaagat ccagaagtga agttcaattg gtacgttgat  2160
ggtgtggagg tacacaatgc caagactaaa cctcgggagg aacagtataa cagcacttac  2220
agagttgtca gcgtactcac agtgcttcat caggactggt tgaatggtaa ggagtataag  2280
tgcaaagtga gtaataaggc tctgccagca cccatagaga agacaatctc aaaggccaaa  2340
ggccagcccc gagaaccaca agtatacaca ctgccaccta gtagagacga gttgacaaaa  2400
aatcaggtca gcctcacctg tctcgtgaaa ggcttctacc ctagcgacat tgccgtagaa  2460
tgggaaagca acgggcaacc agaaaacaat tataagacaa cacctcccgt tctcgatagt  2520
gacggaagtt tcttcctgta tagcaaactt accgtggata aatcaagatg gcagcaaggt  2580
```

-continued

```
aatgtgttta gctgttcagt aatgcacgaa gctctgcata accactacac ccaaaaatct  2640
ttgtctctgt ctccagggtg agcgtatcag caggtcccat aagctttcga caattaacga  2700
gtgtgtactc gttctatcat ctcacagtta aagtcgggag aataggagcc gcacgggtcc  2760
tgataccagc gtgagcggag agaatcttct ttctgtctat tagtgaagcc acagatgtaa  2820
tagacagaaa gaagattctc tccgcctacg cccttggcag caccgtacgg ttcgatcagc  2880
ttattggtac atgataagtc tcaggcatcg tacgatgtcg acctgcagga gtcggtcgac  2940
tagagctcgc tgatcagcct cgactgtgcc ttctagttgc cagccatctg ttgtttgccc  3000
ctcccccgtg ccttccttga ccctggaagg tgccactccc actgtccttt cctaataaaa  3060
tgaggaaatt gcatcgcatt gtctgagtag gtgtcattct attctggggg gtggggtggg  3120
gcaggacagc aagggggagg attgggaaga caatagcagg catgctgggg agagatctag  3180
gaacccctag tgatggagtt ggccactccc tctctgcgcg ctcgctcgct cactgaggcc  3240
gcccgggcaa agcccgggcg tcgggcgacc tttggtcgcc cggcctcagt gagcgagcga  3300
gcgcgcagag agggagtggc caacc                                          3325

SEQ ID NO: 10          moltype = DNA  length = 27
FEATURE                Location/Qualifiers
misc_feature           1..27
                       note = synthetic
source                 1..27
                       mol_type = other DNA
                       organism = synthetic construct
SEQUENCE: 10
gagagaatct tctttctgtc tataaaa                                        27

SEQ ID NO: 11          moltype = DNA  length = 168
FEATURE                Location/Qualifiers
misc_feature           1..168
                       note = synthetic
source                 1..168
                       mol_type = other DNA
                       organism = synthetic construct
SEQUENCE: 11
ctcgaggcga tcgcaaacaa acaaagctgt caccggatgt gctttccggt ctgatgagtc  60
cgttgtccaa taccagcatc gtcttgatgc ccttggcagt ggatggggac ggaggacgaa  120
acagcaaaaa gaaaaataaa aatttttttt ttaattaatc ttgggccc                 168

SEQ ID NO: 12          moltype = DNA  length = 175
FEATURE                Location/Qualifiers
misc_feature           1..175
                       note = synthetic
source                 1..175
                       mol_type = other DNA
                       organism = synthetic construct
SEQUENCE: 12
ctcgaggcga tcgcaaacaa acaaagctgt caccggatgt gctttccggt ctgatgagtc  60
cgttgtccaa aacataccag atttcgatct ggagaggtga agaattcgac cacctggacg  120
aggacggagg acgaaacagc aaaaagaaaa ataaaaatta attaatcttg ggccc         175

SEQ ID NO: 13          moltype = DNA  length = 139
FEATURE                Location/Qualifiers
misc_feature           1..139
                       note = synthetic
source                 1..139
                       mol_type = other DNA
                       organism = synthetic construct
SEQUENCE: 13
atggccggca tggtcccagc ctcctcgctg gcgccggctg ggcaaccaca taccagccga  60
aaggcccttg gcaggtgggc gaatgggacg cacaaatctc tctagcttcc cagagagaag  120
cgagagaaaa gtggctctc                                                 139

SEQ ID NO: 14          moltype = DNA  length = 135
FEATURE                Location/Qualifiers
misc_feature           1..135
                       note = synthetic
source                 1..135
                       mol_type = other DNA
                       organism = synthetic construct
SEQUENCE: 14
atggccggca tggtcccagc ctcctcgctg gcgccggctg ggcaatgcta taatcgcgtg  60
gatatggcac gcaagtttct accgggcacc gtaaatgtcc gactagtagc gaatgggacg  120
cacaaatctc tctag                                                     135

SEQ ID NO: 15          moltype = DNA  length = 134
FEATURE                Location/Qualifiers
misc_feature           1..134
                       note = synthetic
source                 1..134
                       mol_type = other DNA
                       organism = synthetic construct
```

-continued

SEQUENCE: 15
caaacaaaca aaggcgcgtc ctggattcgt ggtaaaacat accagatttc gatctggaga 60
ggtgaagaat acgaccacct gtagtatcca gctgatgagt cccaaatagg acgaaacgcg 120
ctaaacaaac aaac 134

SEQ ID NO: 16 moltype = DNA length = 123
FEATURE Location/Qualifiers
misc_feature 1..123
note = synthetic
source 1..123
mol_type = other DNA
organism = synthetic construct
SEQUENCE: 16
ctgaggtgca ggtacatcca gctgacgagt cccaaatagg acgaaaggga gaggtgaaga 60
atacgaccac ctaggctcga aagagcctaa aacatacctt tcctggattc cactgctatc 120
cac 123

SEQ ID NO: 17 moltype = DNA length = 286
FEATURE Location/Qualifiers
misc_feature 1..286
note = synthetic
source 1..286
mol_type = other DNA
organism = synthetic construct
SEQUENCE: 17
ctagcacggg tccctaaaac ataccgtgag cgcgaaagcg cccccatttt gagttagtga 60
agccacagat gtaactcaaa atgggggcgc tttcccgcct acggagaggt gaagaatacg 120
accacctaga agcttattgg tacatgataa caccccaaaa tcgaagcact tcaaaaacac 180
cccaaaatcg aagcacttca aaaacacccc aaaatcgaag cacttcaaaa acaccccaaa 240
atcgaagcac ttcagtctca ggcatcgtac gatgtcgacc tgcagg 286

SEQ ID NO: 18 moltype = DNA length = 1376
FEATURE Location/Qualifiers
misc_feature 1..1376
note = synthetic
source 1..1376
mol_type = other DNA
organism = synthetic construct
SEQUENCE: 18
aatgtccatg ttgttctaca ctctgatcac agcttttctg atcggcatac aggcggaacc 60
acactcagtc tgataccggg agaccattcg ttgaaatgta tagtgagata cccgaaatta 120
tacatatgac tgaagggcgc gagctcgtca taccctgtcg ggtaacaagt ccaaacataa 180
cagtgaccct gaagaagttc cctttggata ctctcattcc cgacgggaag cgaataattt 240
gggactcaag gaagggattt atcatatcta atgcaacata taaggaaata gggctcctca 300
catgcgaagc cacagtcaac gggcacctct acaaaactaa ttacctgacc catcgacaga 360
caaataccat cattgatgtg gttctgagtc catctcatgg aatagagttg agtgtagggg 420
agaagcttgt tctcaattgc acagctagaa ccgagttgaa cgtgggtatc gattttaact 480
gggaataccc atctagtaag caccaacaca aaaaacttgt caatcgagat ttgaaaactc 540
aatctggtag cgagatgaaa aagttcctgt caactcttac aatcgatggc gtgacccgga 600
gtgatcaagg attgtatacc tgcgccgcca gctctggcct gatgactaaa aagaacagca 660
cctttgtacg agtgcatgaa aaggataaga ctcatacatg ccctccttgt cccgctccag 720
agctgctggg aggtcccagt gttttcctct tcccaccaaa gcccaaagat actctgatga 780
ttagccggac ccctgaggtg acttgcgtcg tggtggatgt ttcacatgaa gatccagaag 840
tgaagttcaa ttggtacgtt gatggtgtgg aggtacacaa tgccaagact aaacctcggg 900
aggaacagta taacagcact tacagagttg tcagcgtact cacagtgctt catcaggact 960
ggttgaatgg taaggagtat aagtgcaaag tgagtaataa ggctctgcca gcacccatag 1020
agaagacaat ctcaaaggcc aaaggccagc cccgagaacc acaagtatac acactgccac 1080
ctagtagaga cgagttgaca aaaaatcagg tcagcctcac ctgtctcgtg aaaggcttct 1140
accctagcga cattgccgta gaatgggaaa gcaacgggca accagaaaac aattataaga 1200
caacacctcc cgttctcgat agtgacggaa gtttcttcct gtatagcaaa cttaccgtgg 1260
ataaatcaag atggcagcaa ggtaatgtgt ttagctgttc agtaatgcac gaagctctgc 1320
ataaccacta cacccaaaaa tctttgtctc tgtctccagg gtgaaaacaa acaaaa 1376

SEQ ID NO: 19 moltype = DNA length = 2960
FEATURE Location/Qualifiers
misc_feature 1..2960
note = synthetic
source 1..2960
mol_type = other DNA
organism = synthetic construct
SEQUENCE: 19
ggttggccac tccctctctg cgcgctcgct cgctcactga ggccgggcga ccaaaggtcg 60
cccgacgccc gggctttgcc cgggcggcct cagtgagcga gcgagcgcgc agagagggag 120
tggccaactc catcactagg ggttcctaga tctgaattcg gtacccctag ttattaatag 180
taatcaatta cggggtcatt agttcatagc ccatatatgg agttccgcgt tacataactt 240
acggtaaatg gcccgcctgg ctgaccgccc aacgaccccc gcccattgac gtcaataatg 300
acgtatgttc ccatagtaac gccaataggg actttccatt gacgtcaatg ggtggactat 360
ttacggtaaa ctgcccactt ggcagtacat caagtgtatc atatgccaag tacgccccct 420
attgacgtca atgacggtaa atggcccgcc tggcattatg cccagtacat gaccttatgg 480

```
gactttccta cttggcagta catctacgta ttagtcatcg ctattaccat ggtcgaggtg  540
agccccacgt tctgcttcac tctccccatc tccccccccct ccccaccccc aattttgtat  600
ttatttattt tttaattatt ttgtgcagcg atgggggcgg gggggggggg ggggcgcgcg  660
ccaggcgggg cggggcgggg cgaggggcgg ggcggggcga ggcggagagg tgcggcggca  720
gccaatcaga gcggcgcgct ccgaaagttt ccttttatgg cgaggcggcg gcggcggcgg  780
ccctataaaa agcgaagcgc gcggcgggcg ggagtcgctg cgacgctgcc ttcgccccgt  840
gccccgctcc gccgccgcct cgcgccgccc gccccggctc tgactgaccg cgttactccc  900
acaggtgagc gggcgggacg gcccttctcc tccgggctgt aattagcgct tggtttaatg  960
acggcttgtt tcttttctgt ggctgcgtga aagccttgag gggctccggg agctagagcc  1020
tctgctaacc atgttcatgc cttcttcttt ttcctacagc tcctgggcaa cgtgctggtt  1080
attgtgctgt ctcatcattt tggcaaagaa ttcctcgaag atctaggcaa cgcgtctcga  1140
ggcggccgcc gccaccaatg gtatcatatt gggacacagg agtcctcctg tgcgcccttt  1200
tgagctgtct tttgctgacg ggttcttctt caggttctga taccgggaga ccattcgttg  1260
aaatgtatag tgagataccc gaaattatac atatgactga agggcgcgag ctcgtcatac  1320
cctgtcgggt aacaagtcca aacataacag tgaccctgaa gaagttccct ttggatactc  1380
tcattcccga cgggaagcga ataatttggg actcaaggaa gggatttatc atatctaatg  1440
caacatataa ggaaataggg ctcctcacat gcgaagccac agtcaacggg cacctctaca  1500
aaactaatta cctgacccat cgacagacaa ataccatcat tgatgtggtt ctgagtccat  1560
ctcatggaat agagttgagt gtaggggaga agcttgttct caattgcaca gctagaaccg  1620
agttgaacgt gggtatcgat tttaactggg aatacccatc tagtaagcac caacacaaaa  1680
aacttgtcaa tcgagatttg aaaactcaat ctggtagcga gatgaaaaag ttcctgtcaa  1740
ctcttacaat cgatggcgtg acccggagtg atcaaggatt gtatacctgc gccgccagct  1800
ctggcctgat gactaaaaag aacagcacct ttgtacgagt gcatgaaaag gataagactc  1860
atacatgccc tccttgtccc gctccagagc tgctgggagg tcccagtgtt ttcctcttcc  1920
caccaaagcc caaagatact ctgatgatta gccggacccc tgaggtgact tgcgtcgtgg  1980
tggatgtttc acatgaagat ccagaagtga agttcaattg gtacgttgat ggtgtggagg  2040
tacacaatgc caagactaaa cctcgggagg aacagtataa cagcacttac agagttgtca  2100
gcgtactcac agtgcttcat caggactggt tgaatggtaa ggagtataag tgcaaagtga  2160
gtaataaggc tctgccagca cccatagaga agacaatctc aaaggccaaa ggccagcccc  2220
gagaaccaca agtatacaca ctgccaccta gtagagacga gttgacaaaa aatcaggtca  2280
gcctcacctg tctcgtgaaa ggcttctacc ctagcgacat tgccgtagaa tgggaaagca  2340
acgggcaacc agaaaacaat tataagacaa cacctcccgt tctcgatagt gacggaagtt  2400
tcttcctgta tagcaaactt accgtggata aatcaagatg gcagcaaggt aatgtgttta  2460
gctgttcagt aatgcacgaa gctctgcata accactacac ccaaaaatct ttgtctctgt  2520
ctccagggtg agcggccgca tcggctagca aagcttcctg caggagtcgg tcgactagag  2580
ctcgctgatc agcctcgact gtgccttcta gttgccagcc atctgttgtt tgcccctccc  2640
ccgtgccttc cttgaccctg gaaggtgcca ctcccactgt cctttcctaa taaaatgagg  2700
aaattgcatc gcattgtctg agtaggtgtc attctattct ggggggtggg gtggggcagg  2760
acagcaaggg ggaggattgg gaagacaata gcaggcatgc tggggagaga tctaggaacc  2820
cctagtgatg gagttggcca ctccctctct gcgcgctcgc tcgctcactg aggccgcccg  2880
ggcaaagccc gggcgtcggg cgacctttgg tcgcccggcc tcagtgagcg agcgagcgcg  2940
cagagaggga gtggccaacc                                            2960

SEQ ID NO: 20          moltype = DNA  length = 1374
FEATURE                Location/Qualifiers
misc_feature           1..1374
                       note = synthetic
source                 1..1374
                       mol_type = other DNA
                       organism = synthetic construct
SEQUENCE: 20
atggtatcat attgggacac aggagtcctc ctgtgcgccc ttttgagctg tcttttgctg  60
acgggttctt cttcaggttc tgataccggg agaccattcg ttgaaatgta tagtgagata  120
cccgaaatta tacatatgac tgaagggcgc gagctcgtca taccctgtcg ggtaacaagt  180
ccaaacataa cagtgaccct gaagaagttc cctttggata ctctcattcc cgacgggaag  240
cgaataattt gggactcaag gaagggattt atcatatcta atgcaacata taaggaaata  300
gggctcctca catgcgaagc cacagtcaac gggcacctct acaaaactaa ttacctgacc  360
catcgacaga caaataccat cattgatgtg gttctgagtc catctcatgg aatagagttg  420
agtgtagggg agaagcttgt tctcaattgc acagctagaa ccgagttgaa cgtgggtatc  480
gattttaact gggaataccc atctagtaag caccaacaca aaaaacttgt caatcgagat  540
ttgaaaactc aatctggtag cgagatgaaa aagttcctgt caactcttac aatcgatggc  600
gtgacccgga gtgatcaagg attgtatacc tgcgccgcca gctctggcct gatgactaaa  660
aagaacagca cctttgtacg agtgcatgaa aaggataaga ctcatacatg ccctccttgt  720
cccgctccag agctgctggg aggtcccagt gttttcctct tcccaccaaa gcccaaagat  780
actctgatga ttagccggac ccctgaggtg acttgcgtcg tggtggatgt ttcacatgaa  840
gatccagaag tgaagttcaa ttggtacgtt gatggtgtgg aggtacacaa tgccaagact  900
aaacctcggg aggaacagta taacagcact tacagagttg tcagcgtact cacagtgctt  960
catcaggact ggttgaatgg taaggagtat aagtgcaaag tgagtaataa ggctctgcca  1020
gcacccatag agaagacaat ctcaaaggcc aaaggccagc cccgagaacc acaagtatac  1080
acactgccac ctagtagaga cgagttgaca aaaaatcagg tcagcctcac ctgtctcgtg  1140
aaaggcttct accctagcga cattgccgta gaatgggaaa gcaacgggca accagaaaac  1200
aattataaga caacacctcc cgttctcgat agtgacggaa gtttcttcct gtatagcaaa  1260
cttaccgtgg ataaatcaag atggcagcaa ggtaatgtgt ttagctgttc agtaatgcac  1320
gaagctctgc ataaccacta cacccaaaaa tctttgtctc tgtctccagg gtga       1374

SEQ ID NO: 21          moltype = DNA  length = 153
FEATURE                Location/Qualifiers
misc_feature           1..153
                       note = synthetic
```

```
source                  1..153
                        mol_type = other DNA
                        organism = synthetic construct
SEQUENCE: 21
gaacgcctcc taacgtctgg tcacgaccct gcgtgagcga ccccattgtt caggtttgta  60
ttcttttggc cactgactga gaatacaaat gaacaatggg ggcgcctacg cagcccctcg  120
aaatcacgag ggagacgaga taagggggcg ttt                               153

SEQ ID NO: 22           moltype = DNA  length = 155
FEATURE                 Location/Qualifiers
misc_feature            1..155
                        note = synthetic
source                  1..155
                        mol_type = other DNA
                        organism = synthetic construct
SEQUENCE: 22
gaacgcctcc taacgtctgg tcacgaccct gcgtgagcga ccctgagttc cttccctaaa  60
tacttttggc cactgactga gtatttagga ggaactcagg ggggcgccta cgcagcccct  120
cgaaatcacg agggagacga gataaggggg cgttt                             155

SEQ ID NO: 23           moltype = DNA  length = 155
FEATURE                 Location/Qualifiers
misc_feature            1..155
                        note = synthetic
source                  1..155
                        mol_type = other DNA
                        organism = synthetic construct
SEQUENCE: 23
gaacgcctcc taacgtctgg tcacgaccct gcgtgagcga ccaagagtta acgtgtcgat  60
ctcttttggc cactgactga gagatcgacg ttaactcttg gggcgccta cgcagcccct   120
cgaaatcacg agggagacga gataaggggg cgttt                             155

SEQ ID NO: 24           moltype = DNA  length = 155
FEATURE                 Location/Qualifiers
misc_feature            1..155
                        note = synthetic
source                  1..155
                        mol_type = other DNA
                        organism = synthetic construct
SEQUENCE: 24
gaacgcctcc taacgtctgg tcacgaccct gcgtgagcga cccttcccta aatagtatag  60
atcttttggc cactgactga gatctatact ttagggaagg ggggcgccta cgcagcccct  120
cgaaatcacg agggagacga gataaggggg cgttt                             155

SEQ ID NO: 25           moltype = DNA  length = 155
FEATURE                 Location/Qualifiers
misc_feature            1..155
                        note = synthetic
source                  1..155
                        mol_type = other DNA
                        organism = synthetic construct
SEQUENCE: 25
gaacgcctcc taacgtctgg tcacgaccct gcgtgagcga ccgtgtcgat cttggctcaa  60
ctcttttggc cactgactga gcgtgtcgat tggctcaact ggggcgccta cgcagcccct  120
cgaaatcacg agggagacga gataaggggg cgttt                             155

SEQ ID NO: 26           moltype = DNA  length = 127
FEATURE                 Location/Qualifiers
misc_feature            1..127
                        note = synthetic
source                  1..127
                        mol_type = other DNA
                        organism = synthetic construct
SEQUENCE: 26
gaacgcctcc ttgataccag ctgcgtgagc gaccccattg ttcaggtttg tattcttttg  60
gccactgact gagaatacaa atgaacaatg ggggcgccta cgcgcccttg gcagcaaggg  120
ggcgttt                                                            127

SEQ ID NO: 27           moltype = DNA  length = 129
FEATURE                 Location/Qualifiers
misc_feature            1..129
                        note = synthetic
source                  1..129
                        mol_type = other DNA
                        organism = synthetic construct
SEQUENCE: 27
gaacgcctcc ttgataccag ctgcgtgagc gaccctgagt tccttcccta aatacttttg  60
gccactgact gagtatttag gaggaactca ggggggcgcc tacgcgccct tggcagcaag  120
gggcgttt                                                           129
```

```
SEQ ID NO: 28          moltype = DNA  length = 129
FEATURE                Location/Qualifiers
misc_feature           1..129
                       note = synthetic
source                 1..129
                       mol_type = other DNA
                       organism = synthetic construct
SEQUENCE: 28
gaacgcctcc ttgataccag ctgcgtgagc gaccaagagt taacgtgtcg atctcttttg  60
gccactgact gagagatcga cgttaactct tgggggcgcc tacgcgccct tggcagcaag  120
ggggcgttt                                                          129

SEQ ID NO: 29          moltype = DNA  length = 129
FEATURE                Location/Qualifiers
misc_feature           1..129
                       note = synthetic
source                 1..129
                       mol_type = other DNA
                       organism = synthetic construct
SEQUENCE: 29
gaacgcctcc ttgataccag ctgcgtgagc gacccttccc taaatagtat agatcttttg  60
gccactgact gagatctata ctttagggaa ggggggcgcc tacgcgccct tggcagcaag  120
ggggcgttt                                                          129

SEQ ID NO: 30          moltype = DNA  length = 129
FEATURE                Location/Qualifiers
misc_feature           1..129
                       note = synthetic
source                 1..129
                       mol_type = other DNA
                       organism = synthetic construct
SEQUENCE: 30
gaacgcctcc ttgataccag ctgcgtgagc gaccgtgtcg atcttggctc aactcttttg  60
gccactgact gagcgtgtcg attggctcaa ctggggcgcc tacgcgccct tggcagcaag  120
ggggcgttt                                                          129

SEQ ID NO: 31          moltype = DNA  length = 151
FEATURE                Location/Qualifiers
misc_feature           1..151
                       note = synthetic
source                 1..151
                       mol_type = other DNA
                       organism = synthetic construct
SEQUENCE: 31
gaacgcctcc tagaggtgaa gaatacgacc accttgcgtg agcgacccca ttgttcaggt  60
ttgtattctt ttggccactg actgagaata caaatgaaca atgggggcgc ctacgcaggc  120
tcgaaagagc ctaaaacata agggggcgtt t                                 151

SEQ ID NO: 32          moltype = DNA  length = 153
FEATURE                Location/Qualifiers
misc_feature           1..153
                       note = synthetic
source                 1..153
                       mol_type = other DNA
                       organism = synthetic construct
SEQUENCE: 32
gaacgcctcc tagaggtgaa gaatacgacc accttgcgtg agcgaccctg agttccttcc  60
ctaaatactt ttggccactg actgagtatt taggaggaac tcaggggggc gcctacgcag  120
gctcgaaaga gcctaaaaca taagggggcg ttt                               153

SEQ ID NO: 33          moltype = DNA  length = 153
FEATURE                Location/Qualifiers
misc_feature           1..153
                       note = synthetic
source                 1..153
                       mol_type = other DNA
                       organism = synthetic construct
SEQUENCE: 33
gaacgcctcc tagaggtgaa gaatacgacc accttgcgtg agcgaccaag agttaacgtg  60
tcgatctctt ttggccactg actgagagat cgacgttaac tcttgggggc gcctacgcag  120
gctcgaaaga gcctaaaaca taagggggcg ttt                               153

SEQ ID NO: 34          moltype = DNA  length = 153
FEATURE                Location/Qualifiers
misc_feature           1..153
                       note = synthetic
source                 1..153
                       mol_type = other DNA
```

```
                         organism = synthetic construct
SEQUENCE: 34
gaacgcctcc tagaggtgaa gaatacgacc accttgcgtg agcgaccctt ccctaaatag  60
tatagatctt ttggccactg actgagatct atactttagg gaagggggc gcctacgcag  120
gctcgaaaga gcctaaaaca taagggggcg ttt                              153

SEQ ID NO: 35            moltype = DNA  length = 153
FEATURE                  Location/Qualifiers
misc_feature             1..153
                         note = synthetic
source                   1..153
                         mol_type = other DNA
                         organism = synthetic construct
SEQUENCE: 35
gaacgcctcc tagaggtgaa gaatacgacc accttgcgtg agcgaccgtg tcgatcttgg  60
ctcaactctt ttggccactg actgagcgtg tcgattggct caactggggc gcctacgcag  120
gctcgaaaga gcctaaaaca taagggggcg ttt                              153

SEQ ID NO: 36            moltype = DNA  length = 2077
FEATURE                  Location/Qualifiers
misc_feature             1..2077
                         note = synthetic
source                   1..2077
                         mol_type = other DNA
                         organism = synthetic construct
SEQUENCE: 36
aatggtcagc tactgggaca ccggggtcct gctgtgcgcg ctgctcagct gtctgcttct  60
cacaggatct agttcaggtt caaaattaaa agatcctgaa ctgagtttaa aaggcaccca  120
gcacatcatg caagcaggcc agacactgca tctccaatgc agggggggaag cagcccataa  180
atggtctttg cctgaaatgg tgagtaagga aagcgaaagg ctgagcataa ctaaatctgc  240
ctgtggaaga aatggcaaac aattctgcag tactttaacc ttgaacacag ctcaagcaaa  300
ccacactggc ttctacagct gcaaatatct agctgtacct acttcaaaga agaaggaaac  360
agaatctgca atctatatat ttattagtga tacaggtaga cctttcgtag agatgtacag  420
tgaaatcccc gaaattatac acatgactga aggaagggag ctcgtcattc cctgccgggt  480
tacgtcacct aacatcactg ttactttaaa aaagtttcca cttgacactt tgatccctga  540
tggaaaacgc ataatctggg acagtagaaa gggcttcatc atatcaaatg caacgtacaa  600
agaaataggg cttctgacct gtgaagcaac agtcaatggg catttgtata agacaaacta  660
tctcacacat cgacaaacca atacaatcat agatgtccaa ataagcacac cacgcccagt  720
caaattactt agaggccata ctcttgtcct caattgtact gctaccactc ccttgaacac  780
gagagttcaa atgacctgga gttaccctga tgaaaaaaat aagagagctt ccgtaaggcg  840
acgaattgac caaagcaatt cccatgccaa catattctac agtgttctta ctattgacaa  900
aatgcagaac aaagacaaag gactttatac ttgtcgtgta aggagtggac catcattcaa  960
atctgttaac acctcagtgc atatatatga taaagcattc atcactgtga aacatcgaaa  1020
acagcaggtg cttgaaaccg tagctggcaa gcggtcttac cggctctcta tgaaagtgaa  1080
ggcatttccc tcgccggaag ttgtatggtt aaaagatggg ttacctgcga ctgagaaatc  1140
tgctcgctat ttgactcgtg gctactcgtt aattatcaag gacgtaactg aagaggatgc  1200
agggaattat acaatcttgc tgagcataaa acagtcaaat gtgtttaaaa acctcactgc  1260
cactctaatt gtcaatgtga aaccccagat ttacgaaaag gccgtgtcat cgtttccaga  1320
cccggctctc tacccactgg gcagcagaca aatcctgact tgtaccgcat atggtatccc  1380
tcaacctaca atcaagtggt tctggcaccc ctgtaaccat aatcattccg aagcaaggtg  1440
tgacttttgt tccaataatg aagagtcctt tatcctggat gctgacagca acatgggaaa  1500
cagaattgag agcatcactc agcgcatggc aataatagaa ggaaagaata agatggctag  1560
caccttggtt gtggctgact ctagaatttc tggaatctac atttgcatag cttccaataa  1620
agttgggact gtgggaagaa acataagctt ttatatcaca gatgtgccaa atgggtttca  1680
tgttaacttg gaaaaaatgc cgacggaagg agaggacctg aaactgtctt gcacagttaa  1740
caagttctta tacagagacg ttacttggat tttactgcgg acagttaata acagaacaat  1800
gcactacagt attagcaagc aaaaaatggc catcactaag gagcactcca tcactcttaa  1860
tcttaccatc atgaatgttt ccctgcaaga ttcaggcacc tatgcctgca gagccaggaa  1920
tgtatacaca ggggaagaaa tcctccagaa gaaagaaatt acaatcagag gtgagcactg  1980
caacaaaaag gctgttttct ctcggatctc caaatttaaa agcacaagga atgattgtac  2040
cacacaaagt aatgtaaaac attaaaaaca aacaaaa                           2077

SEQ ID NO: 37            moltype = DNA  length = 155
FEATURE                  Location/Qualifiers
misc_feature             1..155
                         note = synthetic
source                   1..155
                         mol_type = other DNA
                         organism = synthetic construct
SEQUENCE: 37
gaacgcctcc taacgtctgg tcacgaccct gcgtgagcga ccagacgaag agtgtcctag  60
atcttttggc cactgactga gatctaggac tcttcgtctg gggcgcctta cgcagcccct  120
cgaaatcacg agggagacga gataaggggg cgttt                             155

SEQ ID NO: 38            moltype = DNA  length = 155
FEATURE                  Location/Qualifiers
misc_feature             1..155
                         note = synthetic
source                   1..155
```

```
                        mol_type = other DNA
                        organism = synthetic construct
SEQUENCE: 38
gaacgcctcc taacgtctgg tcacgaccct gcgtgagcga ccgctttccg actcgtattg  60
atcttttggc cactgactga gatcaatacg tcggaaagcg ggggcgccta cgcagcccct  120
cgaaatcacg agggagacga gataaggggg cgttt                             155

SEQ ID NO: 39           moltype = DNA  length = 155
FEATURE                 Location/Qualifiers
misc_feature            1..155
                        note = synthetic
source                  1..155
                        mol_type = other DNA
                        organism = synthetic construct
SEQUENCE: 39
gaacgcctcc taacgtctgg tcacgaccct gcgtgagcga ccaccttctt taccgtttgt  60
tacttttggc cactgactga gtaacaaact aaagaaggtg ggggcgccta cgcagcccct  120
cgaaatcacg agggagacga gataaggggg cgttt                             155

SEQ ID NO: 40           moltype = DNA  length = 155
FEATURE                 Location/Qualifiers
misc_feature            1..155
                        note = synthetic
source                  1..155
                        mol_type = other DNA
                        organism = synthetic construct
SEQUENCE: 40
gaacgcctcc taacgtctgg tcacgaccct gcgtgagcga cccgtttgtt aagacgtcat  60
gacttttggc cactgactga gtcatgacgt taacaaacgg ggggcgccta cgcagcccct  120
cgaaatcacg agggagacga gataaggggg cgttt                             155

SEQ ID NO: 41           moltype = DNA  length = 155
FEATURE                 Location/Qualifiers
misc_feature            1..155
                        note = synthetic
source                  1..155
                        mol_type = other DNA
                        organism = synthetic construct
SEQUENCE: 41
gaacgcctcc taacgtctgg tcacgaccct gcgtgagcga cgcaaatatc tagctgtacc  60
tacttttggc cactgactga gtaggtacat agatatttgc ggggcgccta cgcagcccct  120
cgaaatcacg agggagacga gataaggggg cgttt                             155

SEQ ID NO: 42           moltype = DNA  length = 129
FEATURE                 Location/Qualifiers
misc_feature            1..129
                        note = synthetic
source                  1..129
                        mol_type = other DNA
                        organism = synthetic construct
SEQUENCE: 42
gaacgcctcc ttgataccag ctgcgtgagc gaccagacga agagtgtcct agatcttttg  60
gccactgact gagatctagg actcttcgtc tgggggcgcc tacgcgccct tggcagcaag  120
ggggcgttt                                                          129

SEQ ID NO: 43           moltype = DNA  length = 129
FEATURE                 Location/Qualifiers
misc_feature            1..129
                        note = synthetic
source                  1..129
                        mol_type = other DNA
                        organism = synthetic construct
SEQUENCE: 43
gaacgcctcc ttgataccag ctgcgtgagc gaccgctttc cgactcgtat tgatcttttg  60
gccactgact gagatcaata cgtcggaaag cgggggcgcc tacgcgccct tggcagcaag  120
ggggcgttt                                                          129

SEQ ID NO: 44           moltype = DNA  length = 129
FEATURE                 Location/Qualifiers
misc_feature            1..129
                        note = synthetic
source                  1..129
                        mol_type = other DNA
                        organism = synthetic construct
SEQUENCE: 44
gaacgcctcc ttgataccag ctgcgtgagc gaccaccttc tttaccgttt gttacttttg  60
gccactgact gagtaacaaa ctaaagaagg tgggggcgcc tacgcgccct tggcagcaag  120
ggggcgttt                                                          129
```

```
SEQ ID NO: 45          moltype = DNA  length = 129
FEATURE                Location/Qualifiers
misc_feature           1..129
                       note = synthetic
source                 1..129
                       mol_type = other DNA
                       organism = synthetic construct
SEQUENCE: 45
gaacgcctcc ttgataccag ctgcgtgagc gacccgtttg ttaagacgtc atgacttttg  60
gccactgact gagtcatgac gttaacaaac ggggggcgcc tacgcgccct tggcagcaag  120
ggggcgttt                                                          129

SEQ ID NO: 46          moltype = DNA  length = 129
FEATURE                Location/Qualifiers
misc_feature           1..129
                       note = synthetic
source                 1..129
                       mol_type = other DNA
                       organism = synthetic construct
SEQUENCE: 46
gaacgcctcc ttgataccag ctgcgtgagc gacgcaaata tctagctgta cctacttttg  60
gccactgact gagtaggtac atagatattt gcggggcgcc tacgcgccct tggcagcaag  120
ggggcgttt                                                          129

SEQ ID NO: 47          moltype = DNA  length = 153
FEATURE                Location/Qualifiers
misc_feature           1..153
                       note = synthetic
source                 1..153
                       mol_type = other DNA
                       organism = synthetic construct
SEQUENCE: 47
gaacgcctcc tagaggtgaa gaatacgacc accttgcgtg agcgaccaga cgaagagtgt  60
cctagatctt ttggccactg actgagatct aggactcttc gtctgggggc gcctacgcag  120
gctcgaaaga gcctaaaaca taagggggcg ttt                               153

SEQ ID NO: 48          moltype = DNA  length = 153
FEATURE                Location/Qualifiers
misc_feature           1..153
                       note = synthetic
source                 1..153
                       mol_type = other DNA
                       organism = synthetic construct
SEQUENCE: 48
gaacgcctcc tagaggtgaa gaatacgacc accttgcgtg agcgaccgct ttccgactcg  60
tattgatctt ttggccactg actgagatca atacgtcgga aagcgggggc gcctacgcag  120
gctcgaaaga gcctaaaaca taagggggcg ttt                               153

SEQ ID NO: 49          moltype = DNA  length = 153
FEATURE                Location/Qualifiers
misc_feature           1..153
                       note = synthetic
source                 1..153
                       mol_type = other DNA
                       organism = synthetic construct
SEQUENCE: 49
gaacgcctcc tagaggtgaa gaatacgacc accttgcgtg agcgaccacc ttctttaccg  60
tttgttactt ttggccactg actgagtaac aaactaaaga aggtgggggc gcctacgcag  120
gctcgaaaga gcctaaaaca taagggggcg ttt                               153

SEQ ID NO: 50          moltype = DNA  length = 153
FEATURE                Location/Qualifiers
misc_feature           1..153
                       note = synthetic
source                 1..153
                       mol_type = other DNA
                       organism = synthetic construct
SEQUENCE: 50
gaacgcctcc tagaggtgaa gaatacgacc accttgcgtg agcgacccgt ttgttaagac  60
gtcatgactt ttggccactg actgagtcat gacgttaaca aacgggggc gcctacgcag  120
gctcgaaaga gcctaaaaca taagggggcg ttt                               153

SEQ ID NO: 51          moltype = DNA  length = 142
FEATURE                Location/Qualifiers
misc_feature           1..142
                       note = synthetic
source                 1..142
                       mol_type = other DNA
                       organism = synthetic construct
```

```
SEQUENCE: 51
gaacgcctcc tagaggtgaa gaatacgacc accttgcgtg agcgacgcaa atatctagct  60
gtacctactt ttggccactg actgagtagg tacatagata tttgcggggc gcctacgcag  120
gctcgaaaga gcctaaaaca ta                                           142

SEQ ID NO: 52           moltype = DNA  length = 1815
FEATURE                 Location/Qualifiers
misc_feature            1..1815
                        note = synthetic
source                  1..1815
                        mol_type = other DNA
                        organism = synthetic construct
SEQUENCE: 52
atgcttgccc gggccctgct tctgtgtgcg gtattggcac tgagtcacac agccaacccg  60
tgctgctcac acccatgtca gaatcgggga gtttgcatgt cagtagggtt tgaccaatat  120
aagtgcgact gtacccggac aggcttttat ggagaaaatt gttctacacc cgaatttttg  180
acgaggatta agctctttct gaagcctaca ccaaatacag tccattatat cctcacgcac  240
ttcaagggtt tttggaatgt cgtaaacaac attccgtttc tgagaaatgc gataatgtct  300
tacgtcctta catcccggag ccaccttatt gactcacccc caacatacaa cgccgactac  360
ggatacaaaa gttgggaagc tttctccaac ctgtcttact acacgcgagc attgcctcct  420
gtacccgacg attgcccgac gccgttgggg gtgaaaggaa aaaagcagct cccggactca  480
aacgaaatag tagagaaatt gttgcttcgc cgaaaattta taccagaccc gcagggtagc  540
aatatgatgt ttgcgttctt cgctcagcac ttcactcacc aattctttaa gacagaccac  600
aagagaggtc ccgcattcac gaatggcctt ggacacggcg tcgacttgaa ccacatatat  660
ggggagacat tggccagaca aaggaaactt cgattgttta aggatgggaa aatgaaatac  720
caaattattg atggcgagat gtatcctcca acagtgaagg atacgcaagc ggagatgatt  780
tatccaccgc aggtaccaga gcatttgcgg ttcgcggtgg ggcaggaagt atttggactt  840
gttcccggtc tgatgatgta cgccacaata tggctccggg agcataatcg cgtgtgtgac  900
gtacttaagc aagagcaccc ggaatggggc gacgagcaac tttttcaaac gagtcgactg  960
attctcattg ggggaaacgat taaaatagtg atcgaagatt atgtgcaaca tctttctggt  1020
taccacttta agttgaagtt cgatcctgag ctgcttttca ataaacaatt ccagtatcaa  1080
aacagaatcg ccgcggagtt caacacgctg tatcattggc atcccctgtt gcccgatact  1140
tttcaaatcc atgaccagaa atacaattac cagcaattta tatataataa ctctatcctc  1200
ctggagcatg gcattacaca attcgttgaa agtttcacaa ggcagatcgc aggaagagtt  1260
gcgggtggcc ggaatgtgcc gcctgccgtg caaaaggtat cacaggctag catcgaccaa  1320
tcaaggcaaa tgaagtacca gtcttttaat gagtacagga aaaggttcat gctgaagcct  1380
tacgagagct ttgaagaact gacgggcgaa aaggaaatgt ccgcggaact ggaagcgttg  1440
tacggagata ttgatgcggt agagctctac cccgcgcttc tggtcgaaaa gccccggcca  1500
gatgccattt tcggggaaac catggttgaa gtgggcgccc cattcagttt gaaaggtctg  1560
atgggtaatg taatttgcag tccggcgtac tggaagcctt ccacttttgg tggggaagtg  1620
gggtttcaaa ttatcaatac ggcctcaatt cagtctctga tttgtaacaa tgttaaggga  1680
tgtcccttta catcttttag tgtaccggac cccgagctta ttaagaccgt gaccataaat  1740
gcttcaagct ctagaagtgg tcttgatgat atcaacccca cagttttgct taaggaaagg  1800
agcacggagc tctaa                                                   1815

SEQ ID NO: 53           moltype = DNA  length = 894
FEATURE                 Location/Qualifiers
misc_feature            1..894
                        note = synthetic
source                  1..894
                        mol_type = other DNA
                        organism = synthetic construct
SEQUENCE: 53
atgagcatga acaactcaaa acagttggtc tccccagcag cggccctttt gtccaacaca  60
acgtgtcaga ctgagaatag actcagtgta ttttttagcg tgatttttat gaccgtcggt  120
atcctgtcta actctcttgc catagcaata ttgatgaaag cctatcagcg attccggcaa  180
aagtctaagg cgtcattttt gttgttggca agcgggcttg tcatcacgga ctttttcggg  240
cacctcatta acggagccat agccgtgttc gtttatgctt cagacaaaga gtggatacga  300
ttcgatcaga gcaatgtgct ttgcagtatc tttggcatat gtatggtgtt tagtggattg  360
tgtccactct tgcttgggag cgtgatggct attgaaagat gcatcggggt gactaaacct  420
atctttcaca gtaccaaaat tacatctaag cacgtcaaga tgatgttgtc cggggtgtgt  480
ctttttgctg tctttattgc gttgttgcca atactgggcc acagggacta caaaattcag  540
gcctcacgca cttggtgctt ctataacact gaggatatta aagactggga ggataggttt  600
tatcttcttc ttttctcatt cctcggtctg ctcgcactgg gggtatccct tttgtgtaac  660
gctatcacag gtatcacctt gttgcgcgtt aaatttaaga gccaacagca tcgccagggg  720
aggtcacatc acctcgaaat ggtaatacag ttgctcgcga tcatgtgtgt tagttgtatc  780
tgctggtcac ccttcttggg atatagaata attctgaatg gaaaagaaaa gtacaaagtc  840
tatgaagaac agagcgattt tctgcatcga ttgcaatggc ccactttgga ataa        894

SEQ ID NO: 54           moltype = DNA  length = 2771
FEATURE                 Location/Qualifiers
misc_feature            1..2771
                        note = synthetic
source                  1..2771
                        mol_type = other DNA
                        organism = synthetic construct
SEQUENCE: 54
aatgcttgcc cgggccctgc ttctgtgtgc ggtattggca ctgagtcaca cagccaaccc  60
gtgctgctca cacccatgtc agaatcgggg agtttgcatg tcagtagggt ttgaccaata  120
```

```
taagtgcgac tgtacccgga caggctttta tggagaaaat tgttctacac ccgaattttt  180
gacgaggatt aagctctttc tgaagcctac accaaataca gtccattata tcctcacgca  240
cttcaagggt ttttggaatg tcgtaaacaa cattccgttt ctgagaaatg cgataatgtc  300
ttacgtcctt acatcccgga gccaccttat tgactcaccc ccaacataca acgccgacta  360
cggatacaaa agttgggaag ctttctccaa cctgtcttac tacacgcgag cattgcctcc  420
tgtacccgac gattgcccga cgccgttggg ggtgaaagga aaaaagcagc tcccggactc  480
aaacgaaata gtagagaaat tgttgcttcg ccgaaaattt ataccagacc cgcagggtag  540
caatatgatg tttgcgttct tcgctcagca cttcactcac caattcttta agacagacca  600
caagagaggt cccgcattca cgaatggcct tggacacggc gtcgacttga accacatata  660
tggggagaca ttggccagac aaaggaaact tcgattgttt aaggatggga aaatgaaata  720
ccaaattatt gatggcgaga tgtatcctcc aacagtgaag gatacgcaag cggagatgat  780
ttatccaccg caggtaccag agcatttgcg gttcgcggtg gggcaggaag tatttggact  840
tgttcccggt ctgatgatgt acgccacaat atggctccgg gagcataatc gcgtgtgtga  900
cgtacttaag caagagcacc cggaatgggg cgacgagcaa ctttttcaaa cgagtcgact  960
gattctcatt ggggaaacga ttaaaatagt gatcgaagat tatgtgcaac atctttctgg  1020
ttaccacttt aagttgaagt tcgatcctga gctgcttttc aataaacaat tccagtatca  1080
aaacagaatc gccgcggagt tcaacacgct gtatcattgg catcccctgt tgcccgatac  1140
ttttcaaatc catgaccaga aatacaatta ccagcaattt atatataata actctatcct  1200
cctggagcat ggcattacac aattcgttga aagtttcaca aggcagatcg caggaagagt  1260
tgcgggtggc cggaatgtgc cgcctgccgt gcaaaaggta tcacaggcta gcatcgacca  1320
atcaaggcaa atgaagtacc agtcttttaa tgagtacagg aaaaggttca tgctgaagcc  1380
ttacgagagc tttgaagaac tgacgggcga aaaggaaatg tccgcggaac tggaagcgtt  1440
gtacggagat attgatgcgg tagagctcta ccccgcgctt ctggtcgaaa agccccggcc  1500
agatgccatt ttcggggaaa ccatggttga agtgggcgcc ccattcagtt tgaaaggtct  1560
gatgggtaat gtaatttgca gtccggcgta ctggaagcct tccacttttg gtggggaagt  1620
ggggtttcaa attatcaata cggcctcaat tcagtctctg atttgtaaca atgttaaggg  1680
atgtcccttt acatctttta gtgtaccgga ccccgagctt attaagaccg tgaccataaa  1740
tgcttcaagc tctagaagtg gtcttgatga tatcaacccc acagttttgc ttaaggaaag  1800
gagcacggag ctcggaagcg gagctactaa cttcagcctg ctgaagcagg ctggagacgt  1860
cgaggagaac cctggaccta gcatgaacaa ctcaaaacag ttggtctccc cagcagcggc  1920
ccttttgtcc aacacaacgt gtcagactga gaatagactc agtgtatttt ttagcgtgat  1980
ttttatgacc gtcggtatcc tgtctaactc tcttgccata gcaatattga tgaaagccta  2040
tcagcgattc cggcaaaagt ctaaggcgtc atttttgttg ttggcaagcg ggcttgtcat  2100
cacggacttt ttcgggcacc tcattaacgg agccatagcc gtgttcgttt atgcttcaga  2160
caaagagtgg atacgattcg atcagagcaa tgtgctttgc agtatctttg gcatatgtat  2220
ggtgtttagt ggattgtgtc cactcttgct tgggagcgtg atggctattg aaagatgcat  2280
cggggtgact aaacctatct ttcacagtac caaaattaca tctaagcacg tcaagatgat  2340
gttgtccggg gtgtgtcttt ttgctgtctt tattgcgttg ttgccaatac tgggccacag  2400
ggactacaaa attcaggcct cacgcacttg gtgcttctat aacactgagg atattaaaga  2460
ctgggaggat aggttttatc ttcttctttt ctcattcctc ggtctgctcg cactgggggt  2520
atccctttttg tgtaacgcta tcacaggtat caccttgttg cgcgttaaat ttaagagcca  2580
acagcatcgc caggggaggt cacatcacct cgaaatggta atacagttgc tcgcgatcat  2640
gtgtgttagt tgtatctgct ggtcaccctt cttgggatat agaataattc tgaatggaaa  2700
agaaaagtac aaagtctatg aagaacagag cgattttctg catcgattgc aatggcccac  2760
tttggaataa a                                                    2771
```

```
SEQ ID NO: 55          moltype = DNA  length = 1812
FEATURE                Location/Qualifiers
misc_feature           1..1812
                       note = synthetic
source                 1..1812
                       mol_type = other DNA
                       organism = synthetic construct
SEQUENCE: 55
atgcttgccc gggccctgct tctgtgtgcg gtattggcac tgagtcacac agccaacccg  60
tgctgctcac acccatgtca gaatcgggga gtttgcatgt cagtagggtt tgaccaatat  120
aagtgcgact gtacccggac aggcttttat ggagaaaatt gttctacacc cgaatttttg  180
acgaggatta agctctttct gaagcctaca ccaaatacag tccattatat cctcacgcac  240
ttcaagggtt tttggaatgt cgtaaacaac attccgtttc tgagaaatgc gataatgtct  300
tacgtcctta catcccggag ccaccttatt gactcacccc caacatacaa cgccgactac  360
ggatacaaaa gttgggaagc tttctccaac ctgtcttact acacgcgagc attgcctcct  420
gtacccgacg attgcccgac gccgttgggg gtgaaaggaa aaaagcagct cccggactca  480
aacgaaatag tagagaaatt gttgcttcgc cgaaaattta taccagaccc gcagggtagc  540
aatatgatgt ttgcgttctt cgctcagcac ttcactcacc aattctttaa gacagaccac  600
aagagaggtc ccgcattcac gaatggcctt ggacacggcg tcgacttgaa ccacatatat  660
ggggagacat tggccagaca aaggaaactt cgattgttta aggatgggaa aatgaaatac  720
caaattattg atggcgagat gtatcctcca acagtgaagg atacgcaagc ggagatgatt  780
tatccaccgc aggtaccaga gcatttgcgg ttcgcggtgg ggcaggaagt atttggactt  840
gttcccggtc tgatgatgta cgccacaata tggctccggg agcataatcg cgtgtgtgac  900
gtacttaagc aagagcaccc ggaatggggc gacgagcaac tttttcaaac gagtcgactg  960
attctcattg gggaaacgat taaaatagtg atcgaagatt atgtgcaaca tctttctggt  1020
taccacttta agttgaagtt cgatcctgag ctgcttttca ataaacaatt ccagtatcaa  1080
aacagaatcg ccgcggagtt caacacgctg tatcattggc atcccctgtt gcccgatact  1140
tttcaaatcc atgaccagaa atacaattac cagcaattta tatataataa ctctatcctc  1200
ctggagcatg gcattacaca attcgttgaa agtttcacaa ggcagatcgc aggaagagtt  1260
gcgggtggcc ggaatgtgcc gcctgccgtg caaaaggtat cacaggctag catcgaccaa  1320
tcaaggcaaa tgaagtacca gtcttttaat gagtacagga aaaggttcat gctgaagcct  1380
tacgagagct ttgaagaact gacgggcgaa aaggaaatgt ccgcggaact ggaagcgttg  1440
tacggagata ttgatgcggt agagctctac cccgcgcttc tggtcgaaaa gccccggcca  1500
```

-continued

```
gatgccattt tcggggaaac catggttgaa gtgggcgccc cattcagttt gaaaggtctg  1560
atgggtaatg taatttgcag tccggcgtac tggaagcctt ccacttttgg tggggaagtg  1620
gggtttcaaa ttatcaatac ggcctcaatt cagtctctga tttgtaacaa tgttaaggga  1680
tgtcccttta catcttttag tgtaccggac cccgagctta ttaagaccgt gaccataaat  1740
gcttcaagct ctagaagtgg tcttgatgat atcaacccca cagttttgct taaggaaagg  1800
agcacggagc tc                                                      1812

SEQ ID NO: 56          moltype = DNA  length = 66
FEATURE                Location/Qualifiers
misc_feature           1..66
                       note = synthetic
source                 1..66
                       mol_type = other DNA
                       organism = synthetic construct
SEQUENCE: 56
ggaagcggag ctactaactt cagcctgctg aagcaggctg gagacgtcga ggagaaccct  60
ggacct                                                             66

SEQ ID NO: 57          moltype = DNA  length = 891
FEATURE                Location/Qualifiers
misc_feature           1..891
                       note = synthetic
source                 1..891
                       mol_type = other DNA
                       organism = synthetic construct
SEQUENCE: 57
agcatgaaca actcaaaaca gttggtctcc ccagcagcgg ccctttttgtc caacacaacg  60
tgtcagactg agaatagact cagtgtattt tttagcgtga tttttatgac cgtcggtatc  120
ctgtctaact ctcttgccat agcaatattg atgaaagcct atcagcgatt ccggcaaaag  180
tctaaggcgt catttttgtt gttggcaagc gggcttgtca tcacggactt tttcgggcac  240
ctcattaacg gagccatagc cgtgttcgtt tatgcttcag acaaagagtg gatacgattc  300
gatcagagca atgtgctttg cagtatcttt ggcatatgta tggtgtttag tggattgtgt  360
ccactcttgc ttgggagcgt gatggctatt gaaagatgca tcggggtgac taaacctatc  420
tttcacagta ccaaaattac atctaagcac gtcaagatga tgttgtccgg ggtgtgtctt  480
tttgctgtct ttattgcgtt gttgccaata ctgggccaca gggactacaa aattcaggcc  540
tcacgcactt ggtgcttcta taacactgag gatattaaag actgggagga taggttttat  600
cttcttcttt tctcattcct cggtctgctc gcactggggg tatccctttt gtgtaacgct  660
atcacaggta tcaccttgtt gcgcgttaaa tttaagagcc aacagcatcg ccagggggagg  720
tcacatcacc tcgaaatggt aatacagttg ctcgcgatca tgtgtgttag ttgtatctgc  780
tggtcaccct tcttgggata tagaataatt ctgaatggaa aagaaaagta caaagtctat  840
gaagaacaga gcgattttct gcatcgattg caatggccca ctttggaata a           891

SEQ ID NO: 58          moltype = DNA  length = 4621
FEATURE                Location/Qualifiers
misc_feature           1..4621
                       note = synthetic
source                 1..4621
                       mol_type = other DNA
                       organism = synthetic construct
SEQUENCE: 58
ggttggccac tccctctctg cgcgctcgct cgctcactga ggccgggcga ccaaaggtcg  60
cccgacgccc gggctttgcc cgggcggcct cagtgagcga gcgagcgcgc agagagggag  120
tggccaactc catcactagg ggttcctaga tctgaattcg gtacccctag ttattaatag  180
taatcaatta cggggtcatt agttcatagc ccatatatgg agttccgcgt tacataactt  240
acggtaaatg gcccgcctgg ctgaccgccc aacgaccccc gcccattgac gtcaataatg  300
acgtatgttc ccatagtaac gccaataggg actttccatt gacgtcaatg ggtggactat  360
ttacggtaaa ctgcccactt ggcagtacat caagtgtatc atatgccaag tacgccccct  420
attgacgtca atgacggtaa atggcccgcc tggcattatg cccagtacat gaccttatgg  480
gactttccta cttggcagta catctacgta ttagtcatcg ctattaccat ggtcgaggtg  540
agccccacgt tctgcttcac tctccccatc tcccccccct ccccaccccc aattttgtat  600
ttatttattt tttaattatt ttgtgcagcg atgggggcgg gggggggggg ggggcgcgcg  660
ccaggcgggg cggggcgggg cgaggggcgg ggcggggcga ggcggagagg tgcggcggca  720
gccaatcaga gcggcgcgct ccgaaagttt ccttttatgg cgaggcggcg gcggcggcgg  780
ccctataaaa agcgaagcgc gcggcgggcg ggagtcgctg cgacgctgcc ttcgccccgt  840
gccccgctcc gccgccgcct cgcgccgccc gccccggctc tgactgaccg cgttactccc  900
acaggtgagc gggcgggacg gcccttctcc tccgggctgt aattagcgct tggtttaatg  960
acggcttgtt tcttttctgt ggctgcgtga aagccttgag gggctccggg agctagagcc  1020
tctgctaacc atgttcatgc cttcttcttt ttcctacagc tcctgggcaa cgtgctggtt  1080
attgtgctgt ctcatcattt tggcaaagaa ttcctcgaag atctaggcaa ctcgagaaac  1140
aaacaaactg aggtgcaggt acatccagct gacgagtccc aaataggacg aaagggagag  1200
gtgaagaata cgaccaccta ggctcgaaag agcctaaaac ataccttcct ggattccact  1260
gctatccaca aaaagaaaaa taaaaagcca ccatgcttgc ccgggccctg cttctgtgtg  1320
cggtattggc actgagtcac acagccaacc cgtgctgctc acacccatgt cagaatcggg  1380
gagtttgcat gtcagtaggg tttgaccaat ataagtgcga ctgtacccgg acaggctttt  1440
atggagaaaa ttgttctaca cccgaatttt tgacgaggat taagctcttt ctgaagccta  1500
caccaaatac agtccattat atcctcacgc acttcaaggg tttttggaat gtcgtaaaca  1560
acattccgtt tctgagaaat gcgataatgt cttacgtcct tacatcccgg agccacctta  1620
ttgactcacc cccaacatac aacgccgact acggatacaa aagttgggaa gctttctcca  1680
acctgtctta ctacacgcga gcattgcctc ctgtacccga cgattgcccg acgccgttgg  1740
```

```
gggtgaaagg aaaaaagcag ctcccggact caaacgaaat agtagagaaa ttgttgcttc  1800
gccgaaaatt tataccagac ccgcagggta gcaatatgat gtttgcgttc ttcgctcagc  1860
acttcactca ccaattcttt aagacagacc acaagagagg tcccgcattc acgaatggcc  1920
ttggacacgg cgtcgacttg aaccacatat atggggagac attggccaga caaaggaaac  1980
ttcgattgtt taaggatggg aaaatgaaat accaaattat tgatggcgag atgtatcctc  2040
caacagtgaa ggatacgcaa gcggagatga tttatccacc gcaggtacca gagcatttgc  2100
ggttcgcggt ggggcaggaa gtatttggac ttgttcccgg tctgatgatg tacgccacaa  2160
tatggctccg ggagcataat cgcgtgtgtg acgtacttaa gcaagagcac ccggaatggg  2220
gcgacgagca actttttcaa acgagtcgac tgattctcat tggggaaacg attaaaatag  2280
tgatcgaaga ttatgtgcaa catctttctg gttaccactt taagttgaag ttcgatcctg  2340
agctgctttt caataaacaa ttccagtatc aaaacagaat cgccgcggag ttcaacacgc  2400
tgtatcattg gcatcccctg ttgcccgata cttttcaaat ccatgaccag aaatacaatt  2460
accagcaatt tatatataat aactctatcc tcctggagca tggcattaca caattcgttg  2520
aaagtttcac aaggcagatc gcaggaagag ttgcgggtgg ccggaatgtg ccgcctgccg  2580
tgcaaaaggt atcacaggct agcatcgacc aatcaaggca aatgaagtac cagtctttta  2640
atgagtacag gaaaaggttc atgctgaagc cttacgagag ctttgaagaa ctgacgggcg  2700
aaaaggaaat gtccgcggaa ctggaagcgt tgtacggaga tattgatgcg gtagagctct  2760
accccgcgct tctggtcgaa aagccccggc cagatgccat tttcggggaa accatggttg  2820
aagtgggcgc cccattcagt ttgaaaggtc tgatgggtaa tgtaatttgc agtccggcgt  2880
actggaagcc ttccactttt ggtggggaag tggggtttca aattatcaat acggcctcaa  2940
ttcagtctct gatttgtaac aatgttaagg gatgtccctt tacatctttt agtgtaccgg  3000
accccgagct tattaagacc gtgaccataa atgcttcaag ctctagaagt ggtcttgatg  3060
atatcaaccc cacagttttg cttaaggaaa ggagcacgga gctcggaagc ggagctacta  3120
acttcagcct gctgaagcag gctggagacg tcgaggagaa ccctggacct agcatgaaca  3180
actcaaaaca gttggtctcc ccagcagcgg ccccttttgtc caacacaacg tgtcagactg  3240
agaatagact cagtgtattt tttagcgtga ttttatgac cgtcggtatc ctgtctaact  3300
ctcttgccat agcaatattg atgaaagcct atcagcgatt ccggcaaaag tctaaggcgt  3360
catttttgtt gttggcaagc gggcttgtca tcacggactt tttcgggcac ctcattaacg  3420
gagccatagc cgtgttcgtt tatgcttcag acaaagagtg gatacgattc gatcagagca  3480
atgtgctttg cagtatcttt ggcatatgta tggtgtttag tggattgtgt ccactcttgc  3540
ttgggagcgt gatggctatt gaaagatgca tcggggtgac taaacctatc tttcacagta  3600
ccaaaattac atctaagcac gtcaagatga tgttgtccgg ggtgtgtctt tttgctgtct  3660
ttattgcgtt gttgccaata ctgggccaca gggactacaa aattcaggcc tcacgcactt  3720
ggtgcttcta taacactgag gatattaaag actgggagga taggttttat cttcttcttt  3780
tctcattcct cggtctgctc gcactggggg tatccctttt gtgtaacgct atcacaggta  3840
tcaccttgtt gcgcgttaaa tttaagagcc aacagcatcg ccaggggagg tcacatcacc  3900
tcgaaatggt aatacagttg ctcgcgatca tgtgtgttag ttgtatctgc tggtcaccct  3960
tcttgggata tagaataatt ctgaatggaa aagaaaagta caaagtctat gaagaacaga  4020
gcgattttct gcatcgattg caatggccca ctttggaata aaaacaaaca aactgagatg  4080
caggtacatc ccactgatga gtcccaaata ggacgaaagg gagaggtgaa gaatacgacc  4140
acctaggctc gaaagagcct aaaacatacc ttctgggatt ccactgctat ccacaaaaag  4200
aaaaataaaa agcggccgct gcaggagtcg gtcgactaga gctcgctgat cagcctcgac  4260
tgtgccttct agttgccagc catctgttgt ttgcccctcc cccgtgcctt ccttgaccct  4320
ggaaggtgcc actcccactg tcctttccta ataaaatgag gaaattgcat cgcattgtct  4380
gagtaggtgt cattctattc tggggggtgg ggtggggcag gacagcaagg gggaggattg  4440
ggaagacaat agcaggcatg ctggggagag atctaggaac ccctagtgat ggagttggcc  4500
actccctctc tgcgcgctcg ctcgctcact gaggccgccc gggcaaagcc cgggcgtcgg  4560
gcgacctttg gtcgcccggc ctcagtgagc gagcgagcgc gcagagaggg agtggccaac  4620
c                                                                  4621
```

```
SEQ ID NO: 59          moltype = DNA  length = 122
FEATURE                Location/Qualifiers
misc_feature           1..122
                       note = synthetic
source                 1..122
                       mol_type = other DNA
                       organism = synthetic construct
SEQUENCE: 59
ctgaggtgca ggtacatcca gctgacgagt cccaaatagg acgaaaggga gaggtgaaga  60
atacgaccac ctaggctcga aagagcctaa aacatacctt cctggattcc actgctatcc  120
ac                                                                 122
```

```
SEQ ID NO: 60          moltype = DNA  length = 1812
FEATURE                Location/Qualifiers
misc_feature           1..1812
                       note = synthetic
source                 1..1812
                       mol_type = other DNA
                       organism = synthetic construct
SEQUENCE: 60
atgcttgccc gggccctgct tctgtgtgcg gtattggcac tgagtcacac agccaacccg  60
tgctgctcac acccatgtca gaatcgggga gtttgcatgt cagtagggtt tgaccaatat  120
aagtgcgact gtacccggac aggcttttat ggagaaaatt gttctacacc cgaatttttg  180
acgaggatta agctctttct gaagcctaca ccaaatacag tccattatat cctcacgcac  240
ttcaagggtt tttggaatgt cgtaaacaac attccgtttc tgagaaatgc gataatgtct  300
tacgtcctta catcccggag ccaccttatt gactcacccc caacatacaa cgccgactac  360
ggatacaaaa gttgggaagc tttctccaac ctgtcttact acacgcgagc attgcctcct  420
gtacccgacg attgcccgac gccgttgggg gtgaaaggaa aaaagcagct cccggactca  480
aacgaaatag tagagaaatt gttgcttcgc cgaaaattta taccagaccc gcagggtagc  540
```

```
aatatgatgt ttgcgttctt cgctcagcac ttcactcacc aattctttaa gacagaccac  600
aagagaggtc ccgcattcac gaatggcctt ggacacggcg tcgacttgaa ccacatatat  660
ggggagacat tggccagaca aaggaaactt cgattgttta aggatgggaa aatgaaatac  720
caaattattg atggcgagat gtatcctcca acagtgaagg atacgcaagc ggagatgatt  780
tatccaccgc aggtaccaga gcatttgcgg ttcgcggtgg ggcaggaagt atttggactt  840
gttcccggtc tgatgatgta cgccacaata tggctccggg agcataatcg cgtgtgtgac  900
gtacttaagc aagagcaccc ggaatggggc gacgagcaac tttttcaaac gagtcgactg  960
attctcattg gggaaacgat taaaatagtg atcgaagatt atgtgcaaca tctttctggt  1020
taccacttta agttgaagtt cgatcctgag ctgcttttca ataaacaatt ccagtatcaa  1080
aacagaatcg ccgcggagtt caacacgctg tatcattggc atcccctgtt gcccgatact  1140
tttcaaatcc atgaccagaa atacaattac cagcaattta tatataataa ctctatcctc  1200
ctggagcatg gcattacaca attcgttgaa agtttcacaa ggcagatcgc aggaagagtt  1260
gcgggtggcc ggaatgtgcc gcctgccgtg caaaaggtat cacaggctag catcgaccaa  1320
tcaaggcaaa tgaagtacca gtcttttaat gagtacagga aaaggttcat gctgaagcct  1380
tacgagagct ttgaagaact gacgggcgaa aaggaaatgt ccgcggaact ggaagcgttg  1440
tacggagata ttgatgcggt agagctctac cccgcgcttc tggtcgaaaa gccccggcca  1500
gatgccattt tcggggaaac catggttgaa gtgggcgccc cattcagttt gaaaggtctg  1560
atgggtaatg taatttgcag tccggcgtac tggaagcctt ccacttttgg tggggaagtg  1620
gggtttcaaa ttatcaatac ggcctcaatt cagtctctga tttgtaacaa tgttaaggga  1680
tgtcccttta catcttttag tgtaccggac cccgagctta ttaagaccgt gaccataaat  1740
gcttcaagct ctagaagtgg tcttgatgat atcaacccca cagttttgct taaggaaagg  1800
agcacggagc tc                                                      1812
```

```
SEQ ID NO: 61          moltype = DNA  length = 66
FEATURE                Location/Qualifiers
misc_feature           1..66
                       note = synthetic
source                 1..66
                       mol_type = other DNA
                       organism = synthetic construct
SEQUENCE: 61
ggaagcggag ctactaactt cagcctgctg aagcaggctg gagacgtcga ggagaaccct  60
ggacct                                                             66
```

```
SEQ ID NO: 62          moltype = DNA  length = 891
FEATURE                Location/Qualifiers
misc_feature           1..891
                       note = synthetic
source                 1..891
                       mol_type = other DNA
                       organism = synthetic construct
SEQUENCE: 62
agcatgaaca actcaaaaca gttggtctcc ccagcagcgg ccctttttgtc caacacaacg  60
tgtcagactg agaatagact cagtgtattt tttagcgtga tttttatgac cgtcggtatc  120
ctgtctaact ctcttgccat agcaatattg atgaaagcct atcagcgatt ccggcaaaag  180
tctaaggcgt catttttgtt gttggcaagc gggcttgtca tcacggactt tttcgggcac  240
ctcattaacg gagccatagc cgtgttcgtt tatgcttcag acaaagagtg gatacgattc  300
gatcagagca atgtgctttg cagtatcttt ggcatatgta tggtgtttag tggattgtgt  360
ccactcttgc ttgggagcgt gatggctatt gaaagatgca tcggggtgac taaacctatc  420
tttcacagta ccaaaattac atctaagcac gtcaagatga tgttgtccgg ggtgtgtctt  480
tttgctgtct ttattgcgtt gttgccaata ctgggccaca gggactacaa aattcaggcc  540
tcacgcactt ggtgcttcta taacactgag gatattaaag actgggagga taggttttat  600
cttcttcttt tctcattcct cggtctgctc gcactggggg tatccctttt gtgtaacgct  660
atcacaggta tcaccttgtt gcgcgttaaa tttaagagcc aacagcatcg ccaggggagg  720
tcacatcacc tcgaaatggt aatacagttg ctcgcgatca tgtgtgttag ttgtatctgc  780
tggtcaccct tcttgggata tagaataatt ctgaatggaa aagaaaagta caaagtctat  840
gaagaacaga gcgattttct gcatcgattg caatggccca ctttggaata a           891
```

```
SEQ ID NO: 63          moltype = DNA  length = 122
FEATURE                Location/Qualifiers
misc_feature           1..122
                       note = synthetic
source                 1..122
                       mol_type = other DNA
                       organism = synthetic construct
SEQUENCE: 63
ctgagatgca ggtacatccc actgatgagt cccaaatagg acgaaaggga gaggtgaaga  60
atacgaccac ctaggctcga aagagcctaa aacatacctt ctgggattcc actgctatcc  120
ac                                                                 122
```

```
SEQ ID NO: 64          moltype = DNA  length = 168
FEATURE                Location/Qualifiers
misc_feature           1..168
                       note = synthetic
source                 1..168
                       mol_type = other DNA
                       organism = synthetic construct
SEQUENCE: 64
ctcgaggcga tcgcaaacaa acaaagctgt caccggatgt gctttccggt ctgatgagtc  60
```

```
cgttgtccaa taccagcatc gtcttgatgc ccttggcagt ggatggggac ggaggacgaa  120
acagcaaaaa gaaaaataaa aatttttttt ttaattaatc ttgggccc              168

SEQ ID NO: 65          moltype = DNA  length = 139
FEATURE                Location/Qualifiers
misc_feature           1..139
                       note = synthetic
source                 1..139
                       mol_type = other DNA
                       organism = synthetic construct
SEQUENCE: 65
atggccggca tggtcccagc ctcctcgctg gcgccggctg ggcaaccaca taccagccga  60
aaggcccttg gcaggtgggc gaatgggacg cacaaatctc tctagcttcc cagagagaag  120
cgagagaaaa gtggctctc                                               139

SEQ ID NO: 66          moltype = DNA  length = 135
FEATURE                Location/Qualifiers
misc_feature           1..135
                       note = synthetic
source                 1..135
                       mol_type = other DNA
                       organism = synthetic construct
SEQUENCE: 66
atggccggca tggtcccagc ctcctcgctg gcgccggctg ggcaatgcta taatcgcgtg  60
gatatggcac gcaagtttct accgggcacc gtaaatgtcc gactagtagc gaatgggacg  120
cacaaatctc tctag                                                   135

SEQ ID NO: 67          moltype = DNA  length = 134
FEATURE                Location/Qualifiers
misc_feature           1..134
                       note = synthetic
source                 1..134
                       mol_type = other DNA
                       organism = synthetic construct
SEQUENCE: 67
caaacaaaca aaggcgcgtc ctggattcgt ggtaaaacat accagatttc gatctggaga  60
ggtgaagaat acgaccacct gtagtatcca gctgatgagt cccaaatagg acgaaacgcg  120
ctaaacaaac aaac                                                    134

SEQ ID NO: 68          moltype = DNA  length = 104
FEATURE                Location/Qualifiers
misc_feature           1..104
                       note = synthetic
source                 1..104
                       mol_type = other DNA
                       organism = synthetic construct
SEQUENCE: 68
gagagaatct tctttctgtc tataaaagag agaatcttct ttctgtctat aaaagagaga  60
atcttctttc tgtctataaa agagagaatc ttctttctgt ctat                   104

SEQ ID NO: 69          moltype = DNA  length = 124
FEATURE                Location/Qualifiers
misc_feature           1..124
                       note = synthetic
source                 1..124
                       mol_type = other DNA
                       organism = synthetic construct
SEQUENCE: 69
gcggccgcgc tagcacgggt cctgatacca gcgtgagcgg agagaatctt ctttctgtct  60
attagtgaag ccacagatgt aatagacaga aagaagattc tctccgccta cgcccttggc  120
agca                                                               124

SEQ ID NO: 70          moltype = DNA  length = 21
FEATURE                Location/Qualifiers
misc_feature           1..21
                       note = synthetic
source                 1..21
                       mol_type = other DNA
                       organism = synthetic construct
SEQUENCE: 70
tatttaggga aggaactcag g                                            21

SEQ ID NO: 71          moltype = DNA  length = 21
FEATURE                Location/Qualifiers
misc_feature           1..21
                       note = synthetic
source                 1..21
                       mol_type = other DNA
                       organism = synthetic construct
```

```
SEQUENCE: 71
aatacaaacc tgaacaatgg g                                           21

SEQ ID NO: 72          moltype = DNA  length = 21
FEATURE                Location/Qualifiers
misc_feature           1..21
                       note = synthetic
source                 1..21
                       mol_type = other DNA
                       organism = synthetic construct
SEQUENCE: 72
agttgagcca agatcgacac g                                           21

SEQ ID NO: 73          moltype = DNA  length = 21
FEATURE                Location/Qualifiers
misc_feature           1..21
                       note = synthetic
source                 1..21
                       mol_type = other DNA
                       organism = synthetic construct
SEQUENCE: 73
atctatacta tttagggaag g                                           21

SEQ ID NO: 74          moltype = DNA  length = 21
FEATURE                Location/Qualifiers
misc_feature           1..21
                       note = synthetic
source                 1..21
                       mol_type = other DNA
                       organism = synthetic construct
SEQUENCE: 74
agatcgacac gttaactctt g                                           21

SEQ ID NO: 75          moltype = DNA  length = 21
FEATURE                Location/Qualifiers
misc_feature           1..21
                       note = synthetic
source                 1..21
                       mol_type = other DNA
                       organism = synthetic construct
SEQUENCE: 75
taggtacagc tagatatttg c                                           21

SEQ ID NO: 76          moltype = DNA  length = 21
FEATURE                Location/Qualifiers
misc_feature           1..21
                       note = synthetic
source                 1..21
                       mol_type = other DNA
                       organism = synthetic construct
SEQUENCE: 76
tcatgacgtc ttaacaaacg g                                           21

SEQ ID NO: 77          moltype = DNA  length = 21
FEATURE                Location/Qualifiers
misc_feature           1..21
                       note = synthetic
source                 1..21
                       mol_type = other DNA
                       organism = synthetic construct
SEQUENCE: 77
taacaaacgg taaagaaggt g                                           21

SEQ ID NO: 78          moltype = DNA  length = 21
FEATURE                Location/Qualifiers
misc_feature           1..21
                       note = synthetic
source                 1..21
                       mol_type = other DNA
                       organism = synthetic construct
SEQUENCE: 78
atcaatacga gtcggaaagc g                                           21

SEQ ID NO: 79          moltype = DNA  length = 21
FEATURE                Location/Qualifiers
misc_feature           1..21
                       note = synthetic
source                 1..21
                       mol_type = other DNA
```

-continued

```
                      organism = synthetic construct
SEQUENCE: 79
atctaggaca ctcttcgtct g                                         21

SEQ ID NO: 80         moltype = RNA  length = 13
FEATURE               Location/Qualifiers
misc_feature          1..13
                      note = Synthetic
source                1..13
                      mol_type = other RNA
                      organism = synthetic construct
SEQUENCE: 80
aaaaaaaaaa aaa                                                  13
```

RIBOSWITCH MODULATED GENE THERAPY FOR RETINAL DISEASES

CROSS-REFERENCE TO RELATED APPLICATIONS

This Application is a continuation of U.S. application Ser. No. 16/492,878, filed Sep. 10, 2019, which is the U.S. national stage entry of PCT International Application No. PCT/US2018/021719 filed on Mar. 9, 2018, which claims priority to U.S. Provisional Application No. 62/469,705 filed on Mar. 10, 2017. The entire content of each of the above-referenced applications is incorporated by reference.

STATEMENT REGARDING FEDERALLY SPONSORED RESEARCH

N/A

BACKGROUND OF THE INVENTION

Age-Related Macular Degeneration (AMD) and glaucoma are leading causes of vision loss worldwide. AMD is a common eye disease among people age 50 and older. In AMD, there is damage to the macula, a small area made up of millions of light-sensing cells near the center of the retina and the part of the eye needed for sharp, central vision, and the ability to see objects that are straight ahead. Macular damage is caused by the formation of deposits called drusen, and in some cases, the growth of abnormal blood vessels, under the retina.

Glaucoma is a group of diseases in which the eye's optic nerve is damaged resulting in vision loss and blindness. The hallmark of glaucoma is increased intraocular pressure related to build-up of fluid (aqueous humor). It some patients the disease is genetic. In other patients, inflammation in the eye is thought to be involved in glaucoma.

Neither AMD nor glaucoma can be prevented. There is no treatment for early AMD in which there is no symptoms or loss of vision. Advanced AMD is treated with biologics. Glaucoma is often treated with prostaglandin eye drops. Current treatments are invasive and expensive and burdensome on the patient and clinic, requiring monthly eye injections (AMD) or daily eye drop administration.

Ocular gene therapies have the potential to profoundly improve the quality of life in patients with inherited retinal disease. Several factors make the eye an ideal organ for gene-replacement therapy. The eye is accessible, it is a compartmentalized, privileged site. This in turn means that immunologically the eyes are able to tolerate the introduction of foreign proteins/antigens without eliciting an inflammatory immune response. Clinical trials can take advantage of contralateral controls. For this reason, gene therapies for eye diseases are in development.

In this regard, recombinant adeno-associated virus (rAAV) vectors have emerged as promising tools for mediating gene therapy for diseases of the retina. Effectively controlling gene expression levels following vector delivery is paramount to the success of potential gene therapies, where uncontrolled over-expression of the therapeutic transgenes can lead to toxicity. Traditionally, inducible promoter systems have been employed. Unfortunately, due to the limited coding capacity of AAV, and the large size of the regulatory elements required to make such systems work effectively, inclusion of traditional promoters is not feasible.

Riboswitches are a possible alternative. Riboswitches are specific regulatory components of an mRNA molecule that bind and target small target molecules thereby regulating the expression of the riboswitch-containing mRNA's protein product in a cis-fashion. Thus, an mRNA that contains a riboswitch is directly involved in regulating its own activity, in response to the concentrations of its target molecule. Some riboswitches are "self-targeting", which means that can regulate their own expression. The switch includes an RNA element that can adapt to one of two mutually exclusive secondary structures. One of these structures is a signal for gene expression to be "on" and the other conformation turns the gene "off."

However, often toxic concentrations of ligand are necessary to "flip the switch" to turn on or off gene expression. Consequently, a goal of current research is to improve these regulatory devices toward efficiency, improved regulatory parameters, and clinical applicability. The subject of this invention are riboswitches that can turn on or off gene expression in the retina for use in ocular gene therapy.

SUMMARY OF THE INVENTION

The present invention overcomes the aforementioned drawbacks by providing constructs, kits and methods of regulating a transgene expression using a modified riboswitch which works by a dual mechanism of gene silencing. The invention provides a distinct and improved design over prior riboswitches with its dual mechanism for gene silencing, thereby allowing for better control of expression of the transgene. Novel modified riboswitches are described in more detail herein, including a self-targeting ligand inactivating microRNA (SLIM) switch which is an ON-type switch that mediates an increase in gene expression in the presence of the ligand. Compositions and methods of using this technology to treat AMD are provided herein. Specifically, this SLIM switch can be used to intermittently switch on expression of transgene, for example, a VEGF inhibitor. Further embodiments of SLIM switches that can be used to treat glaucoma. Compositions and method of use of this technology are contemplated for the treatment of glaucoma, where it would be beneficial to intermittently turn off, or decrease expression of the prostaglandin in the eye of a patient.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2B is a schematic showing the design and functioning of a SLIM switch with and without ligand.

FIG. 2C is a schematic representing the rAAV vector encoding Aflibercept (a VEGF inhibitor), with the modified switch (smiRNA) and target miRNA sequences (miRT).

FIG. 3 is a schematic of on-type aptamers that can be used in the design of SLIM switches.

FIG. 4 depicts the components of a Theo-SLIM construct.

FIG. 5 is a sequence of an exemplary construct containing Aflibercept (a VEGF inhibitor), Theo-SLIM and three miRNA target sites.

FIGS. 14A, 14B, 14C, 14D, 14E, 14F, 14G, 14H, 14I, 14J, 14K, and 14L are representative fluorescein angiography images of CNV lesions. Leakage from CNV lesions was assessed 7 days following laser injury. Representative FA images taken 5 minutes after fluorescein injection for mice injected with either (A-C) rAAV2 [MAX].smCBA-Eylea, (D-F) rAAV2 [MAX].smCBA-Eylea-1x-TC45+standard diet, (G-I) rAAV2 [MAX].smCBA-Eylea-1x-TC45+tetracycline diet or PBS (n=16-20 lesions per group). Images of 3 mice per group with red arrows indicating site of the laser injury.

FIGS. 16A and 16B are exemplary sequences of the recombinant VEGF inhibitor cDNA (SEQ ID NO:18), and complete AAV vector comprising SLIM Eylea (SEQ ID NO: 19).

FIGS. 18A, 18B, and 18C are exemplary 6-S-Folinic Acid-responsive miRNA Switches (Eylea CDS target) (SEQ ID NOs: 21-25), Theophylline-responsive miRNA switches (Eylea CDS target) (SEQ ID NOs: 26-30), tetracycline-responsive miRNA switches (Eylea CDS target) (SEQ ID NO:31-35), and the soluble fms-like tyrosine kinase 1 (sFLT1) VEGF inhibitor cDNA (SEQ ID NO:36) that can be used with the SLIM switches to treat AMD.

FIGS. 19A and 19B show exemplary sequences for 6S-Folinic Acid-responsive miRNA SLIM Switches (sFLT1 CDS target) including SEQ ID NOs: 37-41, theophylline-responsive miRNA SLIM switches (sFLT1-CDS target) including SEQ ID NOs: 42-46, and tetracycline-responsive miRNA switches (sFLT1-CDS target) SEQ ID NOs: 47-51.

FIGS. 23A, 23B, 23C, 23D, and 23E are exemplary sequences for use in the present invention, including a codon optimized PTGS2 sequence (SEQ ID NO:52), a codon optimized PTGFR (SEQ ID NO:53), PTGS2-P2-PTGFR sequence (SEQ ID NO:54), and complete AAV expression cassette for PDG2alpha biosynthesis (SEQ ID NO:58). Also included are additional riboswitches that can be used in the practice of the present invention (SEQ ID NO:64-67).

DETAILED DESCRIPTION OF THE INVENTION

The present disclosure provides modified riboswitches (e.g., modified miRNA switches) and systems containing said modified riboswitches for use in the treatment of diseases, specifically eye diseases, and more specifically AMD and glaucoma. The present invention aims to provide novel systems to regulate gene expression in the eye, using novel modified microRNA (riboswitches) as a regulatory tool. Such genetic constructs, and kits or methods utilizing same, may be of use in controlling gene expression, for example in the production of recombinant proteins or transgenes involved in the regulation of specific compounds, for example, prostaglandins in the eye.

Such RNA-based systems (riboswitches) offer three distinct advantages over inducible promoter systems. First, they have a small genetic footprint (~100 bp) and so can be easily incorporated within the rAAV vector genome without sacrificing significant amounts of coding capacity. Second, these devices act in cis, limiting the likelihood of an immune response as no protein cofactors are required for functionality. Last, the aptamer domain of a riboswitch can be engineered to respond to almost any activating ligand, including proteins, small molecule drugs or ions.

One embodiment of this technology is to modulate expression of transgenes involved in prostaglandin F2α synthesis in the eye to regulate intraocular pressure in glaucoma patients. A second embodiment is to modulate the expression of an anti-VEGF recombinant fusion protein in the eye, namely Aflibercept (Eylea) in order to prevent choroidal neovascularization (CNV).

The technology in some embodiments uses constructs including modified riboswitches, which are ligand-controlled gene regulatory elements that allow for either switching on or off a transgene of interest in order to regulate transgene expression. The mechanisms by which riboswitches function include, without limitation, the ability to function as a ribozyme and cleave itself if a sufficient concentration of its ligand is present, the ability to fold the mRNA in such a way the ribosomal binding site is inaccessible and prevents translation from occurring, and/or the ability to affect the splicing of the pre-mRNA molecule. Embodiments comprising the modified riboswitches and constructs or cassettes containing such riboswitches are contemplated herein.

MicroRNAs are a class of non-coding RNAs that play key roles in the regulation of gene expression. Acting at the post-transcriptional level, microRNA (miRNA) genes are transcribed by RNA polymerase II as large primary transcripts (pri-mRNA) that are processed by a protein complex containing the RNase III enzyme Drosha, to form a precursor microRNA (pre-microRNA). In the present invention, the pri-microRNA have been designed to be processed into a pre-mRNA that can act as a silencing RNA to silence gene expression.

Figure 1:
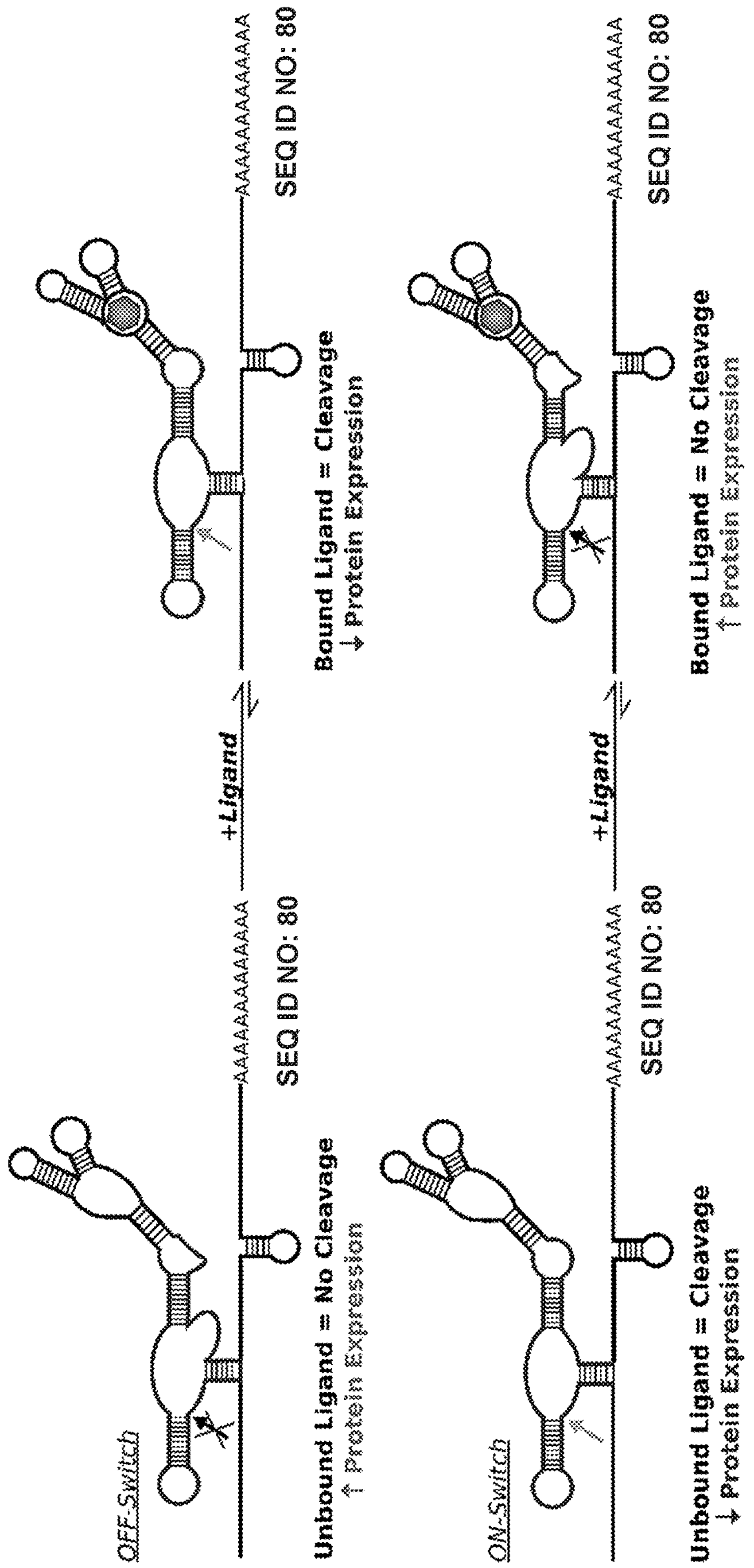
FIG. 1 is a schematic demonstrating the OFF-Switch and ON-Switch riboswitches.

Riboswitches are divided into two parts: an aptamer and an expression platform. The aptamer is a "sensor" to which a target small molecule ligand binds; the expression platform undergoes structural changes in response to the changes in the aptamer sensor. Binding of the aptamer domain causes conformational changes within the expression platform, this conformational change regulates gene expression by turning the gene off or on. This is illustrated in FIG. 1. The aptamer is shown in blue; the expression platform, in red; the ligand in green. Often toxic concentrations of ligand are necessary to "flip the switch". However, the present invention provides modified riboswitches that can turn on or off gene expression in the retina for use in ocular gene therapy using non-toxic levels of ligand.

A number of exemplary riboswitches are described herein, namely a self-targeting ligand inactivating microRNA (SLIM) embodiments. A self-targeting ligand inactivating microRNA (SLIM) is an ON-type switch that mediates an increase in gene expression in the presence of the ligand (See, e.g., FIGS. 2A and 2B). Compositions and methods of using this technology to treat AMD and Glaucoma are provided herein. Specifically, this SLIM system can be used to intermittently switch on expression of the VEGF inhibitor. Compositions and methods of use of this technology are contemplated for the treatment of glaucoma, where it would be beneficial to intermittently turn off or lower expression of the prostaglandin in the eye of a patient are contemplated. Both are described in more detail below.

SLIM: ON-Type Modified Riboswitch for Modifying Gene Expression

The present invention in one embodiment provides a self-targeting ligand inactivating microRNA (SLIM) switch which is an ON type riboswitch that can be incorporated into an expression construct to regulate expression of a transgene of interest. The SLIM switch (smiRNA in FIGS. 2A and B) requires the basal region of a pri-miRNA to be replaced with an aptamer that can bind to a target ligand. This sequence is cloned into either the 3'- or 5' untranslated region of an expression construct. Binding of the ligand alters the conformation of the aptamer and pri-miRNA, resulting in non-cleavage of the pri-miRNA by Drosha. A target miRNA sequence is cloned into either the 3' or 5' untranslated region which allows for a second level of regulation, in which the pri-miRNA when cleaved in the absence of ligand is processed into a miRNA that can bind to the target miRNA sequence and prevent transcription. Once the SLIM switch is incorporated within an expression construct, the transgene expression is turned off when ligand is not present, and is turned on once the ligand binds to the aptamer.

SLIM switches function by regulating gene expression at the post-transcriptional level. In conditions in which the activating ligand is absent, the pri-miRNA will be cleaved by Drosha from the nascent transcript. This miRNA will be processed and act as a second mechanism of gene silencing, through binding of the complementary target sites. When the activating ligand is present, gene expression is unaltered and the gene is expressed.

In one embodiment, an exogenous nucleic acid construct for regulating expression of a transgene is provided. The construct encodes (a) a transgene, (b) a smiRNA switch (SLIM switch) located within the untranslated region of the transgene, wherein the smiRNA switch comprises an aptamer domain capable of binding to a ligand and a pri-miRNA sequence, and (c) at least one miRNA target sequence complementary to at least a portion of the pri-miRNA. The miRNA switch regulates expression of the transgene by both (1) regulation of the cleavage of the mRNA (which removes either the poly-A tail or 5'-cap destabilizing the RNA), and (2) regulating cleavage of the pri-miRNA from the smiRNA, wherein at least a portion of the cleaved pri-miRNA is processed and binds to the at least one miRNA target sequences silencing the transgene expression.

As discussed above, in the absence of ligand, the pri-miRNA is cleaved from the transcript and binds to the at least one miRNA target sequence which silences the transgene. This is depicted in FIG. 2B. In some embodiments, the at least one miRNA target sequence complementary to at least a portion of the pri-miRNA (c) discussed above is encompassed in the transgene (as depicted in the bottom figure of FIG. 2B). In other words, the SLIM switch can be generated toward the transgene itself.

In a preferred embodiment, the heterologous self-targeting ligand inactivating microRNA (SLIM) switch comprises (a) a target gene of interest, (b) at least one smiRNA switch located within the untranslated region of the transgene, wherein the smiRNA switch comprises an aptamer domain capable of binding to a ligand and a pri-miRNA, wherein the smiRNA switch regulates expression of the transgene by both (1) regulation of the cleavage of the mRNA of the transgene, and (b) regulating cleavage of the pri-miRNA from the smiRNA, wherein at least a portion of the cleaved pri-miRNA binds to a portion of the transgene (in other words, a portion of the transgene acts as the miRNA targeting sequence) silencing the transgene expression. Suitable riboswitches are described in FIGS. 18 and 19, which also include the portion of the Eylea transgene or Flt1 transgene each riboswitch targets (e.g. SLIM switch for Eylea Target 1 (e.g., SEQ ID NO: 21, or 26 or 31) targets a portion of Eylea found in Eylea target 1 (SEQ ID NO:70), SLIM switch for Target 2 (e.g. SEQ ID NO:22, 27, 32) target Eylea Target 2 (SEQ ID NO:71) and so forth (e.g. SLIM switch for Eylea 3 targets Eylea Target 3, SLIM switch for Eylea 4 targets Eylea Target 4, SLIM switch for Eylea Target 5 targets Eylea Target 5, SLIM switch for Flt1 Target 1 targets Flt1 Target 1, etc.). One or more SLIM switches can be combined within the exogenous expression constructs for use in the methods described herein (e.g., SLIM switch for Target 1, Target 2, Target 3, Target 4, and Target 5 of Elyea or Sflt1 can be combined in any combination for a construct to target (e.g. SLIM 1 and 2; SLIM 1 and 3; SLIM 1 and 4; SLIM 1 and 5; SLIM 2 and 3; SLIM 2 and 4; SLIM 2 and 5; SLIM 3 and 4; SLIM 3 and 5; SLIM 4 and 5; SLIM 1, 2, and 3; SLIM 1, 2 and 4; SLIM 1, 2 and 5; SLIM 1, 3, and 4; SLIM 1, 3 and 5; SLIM 1, 4 and 5; SLIM 2, 3 and 4; SLIM 2, 3 and 5; SLIM 2, 4 and 5; SLIM 3, 4 and 5; SLIM 1, 2, 3, and 4; SLIM 1, 2, 3 and 5; SLIM 2, 3, 4 and 5; and SLIM 1, 2, 3, 4 and 5) of the SLIM found in FIGS. 18-19.

In one embodiment, an exogenous nucleic acid construct for regulating expression of a transgene by modulating the mRNA of the transgene is provided. The nucleic acid encoding: (a) a target gene of interest, (b) at least one smiRNA switch located within the untranslated region of the transgene, wherein the smiRNA switch comprises an aptamer domain capable of binding to a ligand and a pri-miRNA, wherein the smiRNA switch regulates expression of the transgene by both (1) regulation of the cleavage of the mRNA of the transgene, and (b) regulating cleavage of the pri-miRNA from the smiRNA, wherein at least a portion of the cleaved pri-miRNA binds to a portion of the transgene (as a miRNA targeting sequence) silencing the transgene expression. In a preferred embodiment, the exogenous nucleic acid construct is a AAV viral vector.

In some embodiments, the SLIM switch generated against Eylea or sFlt1 are used for the treatment of AMD as shown in the sequences described in FIGS. 18 and 19.

Figure 2A:
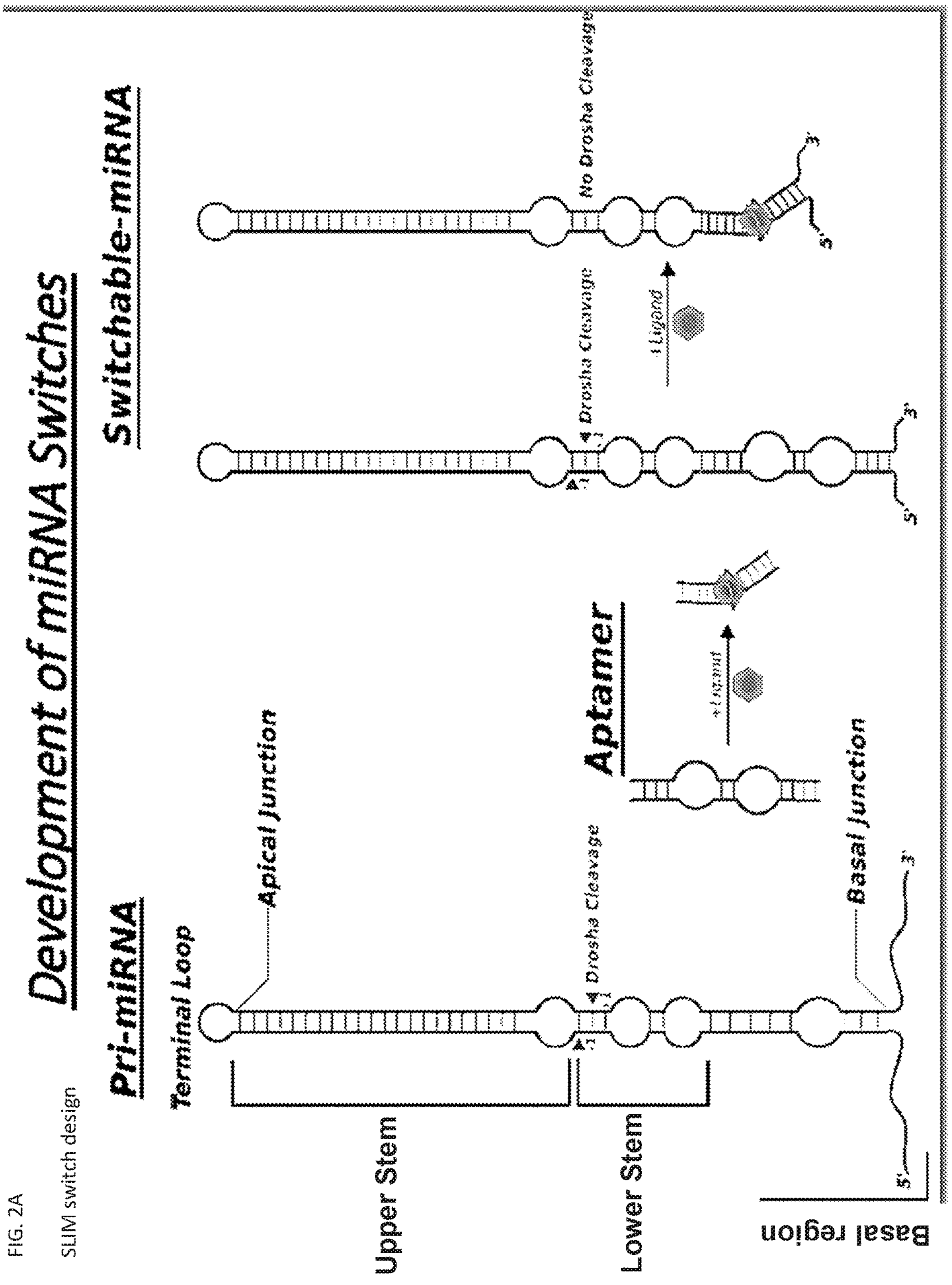
FIG. 2A is a schematic representing the development of a SLIM switch (e.g. switchable miRNA) using a pri-miRNA and an aptamer.

In one embodiment, an exogenous nucleic acid construct encodes: the SLIM switch, transgene, and at least one target miRNA sequence. Design of such SLIM switches is depicted in FIG. 2A. In one example, a suitable SLIM switch (smiRNA) encodes an aptamer domain and a pri-miRNA. Suitable aptamer domain is adapted from the aptamer domain of an ON-type riboswitch known in the art, and include but are not limited to, for example, L2Bulge18tc (for example, but not limited to, SEQ ID NO:12), K19 (For example, SEQ ID NO: 15), L2Bulge9 (for example, SEQ ID NO:11), among others. Suitable aptamer domains are depicted in FIG. 3 and described in the specification below.

Suitable SLIM switches include, but are not limited to our developed Theo-SLIM (SEQ ID NO: 1) which is depicted in FIG. 3 (smiRNA), and Tet-SLIM (SEQ ID NO:17) as described herein. These SLIM switches have been engineered as to not cross-react with any genes in the human genome, and thus should not cause any off-target effects.

Additional SLIM switches are depicted in FIGS. 18-23.

The term "exogenous" as it refers to nucleic acid is foreign to (not normally found in nature in) the prokaryotic host cell, or a recombinant nucleic acid that is not normally found in the prokaryotic host cell. In some embodiments, the exogenous nucleic acid sequence is a heterologous sequence comprising sequences from a number of different sources or organisms. The term exogenous also encompasses a construct that include sequences from a different species than the species the construct will be used. For example, a rAAV construct of the present invention will include not only endogenous AAV sequences, but exogenous sequences from human or other sources that are not native to the AAV virus.

The nucleic acid constructs provided herein are synthetic engineered constructions containing non-naturally occurring sequences.

The term "transgene" and "target gene of interest" are used interchangeably to refer to an exogenous gene which is to be expressed in the desired cell by use of the constructs of the present invention.

Further, suitable aptamers can be designed against various ligands and incorporated into the SLIM switches by linking the aptamer to a pri-miRNA sequence (See, e.g., FIG. 2A).

In some embodiments, the constructs comprise a transgene and a SLIM switch. In some of these embodiments, the transgene acts as the miRNA target sequence for the SLIM switch. In other embodiments, the constructs further comprises the SLIM switch which also contain at least one target miRNA sequence, preferably from about 1-4 target miRNA sequences in the 3' or 5' UTR. For example, FIG. 2B (top figure) shows a suitable design of such construct. Suitable ligands are discussed more below, and specifically include ligands that are able to cross the blood retinal barrier, for example, tetracycline, theophylline and guanine.

In some embodiments, the construct comprises at least one target miRNA sequence, alternatively at least two, alternatively at least three, alternatively at least 4 target miRNA sequences. The number of target miRNA sequences added may depend on the vector used, for example, in the use of a rAAV vector, a suitably number of target miRNA include, for example, from 1-5. Adding more target sites would limit the available coding sequences as there is a limit to the size of the rAAV vectors, thus depending on the size and sequence of the transgene may also alter the number of target miRNA sequences added.

In one embodiment, when the smiRNA is SEQ. ID NO.1, the target miRNA sequence is encoded in SEQ ID NO: 10 (GAGAGAATCTTCTTTCTGTCTATAAAA). In one suitable embodiment, the construct contains at least three target miRNA sequence, for example, as found in SEQ ID NO: 2.

In one embodiment, the construct comprises a suitable transgene in which the expression of the transgene can be induced by administration of the ligand. For example, as described in more detail below, the transgene may be a VEGF inhibitor, specifically a VEGF inhibitor which can be induced to be expressed in the eye for the treatment of AMD. Specifically, a suitable VEGF inhibitor is aflibercept, which is encoded by the cDNA found in SEQ ID NO: 8.

In another embodiment, the aptamer domain and the pri-miRNA are encoded within SEQ ID NO:1. In some embodiments, the construct contains other sequences found within constructs, for example, promoters, enhancers, WPRE elements, and the like. One skilled in the art would be able to incorporate other known elements necessary for transgene expression from a nucleic acid construct.

In some embodiments, the construct is an adeno-associated virus (rAAV), a lentivirus, an adnovirus, a plasmid, a herpes simplex virus, a baculovirus, a bacteriophage, among others. Preferably, the construct is an adeno-associated virus. A suitable rAAV construct is demonstrated in FIG. 2 which incorporates the transgene for aflibercept, a Theo-SLIM switch and 3 miRNA target sequences, for example, the sequence encoded in SEQ ID NO: 9 or SEQ ID NO:19.

In some embodiments, the SLIM switch requires the basal region of a pri-miRNA to be replaced with an aptamer. This sequence is cloned into either the 3'- or 5' untranslated region of an expression cassette. Additionally, miRNA target sites that are complementary to the sequence of the mature miRNA can be included in one or multiple copies at either the 5' or 3' untranslated region of the cassette.

Self-targeting Ligand Inactivated miRNAs (SLIM) switches function by regulating gene expression at the post-transcriptional level. In conditions when the activating ligand is absent, the pri-miRNA will be cleaved by drosha from the nascent transcript. This miRNA will be processed and act as the second mechanism of gene silencing, through binding of the complementary target sites. When the activating ligand is provided, gene expression is unaltered.

Multiple copies of each riboswitch can be included into the 3'-untranslated region of the gene of interest. Each riboswitch appears to have an optimal number of copies as shown in Table 1. Furthermore, in some embodiments, multiple copies of miRNA target sites can be included in the 3' or 5' untranslated region. The synthetic riboswitches comprise an aptamer and an expression platform and rely on changes in the expression platform activity for regulating gene expression. The miRNA target sites are sequences in the therapeutic cassette (construct) that are recognized by the mature miRNA/siRNA. As discussed more below, the miRNA target sites may be encompassed within the transgene. In other words, the cleaved and processed siRNA from the riboswitch binds to the transgene and inhibits its expression.

Alternatively, the SLIM switch can be generated towards the transgene itself, with Eylea and sFlt1 for the treatment of AMD, the sequences are found in FIGS. 16-18, 19 and 23.

In one embodiment, the nucleic acid construct comprises a target gene of interest, for example, a VEGF inhibitor (e.g. Eylea (SEQ ID NO:20) or sFLT1 (SEQ ID NO:36) and at least one miRNA SLIM switch located within the untranslated region of the target gene (e.g. at least one selected from SEQ ID NO:21-35 or SEQ ID NO:37-51, respectively of the VEGF inhibitors).

In some embodiments, the nucleic acid construct is an rAAV vector comprising the Eylea gene (e.g. SEQ ID NO: 19). For example, SEQ ID NO: 19 provides a complete AAV expression vector for the expression of Eylea using a SLIM switch. Within SEQ ID NO: 19, X marks positions in which a SLIM sequence may be inserted. Suitable SLIM sequences that may be inserted can be found in FIG. 18, and include, but are not limited to, 6S-Folinic Acid-responsive SLIM (miRNA) switches, including, for example, SEQ ID NO: 21, 22, 23, 24, and 25 (activated by the ligand 6S-Folinic acid), Theophylline-responsive SLIM, for example, SEQ ID NO: 26, 27, 28, 29 and 30 (activated by ligand theophylline), or Tetracycline-responsive SLIM, for example, SEQ ID NO:31, 32, 33, 34, and 35 (activated by ligand tetracycline). In some embodiments, from 1-5 SLIM sequences are inserted within the AAV expression vector, alternatively from 1-3 SLIM sequences. For example, SEQ ID NO:19 may incorporate 1-5 copies of SEQ ID NO:21, alternatively 1-5 copies of SEQ ID NO:22, alternatively 1-5 copies of SEQ ID NO: 23, alternatively 1-5 copies of SEQ ID NO:24, alternatively 1-5 copies of SEQ ID NO: 25, alternatively 1-5 copies of SEQ ID NO:26, alternatively 1-5 copies of SEQ ID NO: 27, alternatively 1-5 copies of SEQ ID NO:28, alternatively 1-5 copies of SEQ ID NO:29, alternatively 1-5 copies of SEQ ID NO:30, alternatively 1-5 copies of SEQ ID NO:31, alternatively 1-5 copies of SEQ ID NO:32, alternatively 1-5 copies of SEQ ID NO:33, alternatively 1-5 copies of SEQ ID NO:34, alternatively 1-5 copies of SEQ ID NO:35.

In another embodiment, the nucleic acid construct comprises a target gene of interest, for example, a VEGF inhibitor sFLT1 (SEQ ID NO:36) and at least one smiRNA SLIM switch located within the untranslated region of the target gene (e.g. at least one selected from SEQ ID NO:37-51).

In some embodiments, the nucleic acid construct comprises the sFLT1 gene (SEQ ID NO:36). sFLT1 may be inserted within a vector, for example a rAAV vector, and flanked by X which marks positions in which a SLIM sequence may be inserted. Suitable SLIM sequences that may be inserted can be found in FIG. 18, and include, but are not limited to, 6S-Folinic Acid-responsive SLIM (miRNA) switches, including, for example, SEQ ID NO: 37, 38, 39, 40, 41 (activated by the ligand 6S-Folinic acid), Theophylline-responsive SLIM, for example, SEQ ID NO:42, 43, 44, 45, 46 (activated by ligand theophylline), or Tetracycline-responsive SLIM, for example, SEQ ID NO:47, 48, 49, 50, and 51 (activated by ligand tetracycline). In some embodiments, from 1-5 SLIM sequences are inserted within the construct, alternatively from 1-3 SLIM sequences. For example, SEQ ID NO:36 may incorporate as X from 1-5 copies of SEQ ID NO:37, alternatively from 1-5 copies of SEQ ID NO: 38, alternatively from 1-5 copies of SEQ ID NO:39, alternatively from 1-5 copies of SEQ ID NO: 40, alternatively from 1-5 copies of SEQ ID NO:41, alternatively from 1-5 copies of SEQ ID NO:42, alternatively from 1-5 copies of SEQ ID NO:43, alternatively from 1-5 copies of SEQ ID NO:44, alternatively from 1-5 copies of SEQ ID NO:45, alternatively from 1-5 copies of SEQ ID NO:46, alternatively from 1-5 copies of SEQ ID NO:47, alternatively from 1-5 copies of SEQ ID NO:48, alternatively from 1-5 copies of SEQ ID NO:49, alternatively from 1-5 copies of SEQ ID NO:50, or alternatively from 1-5 copies of SEQ ID NO:51. Alternative combinations of SLIM sequences are contemplated (e.g. for example from 1-5 SLIM sequences selected from SEQ ID NO:36, 37, 38, 39, 40, and 41). Suitable, one would preferably use SLIM sequences activated by the same ligand in the construct, for example 1-5 SLIM sequences that are active by the tetracycline ligand.

Figure 21:
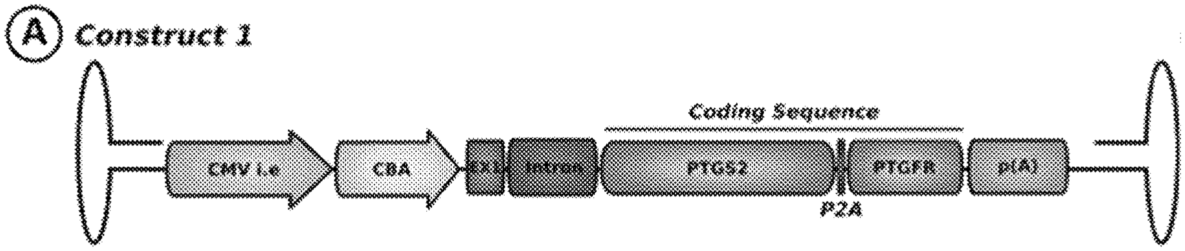
FIG. 21 is a depiction of a vector construct of a vector (e.g. AAV vector) comprising prostaglandin endoperoxide synthase 2 (PTGS2) and PTGFR.
Figure 22:
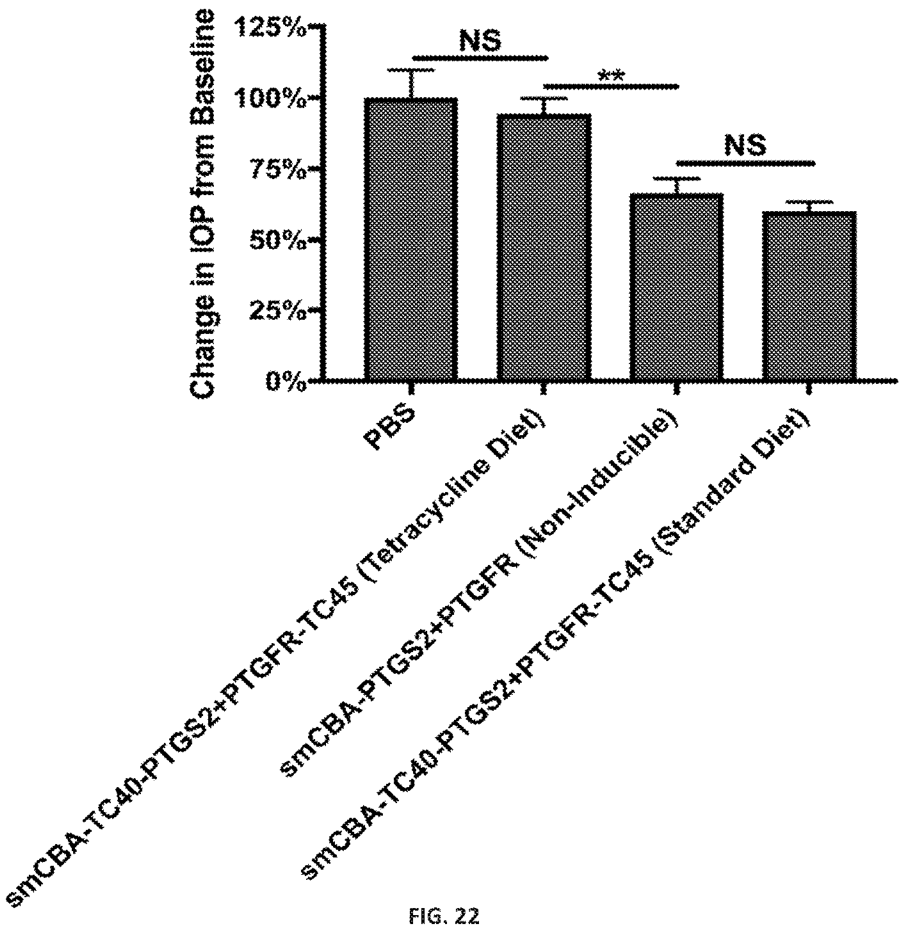
FIG. 22 is a graph depicting the change in intraocular pressure (IOP) from baseline in mice after treatment with an AAV with SLIM riboswitch and administration of the ligand tetracycline.

In another embodiment depicted in FIG. 21, a nucleic acid construct comprises PTGS2 (SEQ ID NO:52) and PTGFR (SEQ ID NO:53) (depicted in combination in SEQ ID NO: 54 as PTGS2-P2A-PTGFR). Suitable nucleic acid construct is depicted in FIG. 23 as SEQ ID NO: 58, a AAV expression vector comprising PGF2alpha biosynthesis regulatory genes (PTGS2 (SEQ ID NO:60) and PTGFR (SEQ ID NO:62) including two synthetic riboswitches TC40 (SEQ ID NO:59) and TC45 (SEQ ID NO:63). Suitable use of such construct is for the treatment of glaucoma.

Ligands

The specific ligand to be used depends on the specific application and aptamer incorporated into the SLIM switches. For the treatment of eye diseases and disorders, ligands that are able to cross the blood retinal barrier are preferred. Suitable aptamers that can cross the blood retinal barrier include, but are not limited to, for example, tetracycline, theophylline, guanine, galactitol, progesterone, mannitol, estradiol, dopamine, quinidine, urea, digoxin, uracil, verapamil, thiourea, moxifloxacin, thymine, levofloxin, corticosterone, acetazolamide, testosterone, doxycycline, and combinations thereof.

In a preferred embodiment, the ligand is selected from the group consisting of tetracycline, theophylline and guanine.

Suitable routes of administration of the ligands are known in the art and include, oral administering, administering via the eye (e.g., eyedrops) and the like.

Treatment of Eye Diseases

The constructs of the present technology are particularly useful for gene therapy for the treatment of eye diseases. The eye is a particularly good target for this type of gene therapy for a number of reasons. The eye is a highly specialized organ which has evolved to transduce light stimuli into electrical signals and to relay those signals to the visual cortex. Light sensation and image formation is mediated through the activation of photoreceptor cells located in the outermost layer of the neurosensory retina, where incident light focused by the cornea and lens results in the activation of a signaling cascade and the propagation of an electrical impulse. Despite its complexity the eye has many traits which make it an attractive organ for gene therapy: it is relatively immune privileged, has a small compartment size, is easily visualized and examined, and readily accessible with minimal risk to patients undergoing surgery. The retina (AMD) or the cornea (Glaucoma) are the primary targets for gene therapy treatments. Vector delivery is usually achieved through injection of a fluid suspension containing the therapeutic particles into the anatomically constrained space adjacent to the target cells. A rAAV.SLIM.αVEGF or rAAV.SLIM.sFLT1 vector would be most beneficial if targeted towards cells of the inner retina, including retinal ganglion cells and Müller glia, and as such would be administered via intravitreal injection. The rAAV.SLIM.PTGS2-P2-PTGFR vector would be most beneficial if targeted towards cells of the cornea and anterior chamber, including corneal endothelial cells, and as such would be administered via intracameral injection. Numerous rAAV clinical trials using rAAV for ocular gene therapy applications have been successfully completed; however, all trials to date have utilized a sub-retinal delivery approach designed to target photoreceptors. A current phase I/II clinical trial (NCT01494805) is underway utilizing rAAV-mediated overexpression of soluble fms-like tyrosine kinase-1 (sFLT), a soluble receptor of VEGF, for the treatment of AMD. Expression of sFLT in this trial is constitutive, and cannot be regulated, unlike the proposed rAAV.SLIM.αVEGF and rAAV.SLIM.sFLT1 technology described herein. No rAAV-based gene therapy clinical trials are underway for the treatment of glaucoma.

Treatment of AMD

The present invention provides methods of treating age-related macular degeneration by inhibiting, reducing or alleviating at least one symptom of AMD. AMD is a disease involving multiple tissue layers within the eye, including the choroid, retinal pigment epithelium and the neurosensory retina, and occurs in two forms. Dry AMD is a non-proliferative disease state characterized by progressive geographic atrophy of the central retina. In approximately 10-15% of patients the disease progresses to a wet form, characterized by abnormal growth of blood vessels from the choroid into the subretinal space. Choroidal neovascularization (CNV) results primarily as a result of increased intraocular concentrations of VEGF and is the major vision-threatening symptom of AMD. Administration of anti-VEGF agents is known to significantly reduce the incidence of CNV and is the current gold-standard treatment AMD. The treatment regimen is invasive, however, requiring repetitive (e.g. monthly or bimonthly) intravitreal injection of purified recombinant anti-VEGF protein.

The proposed rAAV.SLIM.αVEGF technology would act to significantly reduce the incidence of CNV formation in AMD patients, and consequently prevent vision loss. Critically, the inclusion of the SLIM technology would allow for anti-VEGF expression to be controlled through dosing of the activating ligand.

The rAAV.SLIM.αVEGF vector technology of the present invention would act to significantly reduce the incidence of CNV formation in AMD patients, and consequently prevent vision loss. Critically, the inclusion of the SLIM technology would allow for anti-VEGF expression to be controlled through dosing of the activating ligand.

The present invention provides methods of treating, reducing, alleviating or inhibiting at least one symptom of AMD comprising administering to the eye of a subject a construct comprising a VEGF inhibitor and a SLIM riboswitch as described herein (including, e.g., rAAV.SLIM.αVEGF or rAAV.SLIM.sFLT1 vector), and further administering a therapeutically effective amount of the ligand. The SLIM riboswitch can determine which ligand is used as described in more detail herein. Suitably, the treatment results in the reduction, alleviation or inhibition of one or more symptom of AMD, for example, a reduction or inhibition of the development of CNV.

In one embodiment, the method of treating, inhibiting or reducing at least one symptom of AMD comprises administering a construct comprising one or more ON-type riboswitch operably connected to a transgene encoding a VEGF inhibitor and administering a therapeutically effective amount of the ligand. Suitable ON-type riboswitches are known in the art and include, but are not limited to, for example, L2Bulge18tc (SEQ ID NO:12), K19 (SEQ ID NO:15), and L2Bulge 9 (SEQ ID NO:11). Further, the construct may encode an optimal copy number of the ON-type riboswitches which can be incorporated into the construct. The optimal copy number of the riboswitch is detailed in Table. 1. For example a construct for the treatment of AMD may comprise from 1-3 L2Bulge18tc riboswitches and a VEGF inhibitor.

TABLE 1

ON-TYPE Switches and SLIM switches

| Riboswitches | Activating Ligand | Optimal Copy number | | Dynamic Range | SEQ ID NO: |
|---|---|---|---|---|---|
| L2Bulge18tc | Tetracycline | 3 | 12.5 | 4.3-fold | 12 |
| K19 | Tetracycline | 1 | 39.1 | 1.5-fold | 15 |
| L2Bulge9 | Theophylline | 3 | 37.9 | 1.7-fold | 11 |
| Theo-SLIM | Theophylline | 1 | 7.2 | 10.9-fold | 1 |
| Tet-SLIM | Tetracycline | 1 | 36.4 | 2.3-fold | 17 |

The SLIM riboswitches can be incorporated into constructs of the present invention to alter gene expression of the transgene by administration of a therapeutically effective amount of the ligand. By “therapeutically effective amount” we mean an amount or dosage of the ligand that is able to alter the expression level of the transgene product in a cell. One skilled in the art will be able to titrate and determine a therapeutically effective amount to produce the proper response and result in a reduction of the symptoms of the desired disease to be treated. A therapeutically effective amount also maintains that the level of ligand is in a non-toxic dose to the subject. Suitably, the dosage may be given daily, weekly or monthly depending on the particular requirements for expression in the subject.

Treatment of Glaucoma

The present invention provides for the first time higher functioning genetic switches in a retinal model which can be used to regulate transgenes within the eye to treat eye diseases. The SLIM switches described above have the potential to have an increased dynamic range over traditional riboswitches and can be used for the treatment, inhibition or amelioration of one or more symptom of glaucoma, including high intraocular pressure. Prostaglandin synthesis will be regulated by orally ingesting the activating ligand. The dose of the activating ligand will be determined by intraocular pressure (IOP) readings of the patient through the use of a rebound tonometer.

The present disclosure provides methods of treating glaucoma comprising gene therapy using an adeno-associated virus encoding the construct comprising a SLIM switch and one or more genes that regulate prostaglandin synthesis as described herein. In another embodiment, the disclosure provides a method of treating glaucoma comprising administering an adeno-associated virus encoding a construct comprising one or more genes that regulate prostaglandin synthesis and at least one ON-type riboswitch (SLIM). FIGS. 21 and 23 provide one such example of the AAV vector encoding genes necessary for regulation of prostaglandin synthesis and suitable SLIM riboswitches for use in the present invention.

Glaucoma is typified by elevated intra-ocular pressure (IOP) leading to progressive loss of retinal ganglion cells and, ultimately severe visual impairment. Increased IOP results from an imbalance between the production of aqueous humour by the ciliary body in the eye's posterior chamber and its drainage through the trabecular meshwork in the anterior chamber. Glaucoma can be categorized based on whether the drainage through the trabecular meshwork is completely (closed angle) or partially (open angle) blocked. Open angel glaucoma is most common and usually presents with no symptoms other than slow progressive vision loss. Closed angle glaucoma is loss common and is considered to be a medical emergency, presenting with acute eye pain, headaches, blurred vision, excessive lacrimation nausea and vomiting.

Due to its chronic nature, the proposed rAAV.SLIM.PTGS2-P2-PTGFR (SEQ ID NO: 58) technology would be appropriate for the treatment of glaucoma.

In one embodiment, a method of reducing, inhibiting or ameliorating at least one symptom of glaucoma is provided. The method comprises administering an exogenous nucleic acid construct to the eye of the subject. In one embodiment, the exogenous nucleic acid construct encodes a transgene that regulates prostaglandin 2α synthesis and at least one smiRNA riboswitch. In another embodiment, the exogenous nucleic acid construct encodes: (i) a transgene that regulates prostaglandin synthesis (e.g., prostaglandin endoperoxide synthase 2 (PTGS2); (ii) a smiRNA switch located within the untranslated region of the transgene, wherein the smiRNA switch comprises at least two riboswitches flanking a pri-miRNA, each riboswitch comprising an aptamer operably linked to an expression platform, and (iii) at least one miRNA target sequence complementary to at least a portion of the pri-miRNA, wherein the transgene is incorporated into cells of the subject and express the transgene, and (b) administering a therapeutically effective amount of the ligand that is able to bind to the aptamer in order to regulate expression of the transgene within the eye to reduce, inhibit or ameliorate at least one symptom of glaucoma. In one embodiment, the symptom is high intraocular pressure.

Suitable ligands include ligands that can cross the blood retinal barrier, as described herein.

Suitably, the transgene that regulates prostaglandin 2α synthesis includes, but is not limited to, for example, PTGS2 (SEQ ID NO:52) among others. Other suitable transgenes are known in the art.

Kits

This disclosure provides kits. The kits can be suitable for use in the methods described herein. In one aspects, a kit can include a rAAV vector comprising the constructs as described herein, for example, a SLIM switch containing construct. In some aspects, the kit can include a construct comprising rAAV vector encoding a VEGF inhibitor as described herein. In other aspects, the kit can include a construct comprising a rAAV vector encoding one or more genes involved in the regulation of prostaglandin synthesis as described herein. Further, the kits may comprise one or more doses of the ligand to be administered after initial administration of the rAAV vector. Instructions on the timing of the dosages and proper administration methods may be provided.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The term "treating" or "treatment" includes, but is not limited to, reducing, inhibiting or preventing one or more signs or symptoms associated with the disease or disorder. For example, treating glaucoma include, for example, reduction in the intraocular eye pressure (e.g. the symptom of glaucoma being treated is high intraocular pressure).

The terms "effective amount" or "therapeutically effective amount" refer to an amount sufficient to effect beneficial or desirable biological and/or clinical results.

"Expression platform" Within the context of the disclosure, the portion of the modified riboswitch which mediates the effect on the nucleic acid expression is known as the expression platform. Preferably, the expression platform is operably linked to the aptamer domain of the riboswitch, preferably structurally linked, most preferably by a nucleic acid linker. Most preferred is that the aptamer domain is linked to the expression platform by a nucleic acid sequence. Preferably, the stem configuration of the portion of the expression platform changes configuration upon binding of a ligand, such that a change in the configuration of the stem structure results in a corresponding change in the structure of the expression platform, between a first configuration which enhances expression of the nucleic acid sequence and a second configuration which inhibits expression of the nucleic acid sequence.

"Genetic construct" can include nucleic acid sequences that permit it to replicate in the host cell. Examples include, but are not limited to a plasmid, cosmid, bacteriophage, or virus that carries exogenous DNA into a cell. A genetic construct can also include additional selectable marker genes and other genetic elements known in the art. A genetic construct can preferably transduce, transform or infect a cell, thereby causing the cell to express the nucleic acids and/or proteins encoded by the vector.

"Operably linked" a first element is operably linked with a second element when the first element is placed in a functional relationship with functional relationship with the second element. For instance, a aptamer is operably linked to an expression platform when the binding of the aptamer to its ligand causes conformational changes to the expression platform which alters the function of the expression platform (for example, if the expression platform is a ribozyme, binding of the aptamer to the ligand can activate the ribozyme activity). Generally, operably linked DNA sequences are contiguous and, where necessary to join two protein coding regions, in the same reading frame.

It is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

Aspects of the present disclosure that are described with respect to methods can be utilized in the context of the compositions of matter or kits discussed in this disclosure. Similarly, aspects of the present disclosure that are described with respect to compositions of matter can be utilized in the context of the methods and kits, and aspects of the present disclosure that are described with respect to kits can be utilized in the context of the methods and compositions of matter.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1: Ability to Regulate Gene Expression In Vivo in the Eye

This Example demonstrates that six riboswitches respond to a ligand in cell culture and in vivo when deliver to the mouse retina.

Six small (~100 bp) riboswitches (K19, Tc40x45, GuaM8HDV, L2Bulge18tc, L2Bulge9 and Theo6HDV) responded to a ligand in cell culture, and in vivo when delivered to the mouse retina using a rAAV2 vector.

The riboswitches were evaluated in HEK293T cells to determine optimal copy number (largest dynamic range) and dose-responsiveness to its activating ligand using a dual luciferase assay. The ligand used were tetracycline and theophylline.

Cell culture experiments revealed significant changes in firefly luminescence in response to dosing of the appropriate ligand ($p<0.01$, One-way ANOVA, N=4 all groups).

Next, the optimal copy number of each riboswitch was cloned into arAAV GFP reporter cassette and packaged in an AAV2 capsid. Each GFP-riboswitch cassette was injected intravitreally into C57Bl/6j mice in combination with an AAV2 control vector harboring a non-inducible mCherry reporter gene. Four weeks post-injection, mCherry and GFP fluorescence levels were quantified in vivo using a custom 'Multiline' confocal scanning laser ophthalmoscope (cSLO). Mice subsequently received a dose of 1000 mg/kg of its activating ligand (tetracycline, theophylline), and fluorescence levels were quantified 2 and 24 hours post-gavage.

Figure 6B:
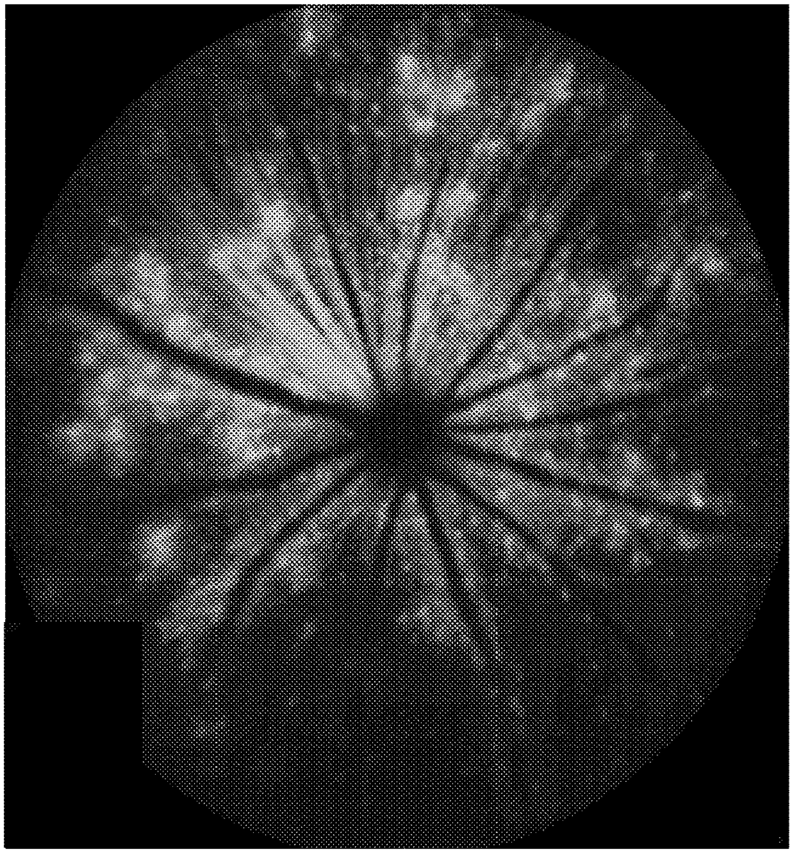
FIG. 6B is fluorescent imaging of GFP two hours post-gavage @ 10 mg/kg of theophylline (activating ligand).
Figure 6A:
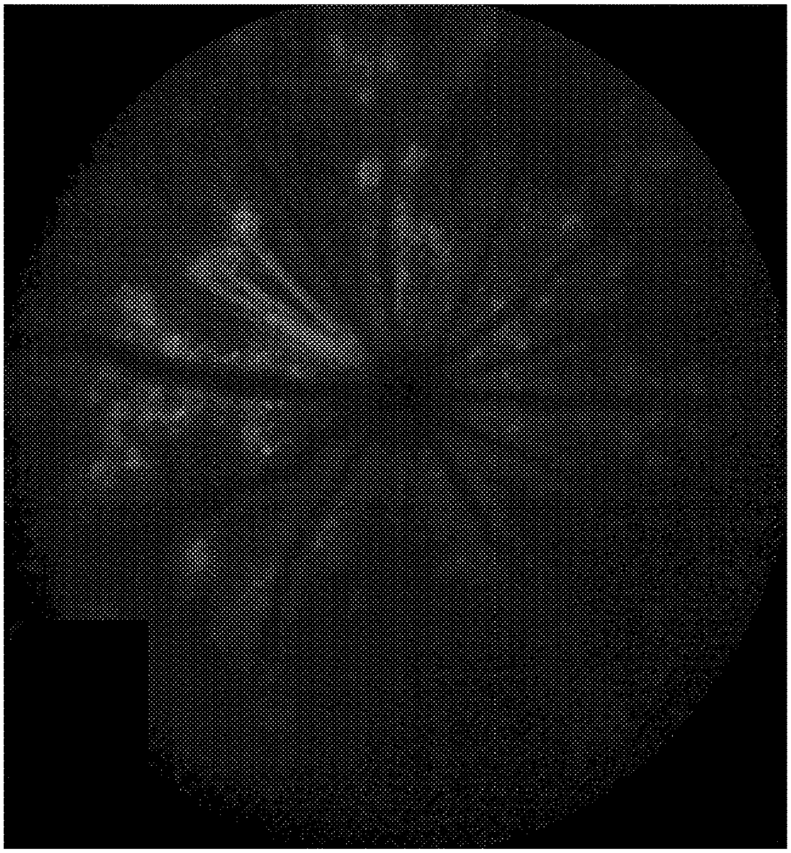
FIG. 6A is fluorescent imaging depicting GFP expression in the retina of a mouse 4 weeks post infection. C57BL6/J mouse injected intravitreally with $1.0\times10^{10}$ vector genomes (vg) of rAAV2.smCBA-hGFP-3x-L2Bulge9.
Figure 7:
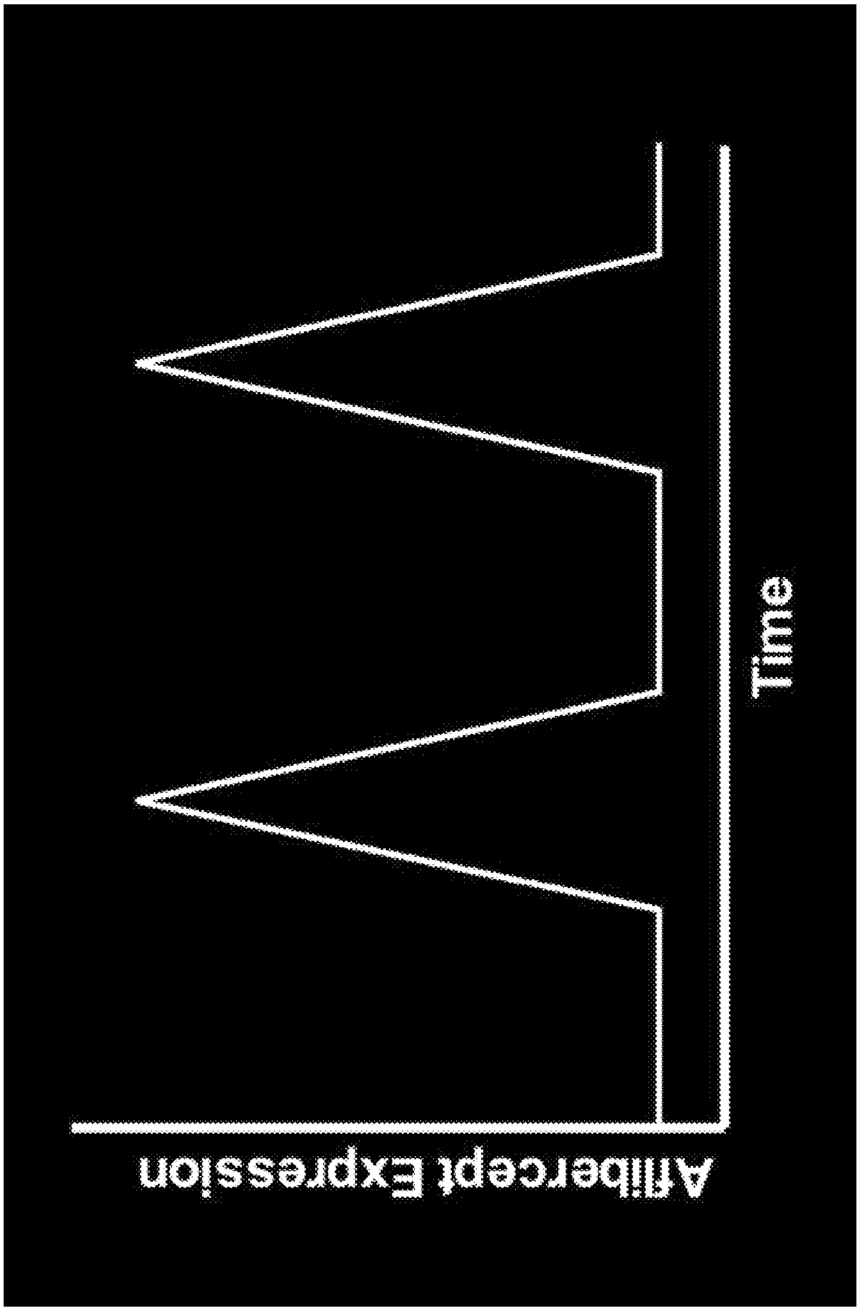
FIG. 7 is proposed response of using a SLIM switch (constitutively off transgene), showing monthly administration of ligand results in a spike in expression level of the transgene (e.g. aflibercept).

In vivo results demonstrated dosing mice with the activating ligand of each riboswitch could achieve a highly significant change in GFP fluorescence at 2 hours post-gavage compared to pre-treatment levels ($p<0.01$, paired t test, N=6) (FIGS. 6A and 6B). Importantly, GFP fluorescence was recovered to pre-treatment levels 24 hours after receiving the activating ligand. This shows that genes can be delivered and expressed in the retina of the eye.

Example 2: Evaluation of Optimal Copy Number of Riboswitches and Dynamic Range

Example 2A: Testing of Known Riboswitches

Figure 8A:
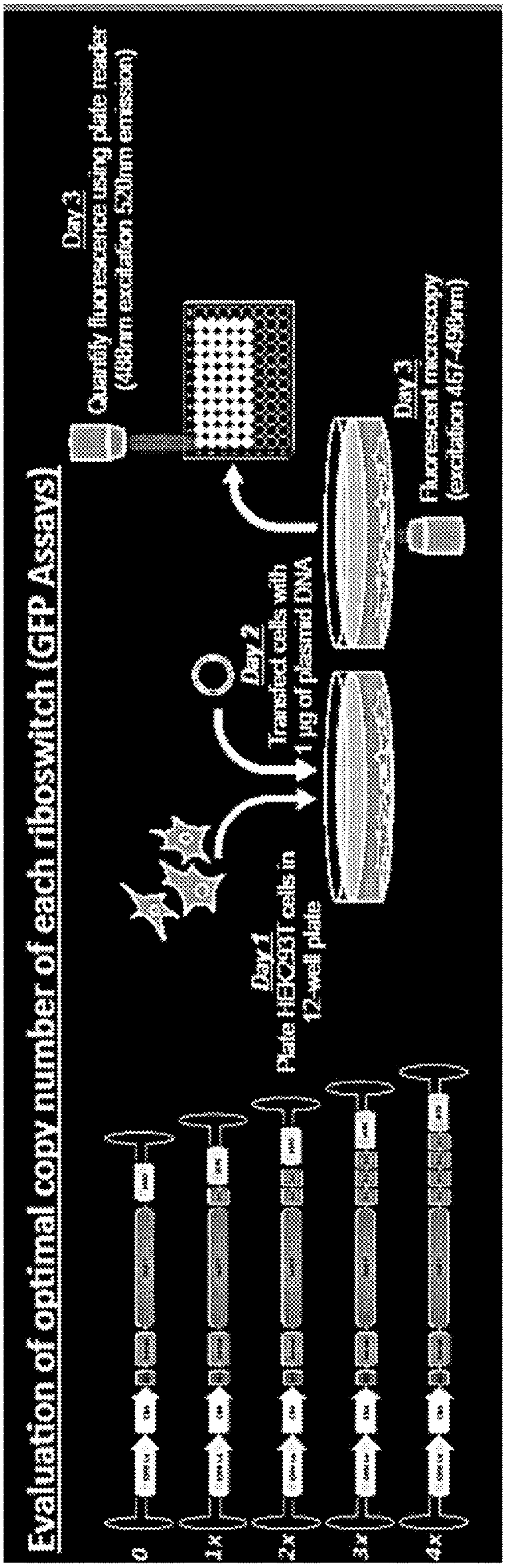
FIG. 8A is a schematic of the testing protocol for determining the optimal copy number of each riboswitch.
Figure 8B:
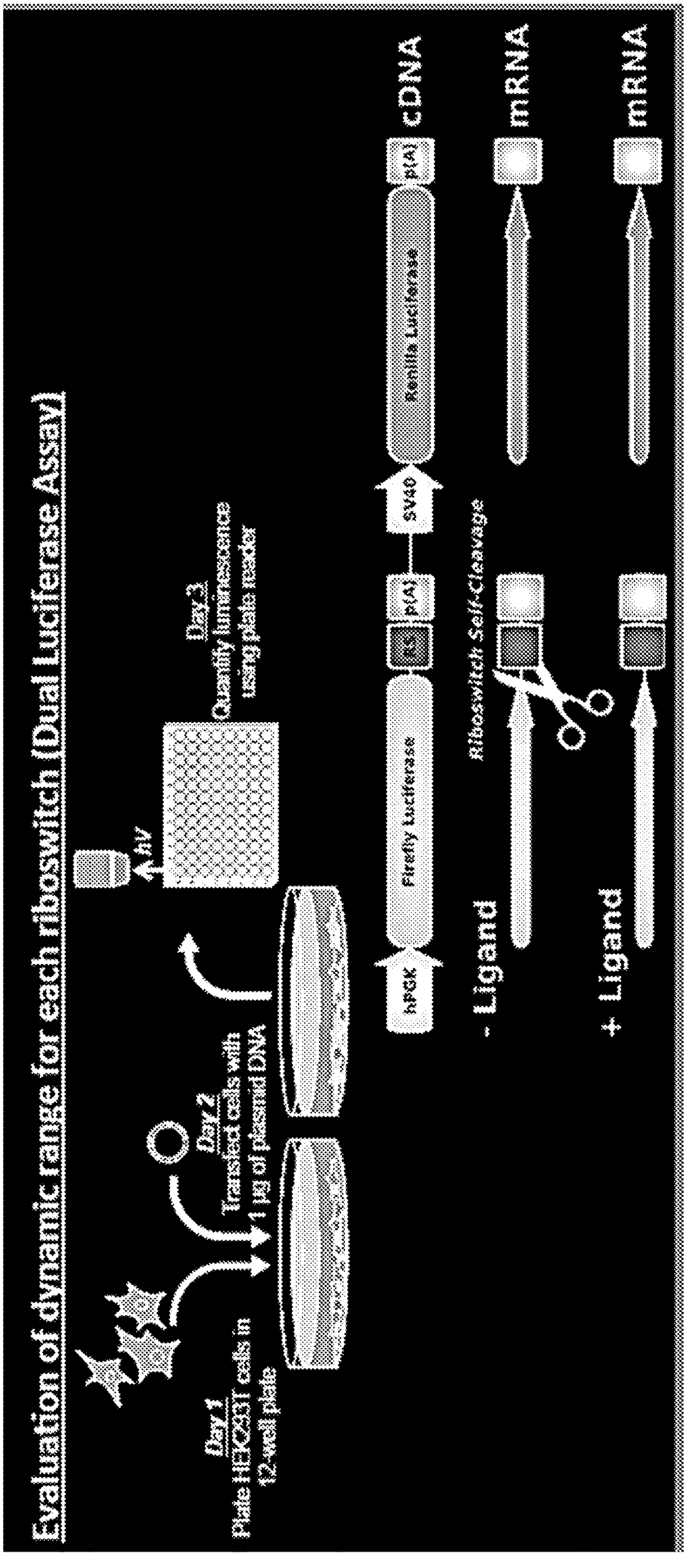
FIG. 8B is a schematic of the testing protocol for evaluation of dynamic range for each riboswitch.

This Example demonstrates the optimal number of riboswitches that can be used in a construct and the related dynamic ranges. The protocol for both assays are outlined in FIGS. 8A and 8B. For determining optimal copy numbers, plasmids containing 0-4 copies of each riboswitch were created with the transgene as green fluorescence protein (GFP) for readout. HEK293T cells were plated in a 12-well plate and on day 2 transfected with 1 μg of each plasmid DNA. On day 3, cells were observed by fluorescent microscopy (excitation 467-498 nm) and fluorescence was quantified using a plate reader (488 nm excitation 520 nm emission).

For determining dynamic range, constructs containing firefly luciferase containing the optimal copy number of the riboswitch were made. HEK293T cells were plated on day 1, and transfected on day 2 with 1 μg of plasmid DNA. Cells were treated with 0-100 μM of the ligand corresponding to the riboswitch and the luminescence was quantified on day 3 using plate reader. Results are shown in Table 2.

Figure 9A:
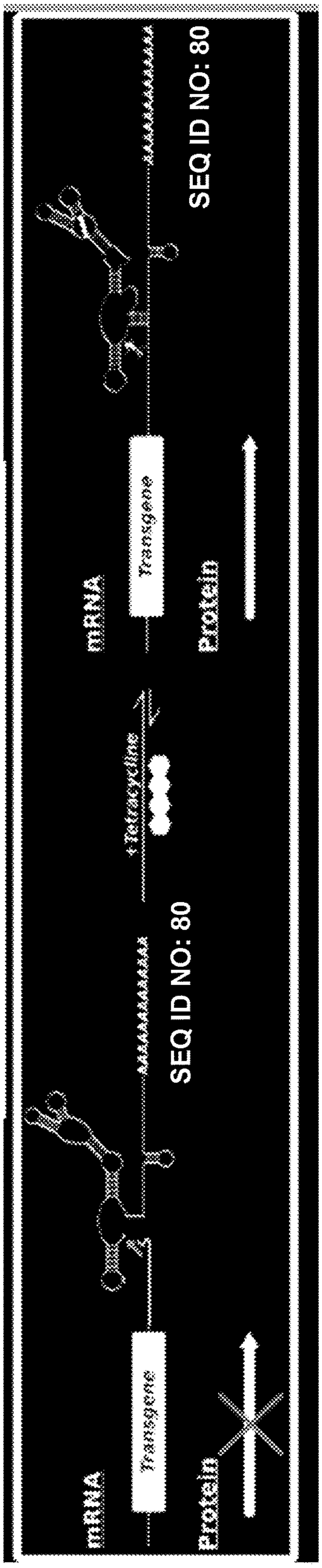
FIG. 9A is a schematic representation of the mRNA of a L2Bulge18tc riboswitch construct.
Figure 9B:
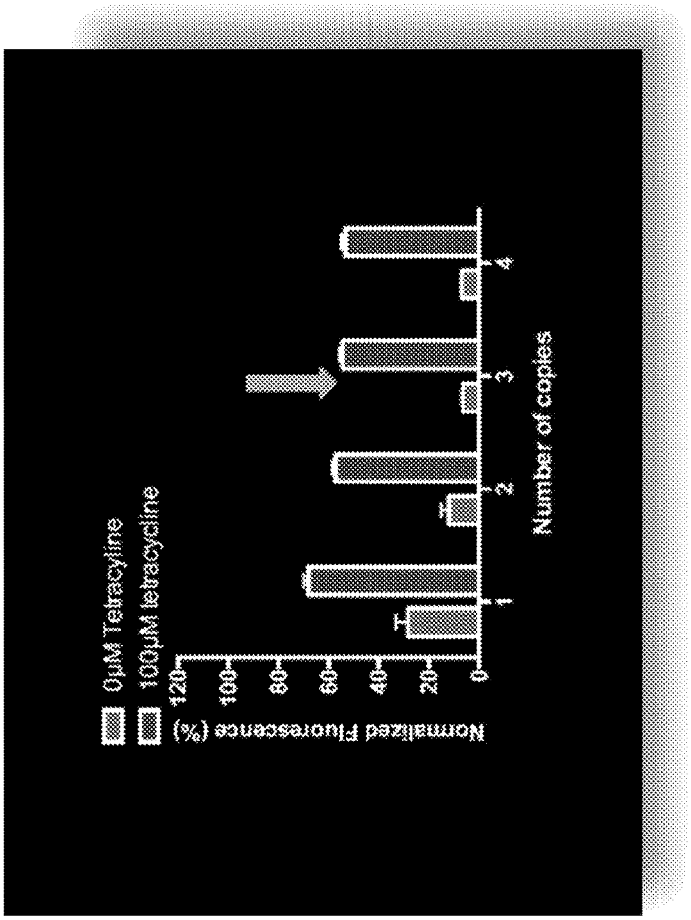
FIG. 9B is a bar graph depicting the results of different copy numbers of the L2Bulge18tc riboswitch on expression levels of a transgene (GFP).
Figure 9C:
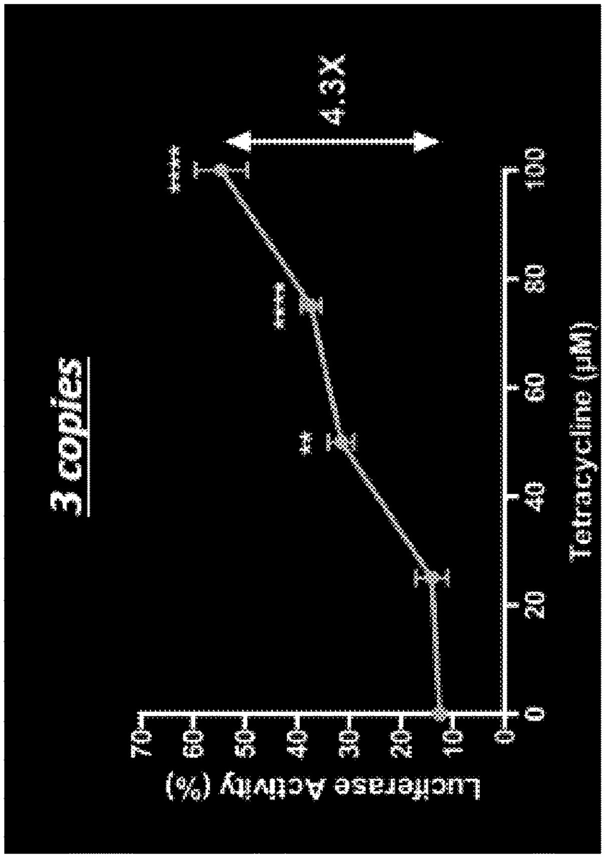
FIG. 9C is a line graph depicting the dynamic range of a construct comprising 3 copies of the L2Bulge18tc riboswitch.
Figure 9D:
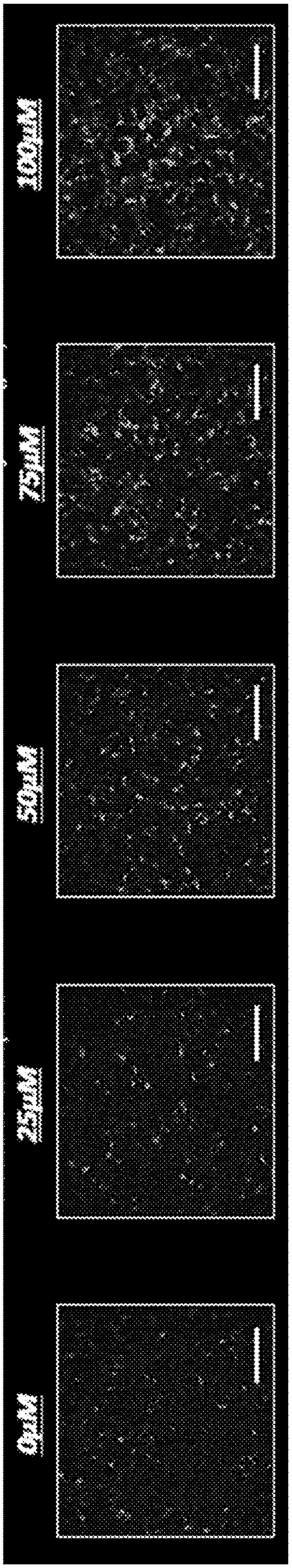
FIG. 9D are fluorescent imaging of cells treated with 0-100 μM tetracycline.
Figure 10A:
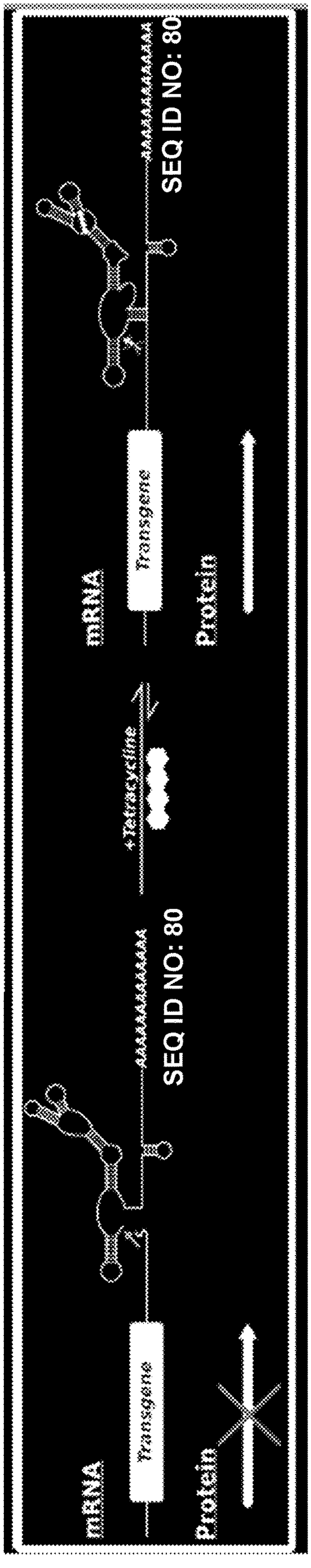
FIG. 10A a schematic representation of the mRNA of a construct containing a K19 riboswitch.
Figure 10B:
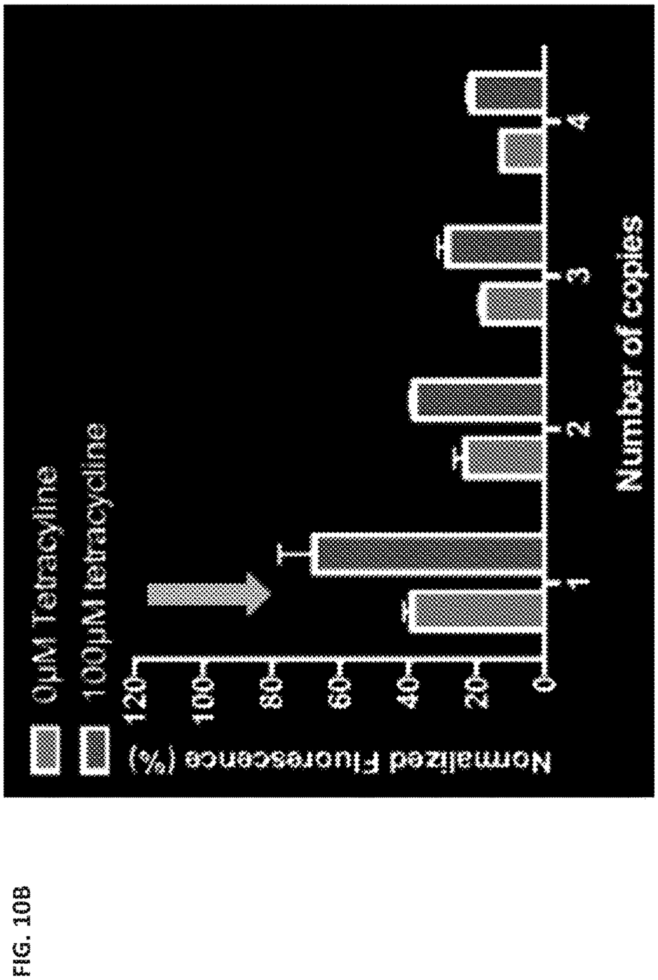
FIG. 10B is a bar graph depicting the results of different copy numbers of the K19 riboswitch on transgene expression levels.
Figure 10C:
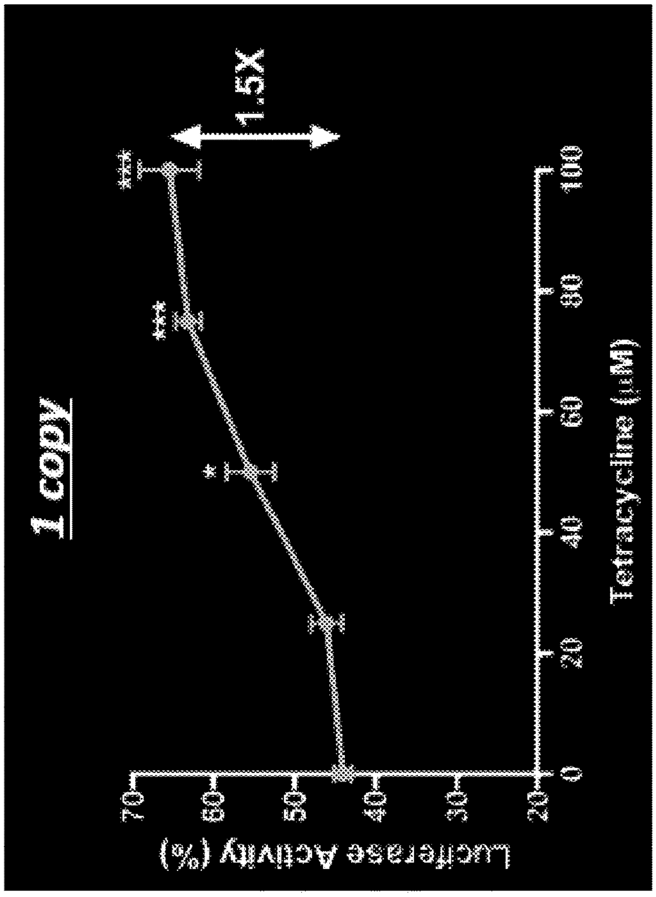
FIG. 10C is a line graph depicting the dynamic range of the optimal copy number of K19 riboswitch.
Figure 10D:
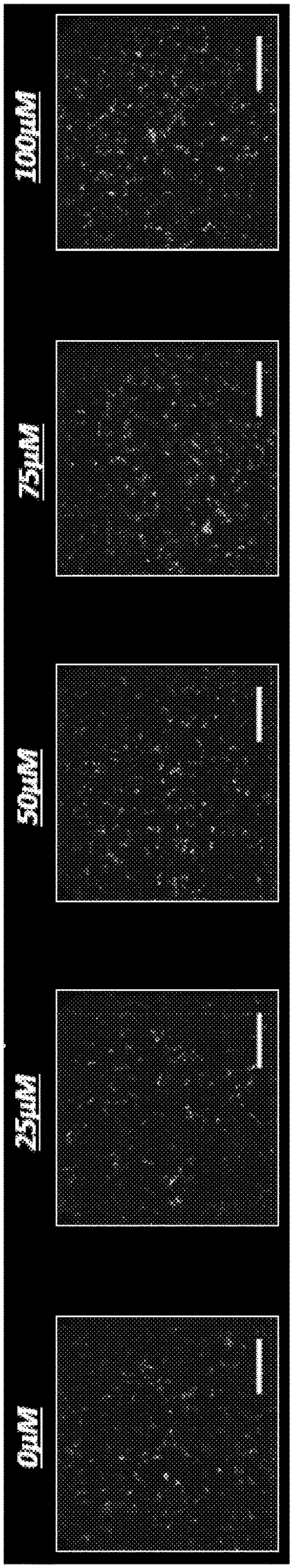
FIG. 10D are fluorescent imaging of cells treated with 0-100 μM of tetracycline which were transduced with the K19 riboswitch construct of 10A.
Figure 11A:
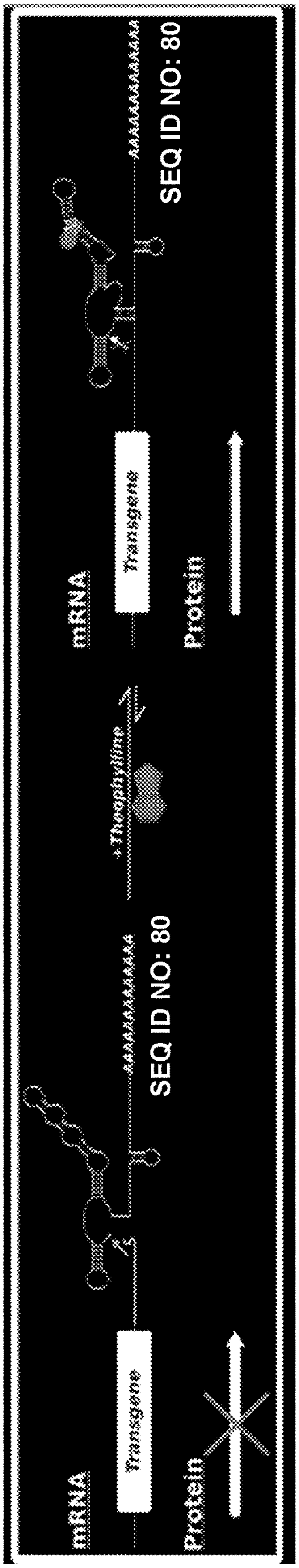
FIG. 11A depicts the mRNA of a construct comprising the L2Bulge9 riboswitch.
Figure 11B:
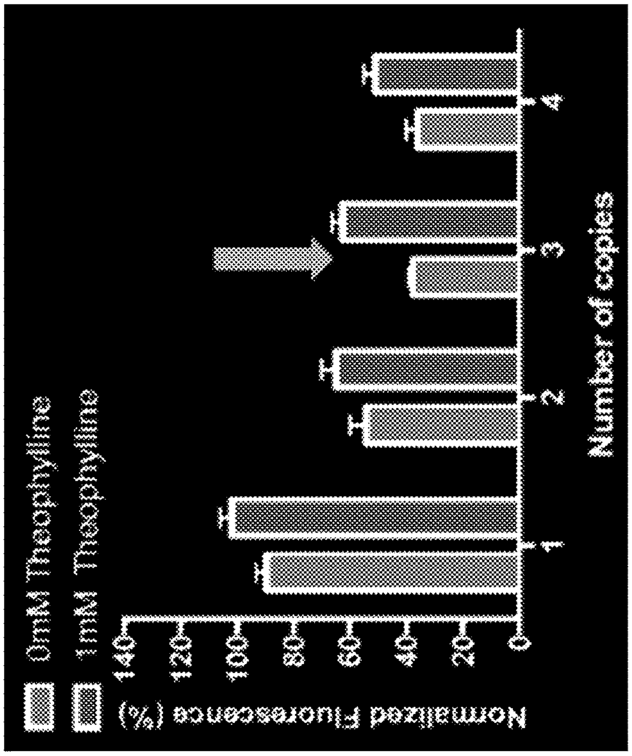
FIG. 11B is a bar graph depicting the results of different copy numbers of the L2Bulge9 riboswitch on transgene expression levels.
Figure 11C:
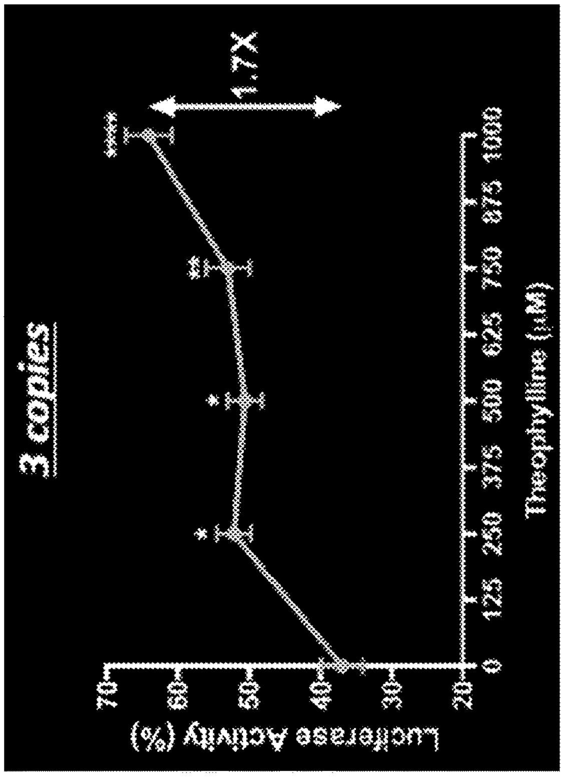
FIG. 11C is a line graph depicting the dynamic range of the optimal copy number of L2Bulge9 riboswitch.
Figure 11D:
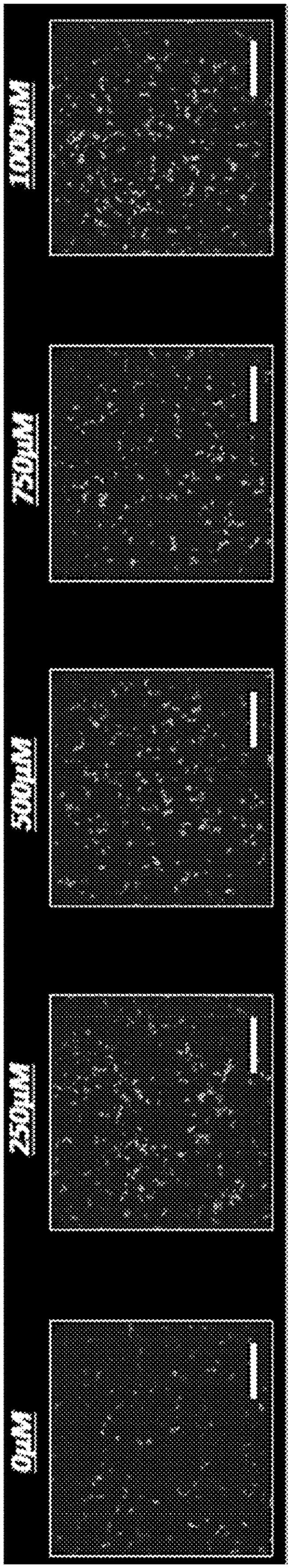
FIG. 11D are fluorescent imaging of cells treated with 0-100 μM of theophylline which were transduced with the L2Bulge9 riboswitch construct of 11A.

As depicted in FIG. 9A, L2Bulge18tc riboswitch was one ON-type riboswitch tested. The cells were treated with 0 μM, 25 μM, 50 μM, 75 μM, and 100 μM of tetracycline (ligand), with the fluorescent microscopy results shown in FIG. 9D. Fluorescence was quantified and results are demonstrated in FIG. 9B, demonstrating 3 copies provides optimal dynamic range, as depicted in FIG. 9C.

K19 riboswitch was also tested (FIG. 10) as described above, and the results are shown in FIG. 9B-D, demonstrating that 1 copy is the optimal copy number.

L2Bulge 9 was also tested (using activating ligand Theophylline), and the optimal copy number was determined to be 3.

Results for a number of ON-type riboswitches are summarized in Table 1 above.

Example 2B: Testing of New SLIM Switches

Figure 12A:
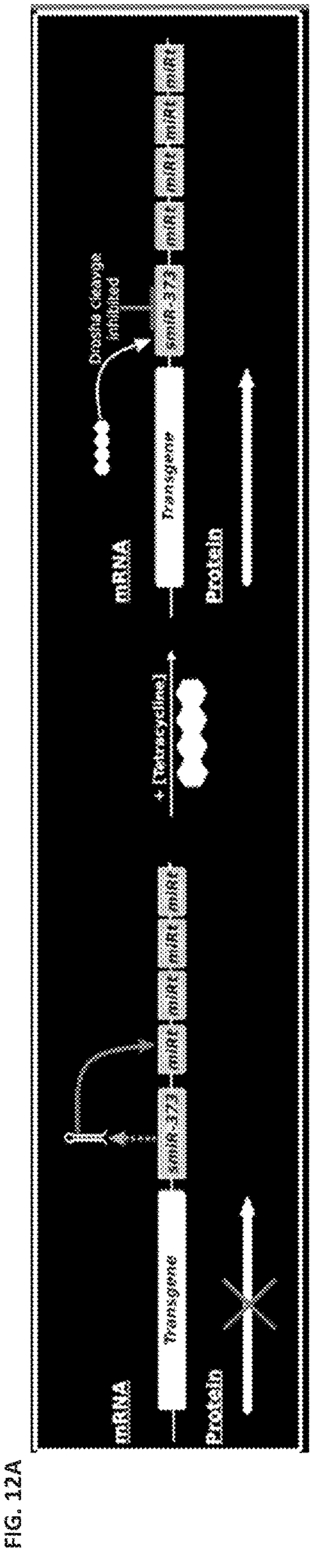
FIG. 12A depicts the mRNA of a construct comprising the tetracycline SLIM switch (ON-type switch).
Figure 12B:
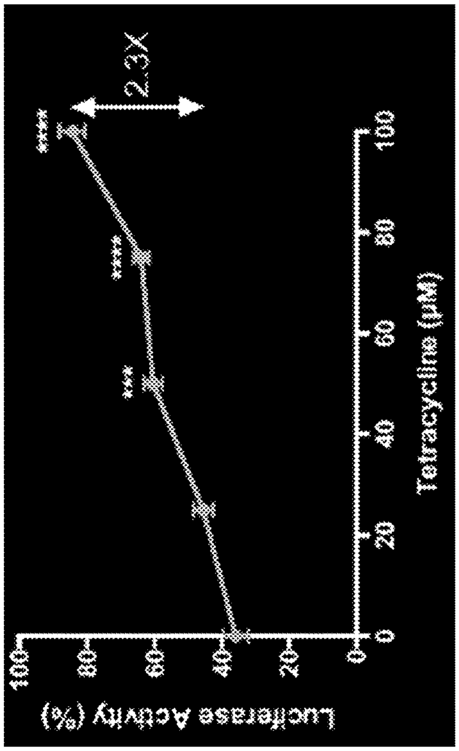
FIG. 12B depicts the dynamic range of the tet-SLIM switch of FIG. 12A.
Figure 12C:
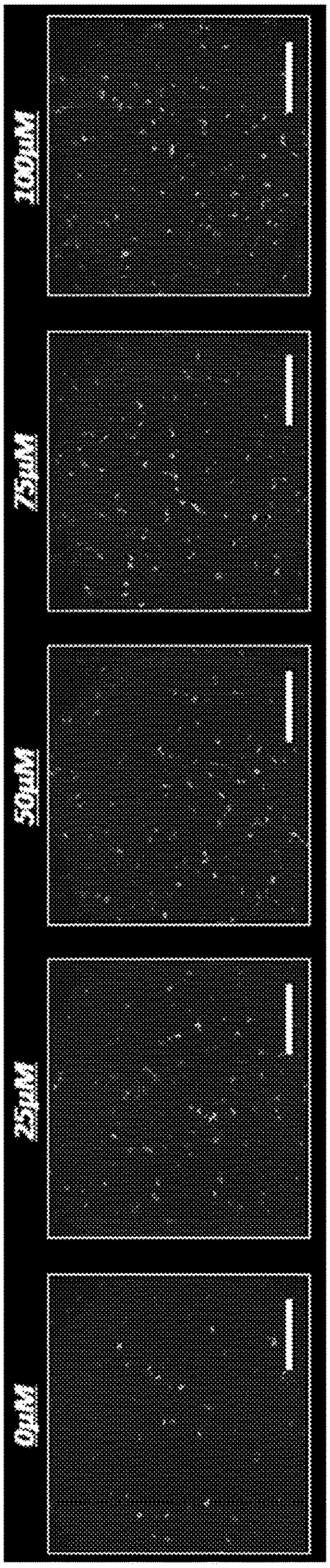
FIG. 12C are fluorescent imaging of cells treated with 0-100 μM of tetracycline which were transduced with the tet-SLIM switch construct of 12A.
Figure 13A:
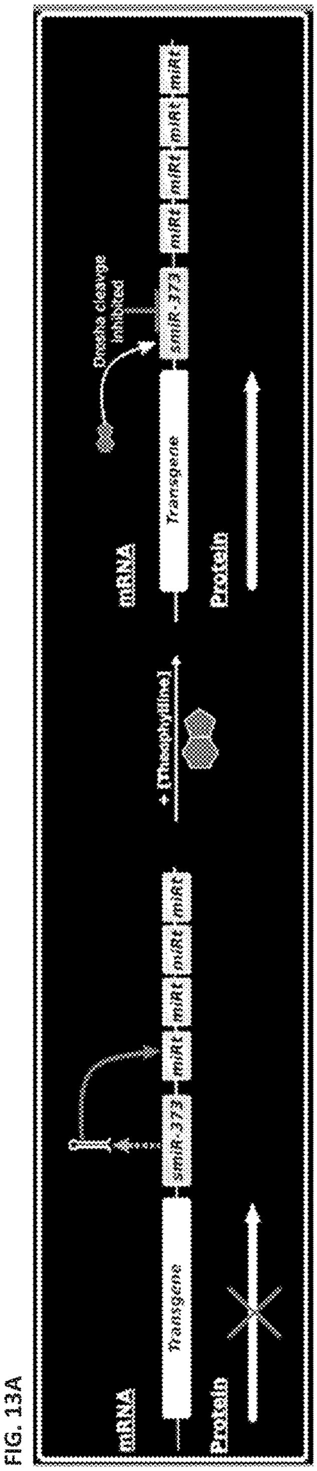
FIG. 13A depicts the mRNA of a construct comprising the theophylline SLIM switch (ON-type switch).
Figure 13B:
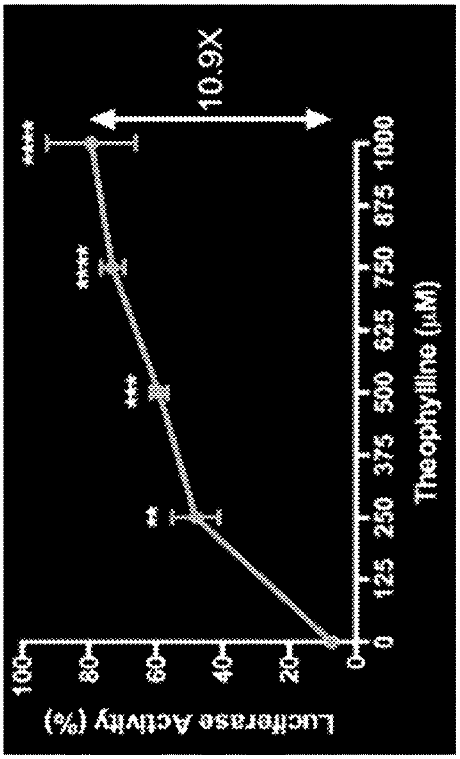
FIG. 13B depicts the dynamic range of the theo-SLIM switch of FIG. 13A.
Figure 13C:
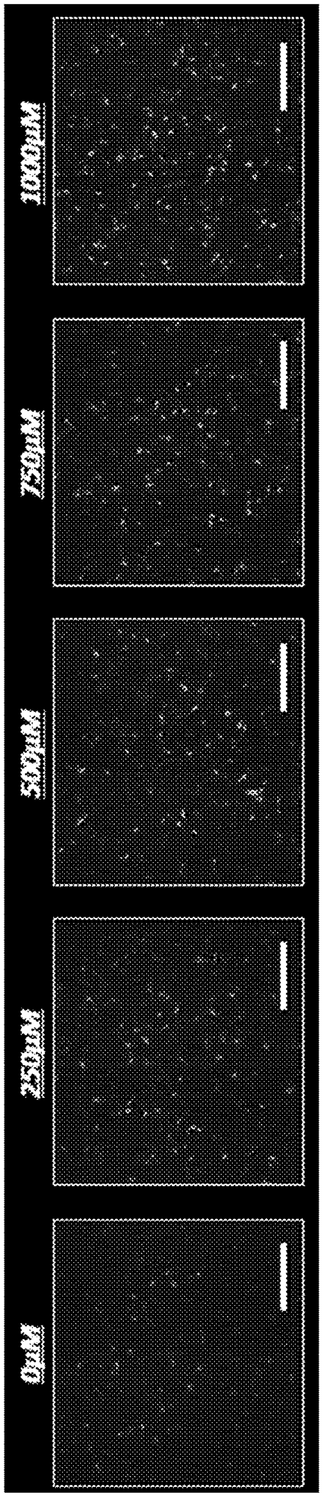
FIG. 13C are fluorescent imaging of cells treated with 0-100 μM of theophylline which were transduced with the theo-SLIM switch construct of 13A.

Experiments as described in Example 2A were also carried out using the newly designed Tet-SLIM and Theo-SLIM switches including target miRNA sequence, as depicted in FIGS. 12A and 13A, respectively. FIGS. 12B and 13B show the dynamic range for both switches, while FIGS. 12C and 13C depict fluorescence as seen in the cells treated with 0-100 μM of their respective ligands. Both SLIM riboswitches had an increased dynamic range over similar riboswitches known in the art.

Example 3: Mouse Study Using SLIM Containing Anti-VEGF Compound

Adult (>2 months old) wild-type (e.g. C57Bl/6j strain) mice (n=20) will be purchased from an approved supplier (e.g. Jackson Laboratories) and group housed at the Medical College of Wisconsin in standard conditions. After a period of acclimatization, each animal will undergo bilateral intravitreal injections. One eye will receive 2 μl sterile buffer (HBSS+0.014% tween-20) containing purified recombinant adeno-associated virus (rAAV) packaging the cDNA sequences required for biosynthesis of a vascular endothelial growth factor (VEGF) inhibitor (e.g. Aflibercept (Eylea)) under control the SLIM gene-switch (named herein, rAAV.SLIM.αVEGF). The contralateral eye will receive an injection of buffer only to control for the effects of the surgical intervention. Four weeks will be allowed for incorporation of the rAAV.SLIM.αVEGF vector into cells of the retina; based on preliminary data we expect ganglion cells and Müller glia be effectively transduced. All eyes will be imaged by fluorescein angiography (FA) using a confocal scanning laser ophthalmoscope to establish the baseline integrity of the retinal and choroidal blood vessels. Animals will subsequently be assigned randomly to either the treatment (receives activating ligand) or control (no activating ligand) group. Acute choroidal neovascularization (CNV) will be induced in all eyes by making a small hole in Bruch's membrane with a focused infrared laser beam. The extent of CNV formation will be assessed seven and 14 days thereafter by FA.

It is anticipated that animals of the control group (no ligand=low-level αVEGF expression) will demonstrate CNV formation in the rAAV.SLIM.αVEGF injected eyes that is similar in extent to the contralateral buffer injected eyes. By contrast, it is anticipated that animals of the experimental group (with ligand=high-level αVEGF expression) will exhibit significantly reduced CNV formation in rAAV.SLIM.αVEGF injected eyes compared to the contralateral buffer injected eyes. This will serve to demonstrate that rAAV-mediated over-expression of a VEGF inhibitor is an effect method for preventing CNV formation, and that the expression levels of the VEGF inhibitor can be modulated (i.e. increased) through supplementation of the activating ligand, leading to a reduction in CNV formation. All animals will subsequently be euthanized to allow collection of the eyes for biochemical analysis, allowing direct quantification of αVEGF protein levels within treated (with ligand) and control (no ligand) eyes.

Example 4: Treatment of AMD Using rAAV.SLIM.αVEGF Vector

Due to the slowly progressing nature of AMD, a therapeutic window exists between initial diagnosis and the onset of severe visual impairment in which to intervene. Following diagnosis, patients would receive a single intravitreal injection of the rAAV.SLIM.αVEGF vector suspended in a physiologically relevant buffer. The current treatment paradigm for AMD patients involves monthly or bimonthly intravitreal injections of anti-VEGF protein; a single-dose administration rAAV.SLIM.αVEGF would therefore represent a significantly less invasive treatment alternative. Intravitreal injections of anti-VEGF protein are currently performed under local anesthesia as an outpatient procedure; it is anticipated that this would also be the case for intravitreal administration of the rAAV.SLIM.αVEGF vector. Four to eight weeks would be allowed for incorporation of the rAAV.SLAM.F2α vector into cells of the inner retina. The patient could continue to receive conventional anti-VEGF therapy during this time. The SLIM technology is an ON-type switch; as such anti-VEGF protein will not be expressed in the patient's eye until the activating ligand is provided. Anti-VEGF protein expression levels in the patient eye will be regulated through oral administration of the activating ligand (e.g. in tablet form). The SLIM technology is dose-dependent, allowing the patient/physician to precisely modulate anti-VEGF expression levels within the eye. The retinal cells targeted as part of this procedure do not divide. As a consequence, following incorporation of the vector into those cells, it is anticipated that the rAAV.SLIM.αVEGF vector will persist throughout the patient's lifetime. Anti-VEGF expression can therefore be induced at any time throughout the patient's lifetime by administration of the activating ligand, negating the need for repetitive intra-ocular injections.

Example 5: AAV-Riboswitch for Treating AMD

Current treatment methodologies for treating AMD focus on the administration soluble receptors or neutralizing antibodies raised against VEGF-A protein in order to inhibit its pro-angiogenic function. Eylea (aflibercept), a recombinant fusion VEGF trap licensed by the Food and Drug Administration for the treatment of wet AMD in 2011, has been found to be highly effective at treating CNV in patients with wet AMD. Although this approach has been largely successful at preventing CNV formation, it requires a monthly high-dose intravitreal injection of anti-VEGF agents throughout a patient's lifetime, resulting in a substantial financial and economic burden. Moreover, continuous bolus administration of both Eylea and Lucentis over multiple years has been shown to accelerate the rate of retinal and choroidal atrophy. Patients are also at an increased risk for injection related complications such as endophthalmitis and cataract formation. In this Example, we combine several technologies developed within our laboratory to create an inducible rAAV-based gene therapy approach to treat wet AMD following a single intravitreal administration.

Figures 14E, 14F, 14G, 14H, 14I, 14J, 14K, 14L:
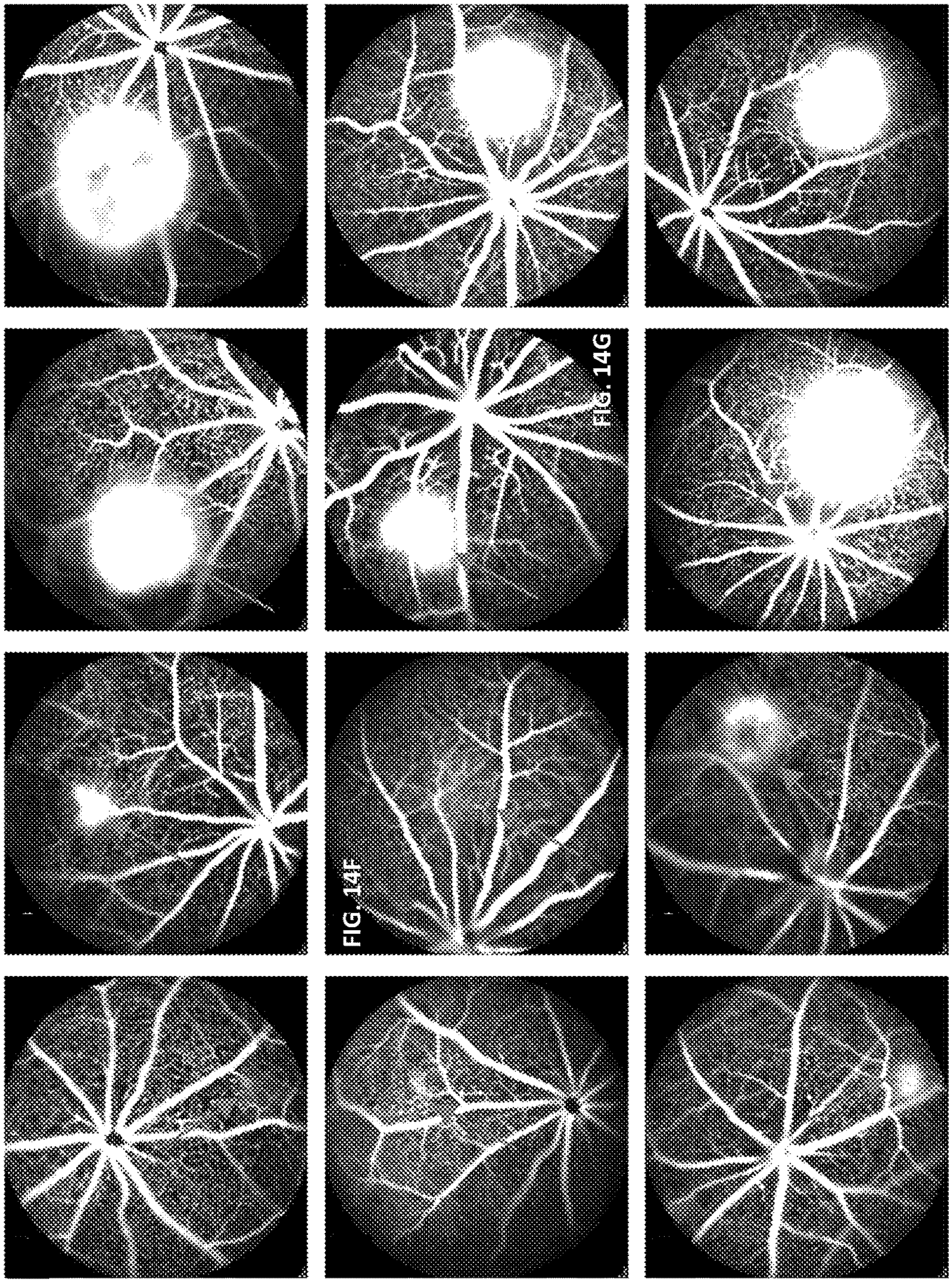

We assessed whether rAAV-mediated over-expression of Eylea is capable of preventing CNV formation following laser injury to Bruch's membrane. By incorporating a tetracycline-responsive riboswitch (1xTC45) riboswitch in the 3'-UTR of the expression cassette, we were also able to address whether modulating the intraocular concentration of Eylea led to an alteration in the severity of CNV lesions observed. To this end, age-matched C57BL/6J mice were unilaterally injected with either PBS (n=10), $1.0\times10^{10}$ vg of rAAV2/2 [MAX].smCBA-Eylea (n=10) or $1.0\times10^{10}$ vg rAAV2/2 [MAX].smCBA-Eylea-1x-TC45 (n=20). Immediately following injections, half of the mice (n=10) injected with rAAV2/2 [MAX].smCBA-Eylea-1x-TC45 were placed on diet containing 50 mg/g tetracycline. Six weeks post-injection, CNV formation was initiated by rupturing Bruch's membrane using an infrared laser diode (see methods). Seven days following laser injury, neovascular lesion size and leakage was assessed via fluorescein angiography using cSLO imaging. The majority of mice ubiquitously expressing Eylea (smCBA-Eylea) either did not develop lesions at the site of laser injury, or developed small grade 1 or 2A type lesions that leaked minimal fluorescein, even after a 5-minute period. (FIG. 14A-C). Mice injected with the 'OFF-type' smCBA-Eylea-1x-TC45 vector and placed on regular diet also predominantly developed only minor lesions, though a small increase in the number of 2B lesions were observed compared to the non-inducible Eylea construct (FIG. 14D-F). Lowering Eylea expression through activation of the TC45 riboswitch greatly increased the severity of CNV lesions (FIG. 14G-I) to the extent that they were similar in extent to PBS-sham injected mice (FIG. 14L-J).

Lesion images were graded by three blinded scientists using the grading system described by Krzystolik et al. (see methods for details). Importantly, grade distribution was significantly different for each treatment group Mice receiving a sham injection had the highest incidence of clinically significant 'Grade 2B' lesions, while mice ubiquitously over-expressing Eylea (smCBA-Eylea) had the lowest incidence of 'Grade 2B' lesions.

Figure 15A:
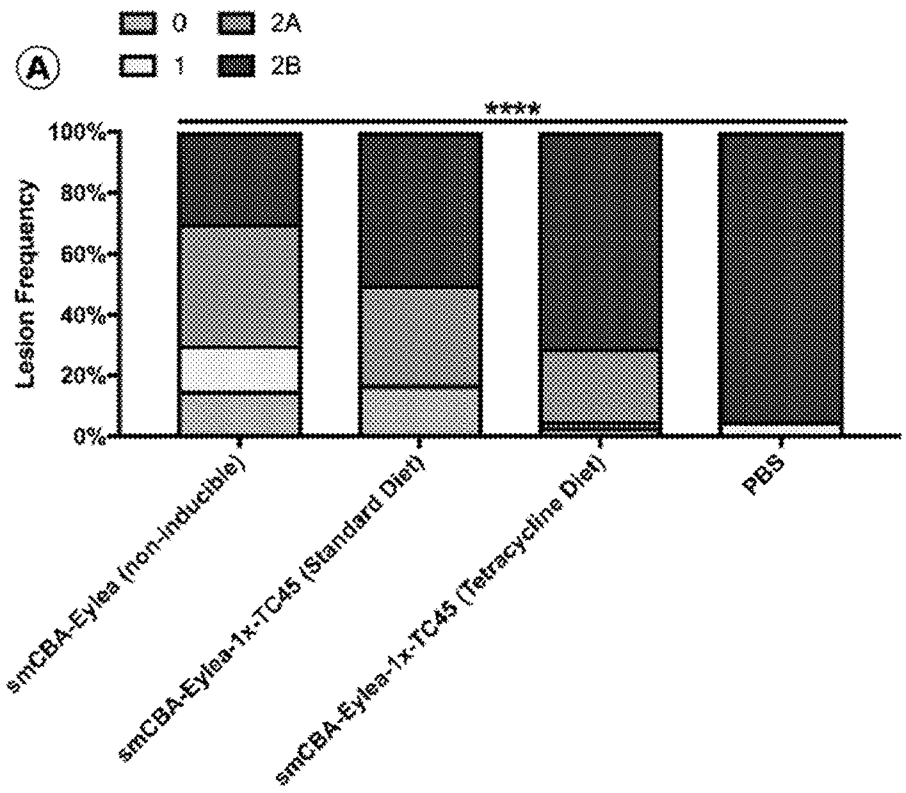
FIGS. 15A-15B demonstrate intraocular concentration of Eylea correlated strongly with severity of CNV lesions. (A) Distribution of lesions graded independently by three blinded scientists. N=16-20 lesions per group, p<0.0001, Chi-squared test). (B) Intraocular levels of non-complexed Eylea assayed by ELISA. N=5 eyes per group.
Figure 15B:
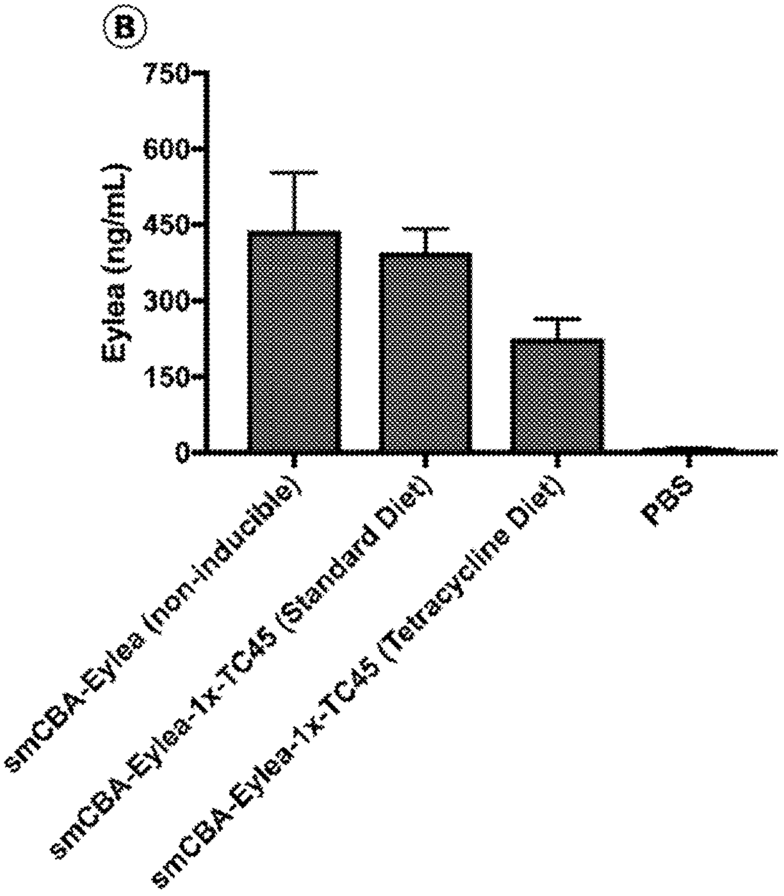
Figures 17A, 17B, 17C:
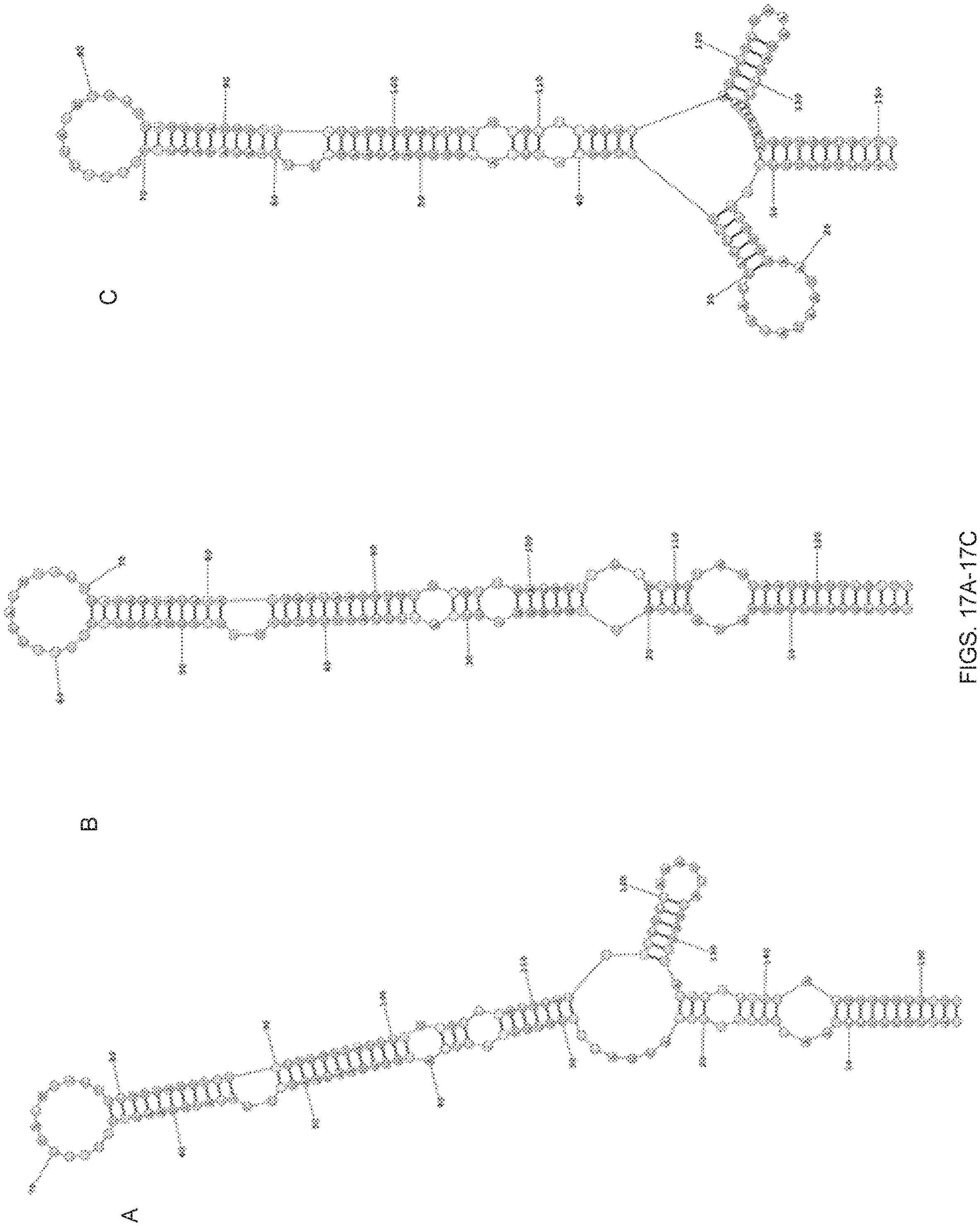
FIGS. 17A-17C are schematic representations of 6S-folini acid-responsive SLIM (A) (SEQ ID NO:21), theophylline-responsive SLIM (B) (SEQ ID NO:26) and tetracycline-responsive SLIM (C) (SEQ ID NO:31).
Figure 20:
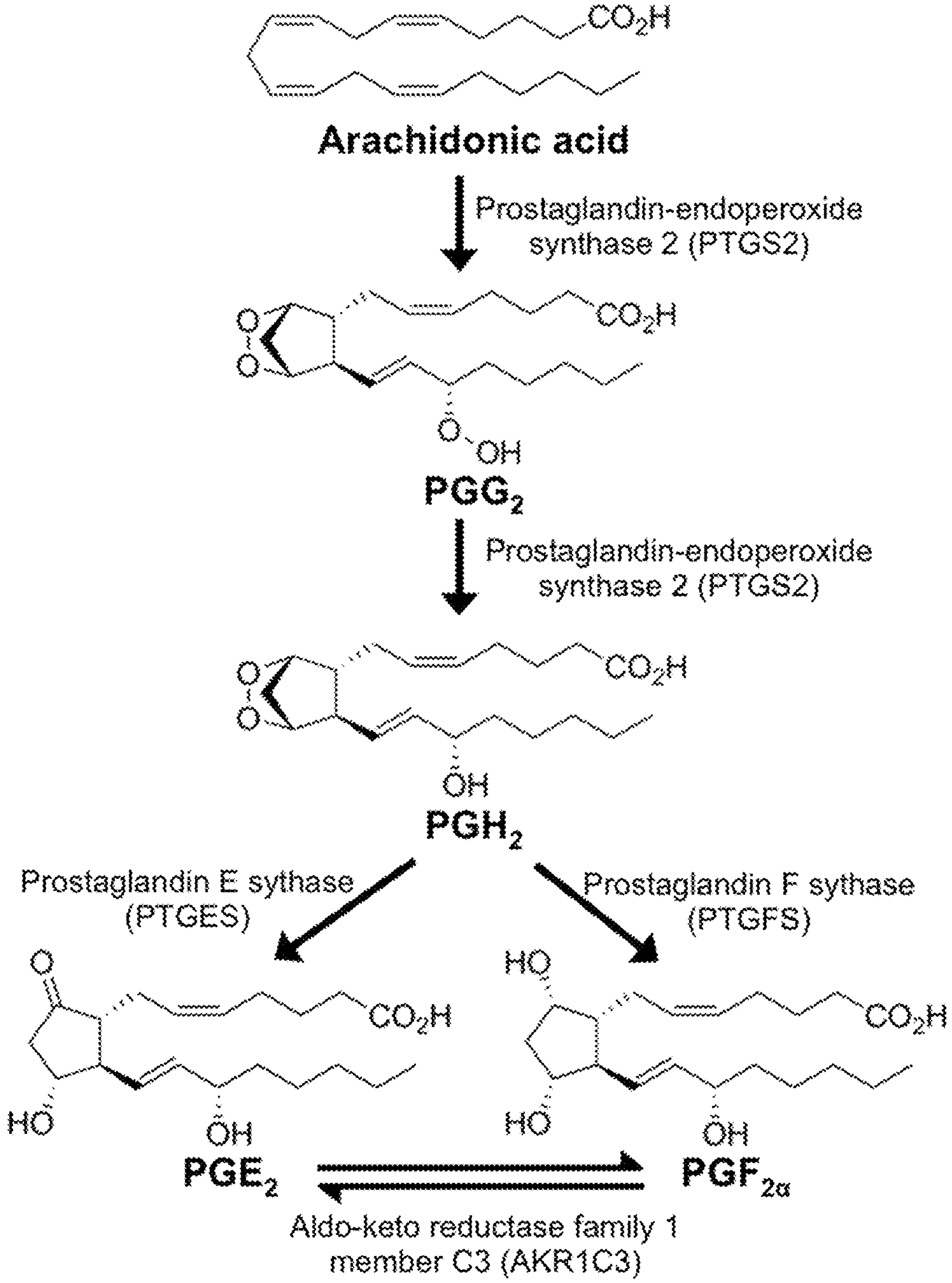
Related art FIG. 20
FIG. 20 demonstrates the enzymes of the PGF2α biosynthesis pathway.

Notably, downregulating Eylea expression through activation of the TC45 riboswitch resulted in a considerable increase in the incidence of 'Grade 2B' lesions compared to rAAV2 [MAX].smCBA-Eylea-1x-TC45 injected mice receiving standard diet (FIG. 15A). Finally, we determined the levels of non-complexed Eylea in each sample using an Eylea-specific ELISA (Eagle Biosciences). As expected, eyes injected with the non-inducible construct (smCBA-Eylea) contained the highest levels of free Eylea (438 ng/ml). Moreover, high levels of free Eylea were detected in animals injected with vector containing the tunable construct (395 ng/mL), though levels were lower than animals injected with the non-inducible construct. Importantly, tetracycline-mediated activation of the TC45 riboswitch resulted in a significant 1.75-fold decrease in non-complexed Eylea ($p<0.05$). (FIG. 15B) The levels of free Eylea correlated strongly with the occurrence of clinically significant lesions.

Example 6: Self-Targeting Ligand Inactivating miRNAs for AMD Treatment in Humans A SLIM switch requires the basal region of a pri-miRNA to be replaced with an aptamer. This sequence is cloned into either the 3'- or 5' untranslated region of an expression cassette. Additionally, miRNA target sites that are complementary to the sequence of the mature miRNA can be included in one or multiple copies at either the 5' or 3' untranslated region of the cassette.

Self-targeting Ligand Inactivated miRNAs (SLIM) switches function by regulating gene expression at the post-transcriptional level. In conditions when the activating ligand is absent, the pri-miRNA will be cleaved by drosha from the nascent transcript. This miRNA will be processed and act as the second mechanism of gene silencing, through binding of the complementary target sites. When the activating ligand is provided, gene expression is unaltered.

Multiple copies of each riboswitch (SLIM) can be included into the 3'-untranslated region of the gene of interest. Each riboswitch appears to have an optimal number of copies as shown in Table 2. Furthermore, multiple copies of miRNA target sites can be included in the 3' or 5' untranslated region.

Due to the slowly progressing nature of AMD, a therapeutic window exists between initial diagnosis and the onset of severe visual impairment in which to intervene. Following diagnosis, patients would receive a single intravitreal injection of the rAAV.SLIM.αVEGF vector suspended in a physiologically relevant buffer. The current treatment paradigm for AMD patients involves monthly or bimonthly intravitreal injections of anti-VEGF protein. Thus, a single-dose administration rAAV.SLIM.αVEGF would therefore represent a significantly less invasive treatment alternative. Intravitreal injections of anti-VEGF protein are currently performed under local anaesthesia as an outpatient procedure; it is anticipated that this would also be the case for intravitreal administration of the rAAV.SLIM.αVEGF vector. The patient could continue to receive conventional anti-VEGF therapy during this time. The SLIM technology is an ON-type switch; as such anti-VEGF protein will not be expressed in the patient's eye until the activating ligand is provided. Anti-VEGF protein expression levels in the patient eye will be regulated through oral administration of the activating ligand (e.g. in tablet form). The SLIM technology is dose-dependent, allowing the patient/physician to precisely modulate anti-VEGF expression levels within the eye. The retinal cells targeted as part of this procedure do not divide. As a consequence, following incorporation of the vector into those cells, it is anticipated that the rAAV.SLIM.αVEGF vector will persist throughout the patient's lifetime. Anti-VEGF expression can therefore be induced at any time throughout the patient's lifetime by administration of the activating ligand, negating the need for repetitive intra-ocular injections.

Treating Glaucoma with Vectors Comprising Riboswitches

Primary open angle glaucoma (POAG) is the second leading cause of irreversible blindness worldwide and is characterized by progressive loss of retinal ganglion cells and atrophy of the optic nerve, leading to visual field deficits. The major risk factor for POAG is increased intraocular pressure (IOP) resulting from decreased aqueous humor outflow. The gold standard clinical therapy for glaucoma is to reduce IOP through a combination of topical drug administration, and in late-stage disease, surgery. Unfortunately, due to the largely asymptomatic (i.e. non-painful) nature of glaucoma and the necessity to maintain a lifelong daily treatment regimen, patient compliance with drug therapies is extremely poor (<20%), leading to the development of severe sight-threatening complications, even in patients diagnosed early.

AAV-Riboswitch Experiments—A Model for Treating Glaucoma

Prostaglandin analogs (e.g. Latanprost) are administered clinically as esterified pro-drugs that are absorbed across the corneal epithelium and are hydrolyzed into their active form as they pass through the stroma and corneal endothelium before diffusing into the aqueous humor. Binding of soluble PGF2α analog to PTGFR triggers up-regulation of matrix metaloprotinase (MMP) production within the ciliary muscle that promotes remodelling of the extracellular matrix and increased uveoscleral aqueous outflow. Native PGF2α is enzymatically derived from aracadonic acid, which is present in the cornea at high levels, via a multistep process.

De novo biosynthesis and secretion of PGF2α from the cornea into the anterior chamber promises to be an effective strategy for lowering IOP that improves upon the current gold-standard clinical treatment approach. We have demonstrated that over-expression of prostaglandin endoperoxide synthase 2 (PTGS2), the rate limiting enzyme in PGF20 biosynthesis, and PTGFR, causes a significant decrease in IOP over a period of three months. The cDNA sequences (below) for both enzymes were incorporated into a AAV expression construct (complete sequence below) incorporating either no riboswitch (non-inducible) or with a 3' TC40 and 5' TC45 tetracycline inducible riboswitch. Mice received intracamereal injections of PBS (N=10), rAAV.smCBA-PTGFR.P2A.PTGFR (N=10, non-inducible) or rAAV.smCBA-TC40-PTGFR.P2A.PTGFR-TC45 (inducible). IOP was measured by rebound tonometry before and 12 weeks following injection. Half of the inducible mice were placed on tetracycline containing diet for that period. Mice placed on diet (PGF2alpha Expression OFF) showed no decreased in intraocular pressure over the 12 week period. Mice on normal diet (PGF2alpha expression ON) showed a highly significant decrease in IOP, similar to when PGF2alpha is constitutively expressed (no switch).

Sequence Listing Statement and Reference to a Sequence Listing Submitted Via Patent Center The application includes the sequence listing through-out the specification and in the attached sequence listing. The content of the ST26 format sequence listing named "650053_00984.xml" which is 136,298 bytes in size and was created on Jul. 21, 2023 and electronically submitted via Patent Center herewith the application is incorporated herein by reference in its entirety. A few sequences are listed below, but are not to be considered a full listing.

```
L2bulge9 (Theophylline OFF switch)
                                         (SEQ ID NO: 11)
CTCGAGGCGATCGCAAACAAACAAAGCTGTCACCGGATGTGCTTTCCG

GTCTGATGAGTCCGTTGTCCAATACCAGCATCGTCTTGATGCCCTTGG

CAGTGGATGGGGACGGAGGACGAAACAGCAAAAAGAAAAATAAAAATT

TTTTTTTAATTAATCTTGGGCCC
```

-continued

```
L2bulge18tc (Tetracycline ON switch)
                                         (SEQ ID NO: 12)
CTCGAGGCGATCGCAAACAAACAAAGCTGTCACCGGATGTGCTTTCCG

GTCTGATGAGTCCGTTGTCCAAAACATACCAGATTTCGATCTGGAGAG

GTGAAGAATTCGACCACCTGGACGAGGACGGAGGACGAAACAGCAAAA

AGAAAAATAAAAATTAATTAATCTTGGGCCC

Theo6HDV (Theophylline OFF switch)
                                         (SEQ ID NO: 13)
ATGGCCGGCATGGTCCCAGCCTCCTCGCTGGCGCCGGCTGGGCAACCA

CATACCAGCCGAAAGGCCCTTGGCAGGTGGGCGAATGGGACGCACAAA

TCTCTCTAGCTTCCCAGAGAGAAGCGAGAGAAAAGTGGCTCTC

GuaM8HDV (Guanine OFF switch)
                                         (SEQ ID NO: 14)
ATGGCCGGCATGGTCCCAGCCTCCTCGCTGGCGCCGGCTGGGCAATGC

TATAATCGCGTGGATATGGCACGCAAGTTTCTACCGGGCACCGTAAAT

GTCCGACTAGTAGCGAATGGGACGCACAAATCTCTCTAG

K19 (Tetracycline ON switch)
                                         (SEQ ID NO: 15)
CAAACAAACAAAGGCGCGTCCTGGATTCGTGGTAAAACATACCAGATT

TCGATCTGGAGAGGTGAAGAATACGACCACCTGTAGTATCCAGCTGAT

GAGTCCCAAATAGGACGAAACGCGCTAAACAAACAAAC

TC40 (Tetracycline OFF switch)
                                         (SEQ ID NO: 16)
CTGAGGTGCAGGTACATCCAGCTGACGAGTCCCAAATAGGACGAAAGG

GAGAGGTGAAGAATACGACCACCTAGGCTCGAAAGAGCCTAAAACATA

CCTTTCCTGGATTCCACTGCTATCCAC

Tet-SLIM
                                         (SEQ ID NO: 17)
CTAGCACGGGTCCCTAAAACATACCGTGAGCGCGAAAGCGCCCCCATT

TTGAGTTAGTGAAGCCACAGATGTAACTCAAAATGGGGGCGCTTTCCC

GCCTACGGAGAGGTGAAGAATACGACCACCTAGAAGCTTATTGGTACA

TGATAACACCCCAAAATCGAAGCACTTCAAAAACACCCCAAAATCGAA

GCACTTCAAAAACACCCCAAAATCGAAGCACTTCAAAAACACCCCAAA

ATCGAAGCACTTCAGTCTCAGGCATCGTACGATGTCGACCTGCAGG
```

We claim:

1. A method of reducing at least one symptom of glaucoma in a subject in need thereof, the method comprising administering an exogenous nucleic acid construct to the eye of the subject, the exogenous nucleic acid construct comprising SEQ ID NO: 58 or a transgene that regulates prostaglandin 2 alpha synthesis, wherein the transgene that regulates prostaglandin 2 alpha synthesis is selected from the group consisting of SEQ ID NOs: 52, 53, and 54.

2. The method of claim 1, wherein the method reduces the intraocular pressure within an eye of the subject.

3. The method of claim 1, wherein the construct is administered via intra-cameral injection.

4. The method of claim 1, wherein the exogenous nucleic acid construct comprises SEQ ID NO: 52.

5. The method of claim 1, wherein the exogenous nucleic acid construct comprises SEQ ID NO: 53.

6. The method of claim 1, wherein the exogenous nucleic acid construct comprises SEQ ID NO: 54.

7. The method of claim 1, wherein the exogenous nucleic acid construct comprises SEQ ID NO: 58.

8. A method of treating glaucoma in a subject in need thereof, the method comprising administering a viral construct comprising a nucleic acid comprising SEQ ID NO: 58 or a transgene that regulates prostaglandin 2 alpha synthesis selected from the group consisting of SEQ ID NOs: 52, 53, and 54.

9. The method of claim 8, wherein the nucleic acid comprises SEQ ID NO: 52.

10. The method of claim 8, wherein the nucleic acid comprises SEQ ID NO: 53.

11. The method of claim 8, wherein the transgene that regulates prostaglandin 2 alpha synthesis is SEQ ID NO: 54.

12. The method of claim 8, wherein the nucleic acid comprises SEQ ID NO: 58.

13. The method of claim 8, wherein the viral construct is an adeno-associated virus (AAV), a lentivirus, an adenovirus, a plasmid, a herpes simplex virus, a baculovirus, or a bacteriophage.

14. The method of claim 13, wherein the viral construct is an AAV.

15. A virus comprising a sequence encoding a vascular endothelial growth factor (VEGF) inhibitor, wherein the sequence encoding the vascular endothelial growth factor inhibitor is SEQ ID NO: 18.

16. A method of treating a disease associated with VEGF expression, the method comprising administering a therapeutically effective amount of the virus of claim 15 to a subject in need thereof.

17. The method of claim 16, wherein administering comprises intracameral administration.

18. The method of claim 16, wherein the subject is suffering from age-related macular degeneration (AMD).

19. The method of claim 18, wherein the AMD is wet AMD.

* * * * *